United States Patent
Canaani et al.

(10) Patent No.: US 11,118,182 B2
(45) Date of Patent: Sep. 14, 2021

(54) MODULATORS OF HUMAN KAI1 METASTASIS SUPPRESSOR GENE, METHODS AND USES THEREOF

(71) Applicant: RAMOT AT TEL-AVIV UNIVERSITY LTD., Tel Aviv (IL)

(72) Inventors: Dan Canaani, Tel Aviv (IL); Ronni Aram, Tel Aviv (IL); Iris Dotan, Tel Aviv (IL); Pnina Gottfried Komlosh, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 16/461,941

(22) PCT Filed: Nov. 16, 2017

(86) PCT No.: PCT/IL2017/051253
§ 371 (c)(1),
(2) Date: May 17, 2019

(87) PCT Pub. No.: WO2018/092137
PCT Pub. Date: May 24, 2018

(65) Prior Publication Data
US 2019/0300884 A1 Oct. 3, 2019

Related U.S. Application Data

(60) Provisional application No. 62/423,530, filed on Nov. 17, 2016.

(51) Int. Cl.
| | | |
|---|---|---|
| *C07H 21/04* | (2006.01) | |
| *C12N 15/113* | (2010.01) | |
| *A61P 17/02* | (2006.01) | |
| *A61P 35/04* | (2006.01) | |
| *A61K 9/127* | (2006.01) | |
| *C12Q 1/6886* | (2018.01) | |
| *G01N 33/50* | (2006.01) | |
| *G01N 33/52* | (2006.01) | |

(52) U.S. Cl.
CPC .......... *C12N 15/1135* (2013.01); *A61K 9/127* (2013.01); *A61P 17/02* (2018.01); *A61P 35/04* (2018.01); *C12N 15/113* (2013.01); *C12Q 1/6886* (2013.01); *G01N 33/502* (2013.01); *G01N 33/52* (2013.01); *C12N 2310/113* (2013.01); *C12Q 2600/136* (2013.01); *C12Q 2600/158* (2013.01); *C12Q 2600/178* (2013.01)

(58) Field of Classification Search
CPC .................................................. C12N 15/113
See application file for complete search history.

(56) References Cited

U.S. PATENT DOCUMENTS

2011/0189663 A1  8/2011  Cotterchio et al.

FOREIGN PATENT DOCUMENTS

| WO | 96/34117 A1 | 10/1996 |
| WO | 03/025217 A1 | 3/2003 |
| WO | 2008/106785 A1 | 9/2008 |
| WO | 2013/173605 A1 | 11/2013 |
| WO | 2013/173637 A1 | 11/2013 |

OTHER PUBLICATIONS

Liu, Wei M., and Xin A. Zhang. "KAI1/CD82, a tumor metastasis suppressor." Cancer letters 240.2 (2006): 183-194.*
Dai Weiqi et al., "Anti-miR-197 inhibits migration in HCC cells by targeting KAI 1 /CD82", Biochemical and Biophysical research Communications, Elsevier, Amsterdam, NL, vol. 446, pp. 541-548 (2014).
Miranti et al., "Controlling cell surface dynamics and signaling: How CD82/KAI1 suppresses metastasis", Cellular signaling, Elsevier Science Ltd, vol. 21, No. 2, DOI: 10.1016/J.CELLSIG., pp. 196-211 (2009).
Karen K. Phillips et al., "Correlation Between Reduction of Metastasis in the MDA-MB-435 Model System and Increased Expression of the Kai-1 Protein", Molecular Carcinogenesis, vol. 21, No. 2, DOI: 10.1002/(SICI) pp. 111-120 (1998).
Albrecht, Anne-Susann and Ulf Andersson Ørom. (2016). "Bidirectional Expression of Long ncRNA/protein-Coding Gene Pairs in Cancer." Briefings in functional genomics 15(3): 167-173.
Avivi Shira, Mor Amir, Dotan Iris, Tzadok Sivan, Kanter Itamar, Kinor Noa, Canaani Dan, and Shav-Tal Yaron (2017). PNAS USA 114: E8837-88460.
Chodroff, Rebecca A. et al. (2010). Genome biology 11(7): R72.
Cohen Z.R., Ramishetti S., Fehes-Yaloz N., Goldsmith M., Wohl ., Zibly Z., and Peer D. (2015). ACS Nano 9 : 1581-1591.
Duttke, Sascha H. C. et al. (2015). Molecular cell 57(4):674-84.
Feng J. et al., (2015). Cancer Metastasis Rev . 34:619-632.
Holen I, Speirs V, Morrissey B, Blyth K (2017). Dis Model Mech. 10:359-371.
Iyer M.K. et al., (2015). Nat. Genet. 47:199-208.
Lee, Ji Hee, Young-Woo Seo, Sei Ryun Park, Young Jin Kim, and Kyung Keun Kim. (2003). Cancer research 63(21):7247-55.
Malik, Faraz Arshad, Andrew J. Sanders, Mahmood A. Kayani, and Wen G. Jiang. (2009). Cancer genomics & proteomics 6(4):205-13.
Marques, Ana C. and Chris P. Ponting. (2009). Genome biology 10(11):R124.
Marreiros, Alexandra, Robert Czolij, Gina Yardley, Merlin Crossley, and Paul Jackson. (2003). Gene 302(1-2):155-64.

(Continued)

*Primary Examiner* — Kimberly Chong
(74) *Attorney, Agent, or Firm* — Browdy and Neimark, PLLC

(57) ABSTRACT

The invention provides modulators of human cancer and tumor metastasis in particular. More specifically the present disclosure relates to modulators of SKAI1BC, an antisense long non-coding RNA which was found to be an epigenetic suppressor of the metastasis suppressor gene KAI1/CD82, compositions, methods and uses thereof for decreasing metastasis, invasion and possibly also proliferation of cancer cells.

20 Claims, 14 Drawing Sheets

Specification includes a Sequence Listing.

(56) References Cited

OTHER PUBLICATIONS

Martianov, Igor, Aroul Ramadass, Ana Serra Barros, Natalie Chow, and Alexandre Akoulitchev. (2007). Nature 445(7128): 666-70.
Morris, Kevin V, Sharon Santoso, Anne-Marie Turner, Chiara Pastori, and Peter G. Hawkins. (2008). PLoS genetics 4(11): e1000258.
Morris K.V. and Mattick J.S. (2014). Nat. Rev. Genet. 15: 423-437.
Orom, Ulf Andersson and Ramin Shiekhattar. (2011). Trends in genetics : TIG 27(10):433-39.
Osato, Naoki, Yoshiyuki Suzuki, Kazuho Ikeo, and Takashi Gojobori. (2007). Genetics 176(2):1299-1306.
Schmitt A.H. and Chang H.Y. (2016). Cancer Cell 29:452-463.
Wang, Xiangting et al. (2008). Nature 454(7200):126-30.
Yang, X. et al. (2000). Clinical cancer research : an official journal of the American Association for Cancer Research 6(9): 3424-29.
Yu, Wenqiang et al. (2008). Nature 451(7175):202-6.
Zhang, Fan, Liang Zhang, and Caiguo Zhang. (2016). Tumour biology : the journal of the International Society for Oncodevelopmental Biology and Medicine 37(1):163-75.

Database NCBI Sequence GenBank accession No. AAC51205.1, downloaded from www.ncbi.nlm.nih.gov/protein/AAC51205.1 on Apr. 6, 2019.
Database NCBI Sequence GenBank accession No. U20770.1, downloaded from www.ncbi.nlm.nih.gov/nuccore/U20770.1 on Apr. 6, 2019.
Marino et al., "Identification and validation of genes with expression patterns inverse to multiple metastasis suppressor genes in breast cancer cell lines", Clinical & experimental metastasis, pp. 771-786, vol. 31 (Oct. 2014).
Aram et al.,"Identification of a novel metastasis inducing lncRNA which suppresses the KAI1/CD82 metastasis suppressor gene and is upregulated in triple-negative breast cancer", Oncotarget, pp. 67538-67552, vol. 8, No. 40 (Jun. 2017).
Database NCBI Sequence 5678 from Patent EP2079839. Genebank accession No. HI422590.1. URL: https://www.ncbi.nlm.nih.gov/nucleotide/311815410?report=genbank&log$=nucltop&blast_rank=5&RID=2CZ4XXEB014, downloaded May 16, 2019.

* cited by examiner

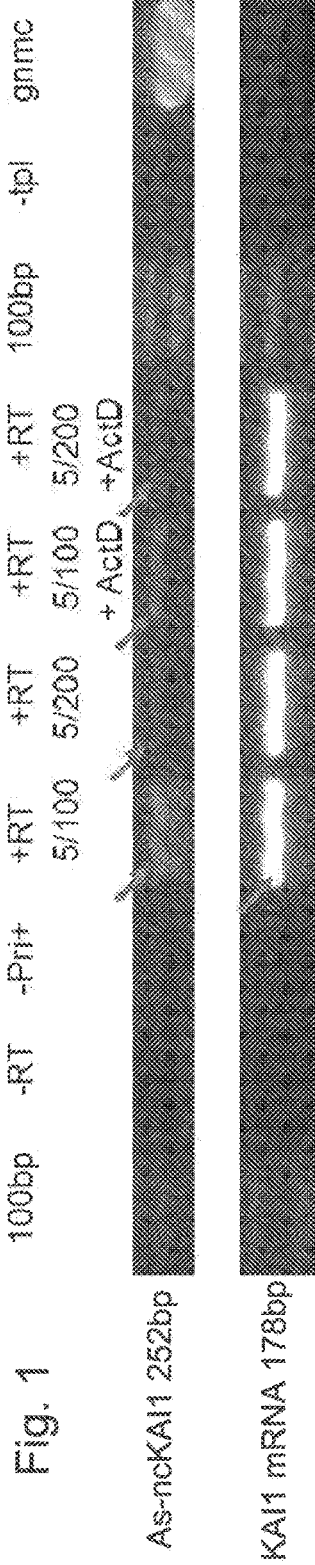
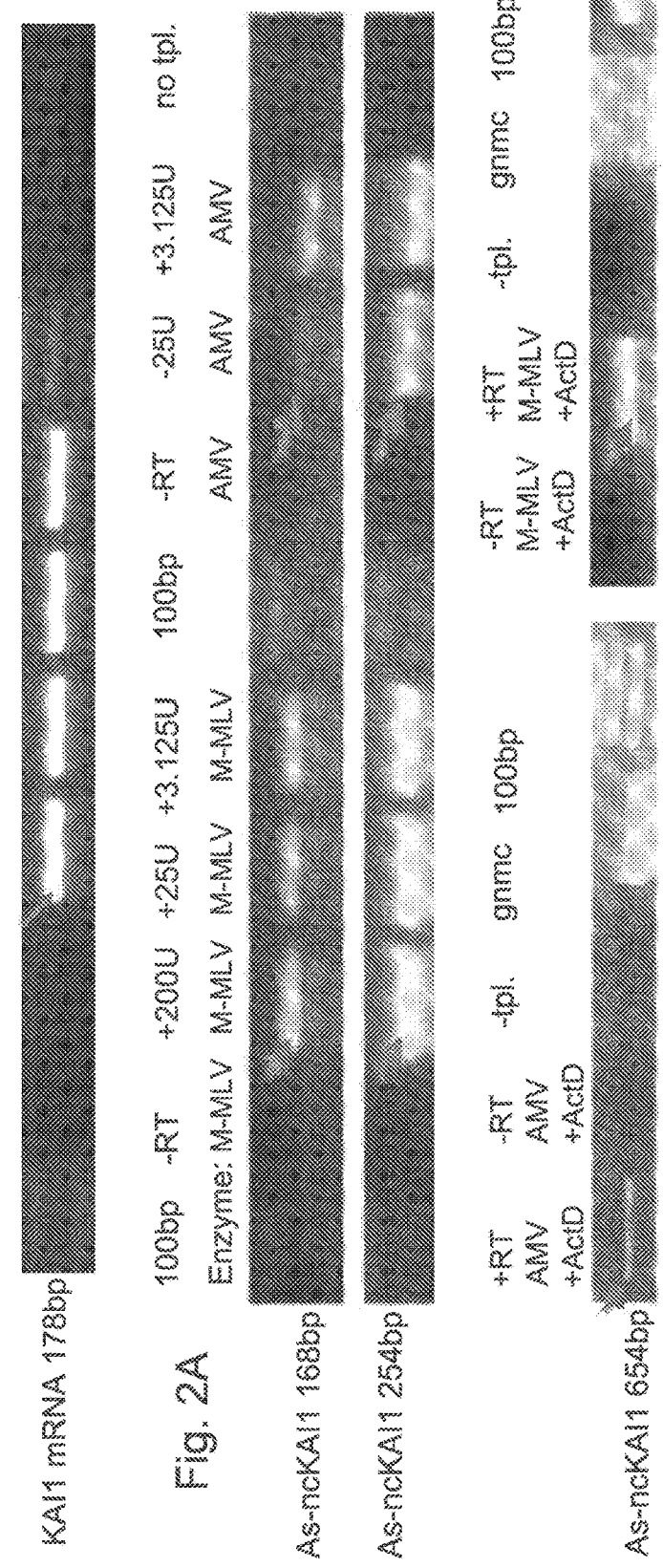

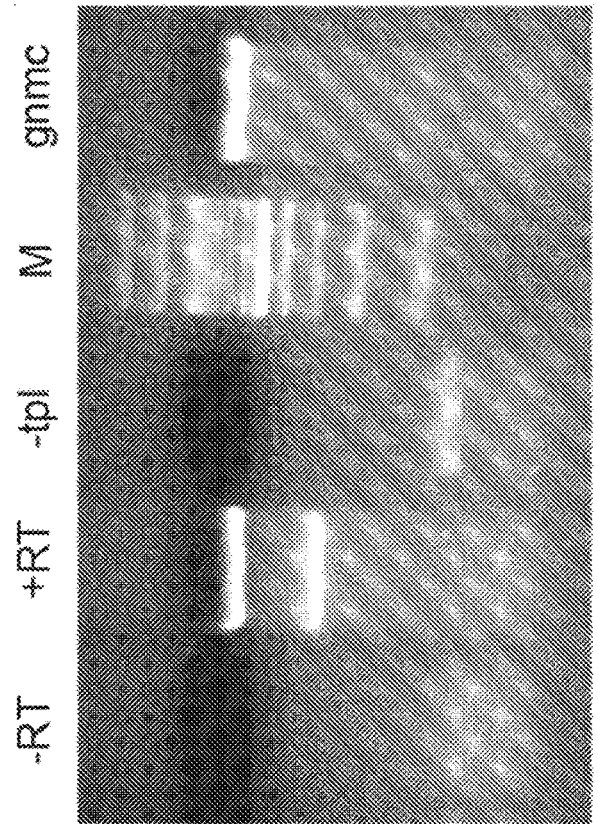
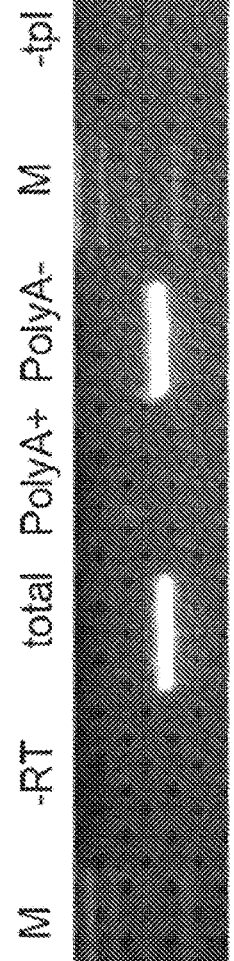
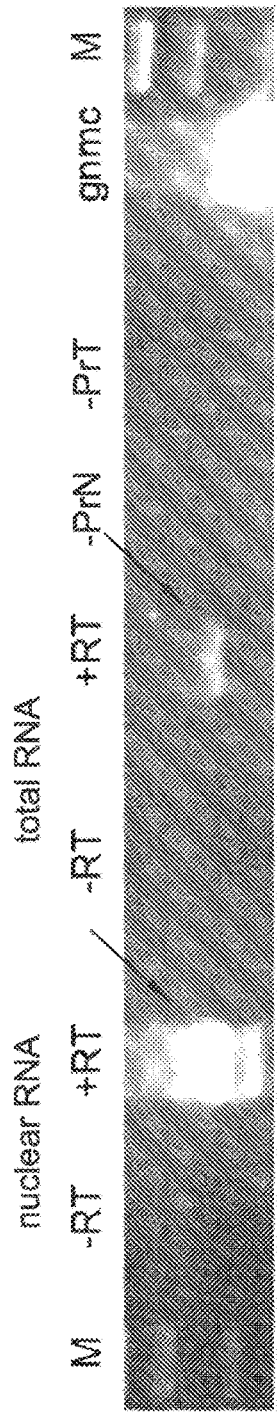
Fig. 4
Fig. 5A
Fig. 5B

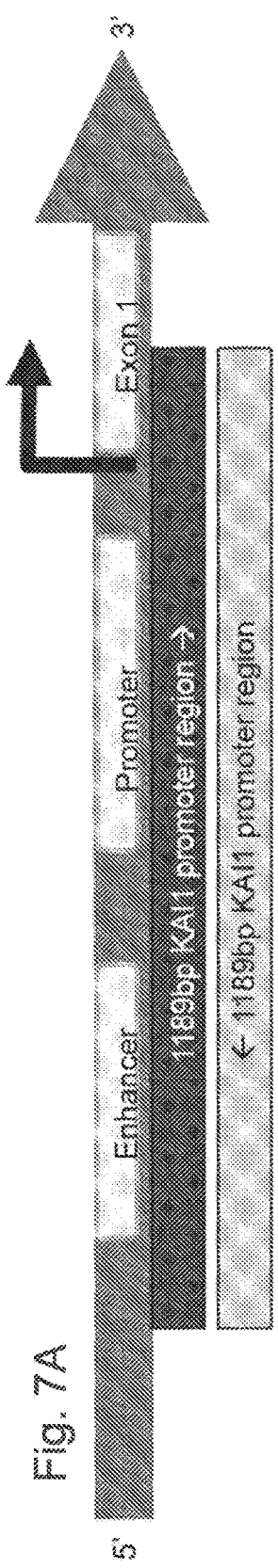
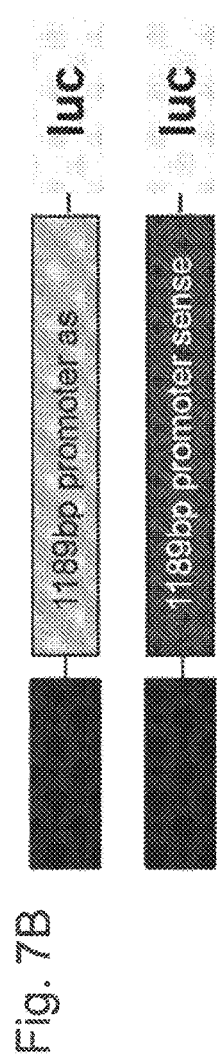
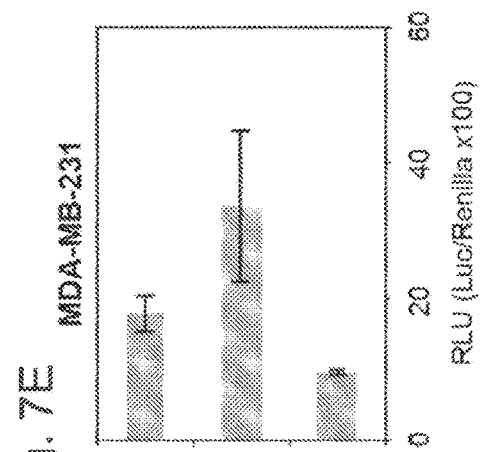
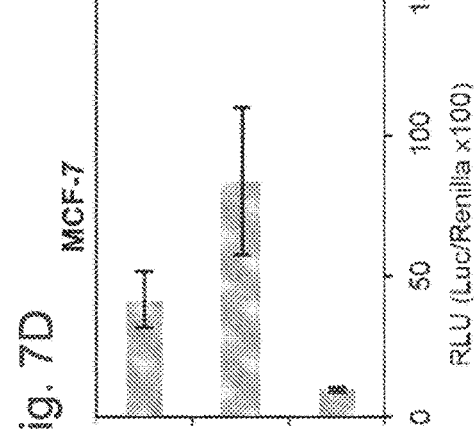
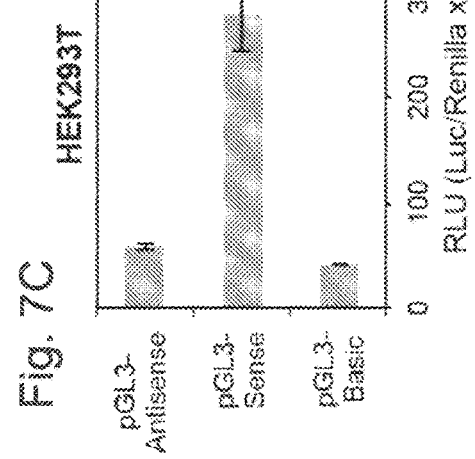

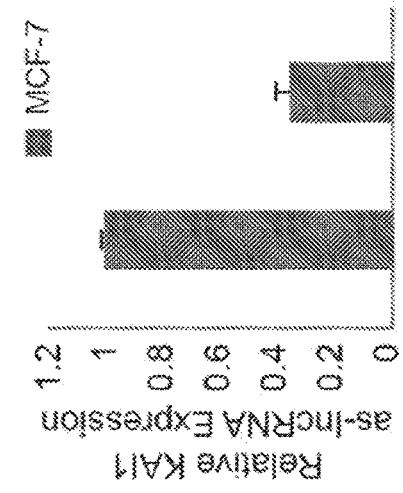
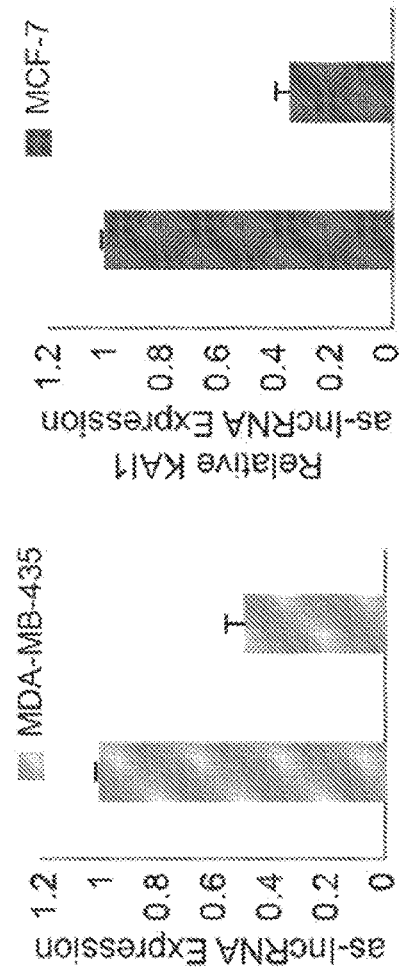
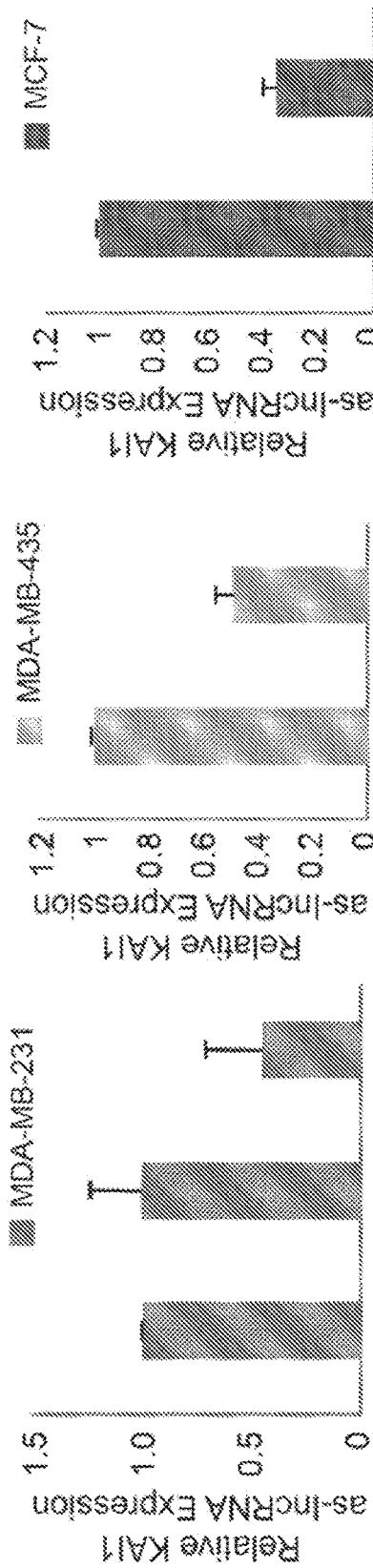
Fig. 11A    Fig. 11B    Fig. 11C
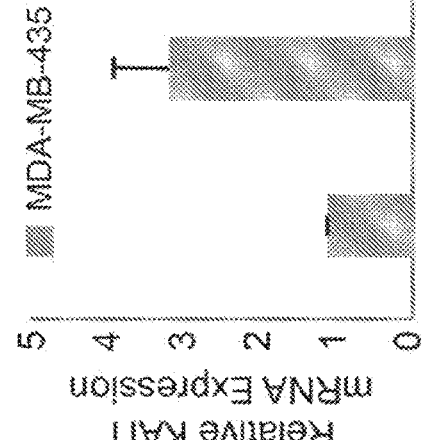
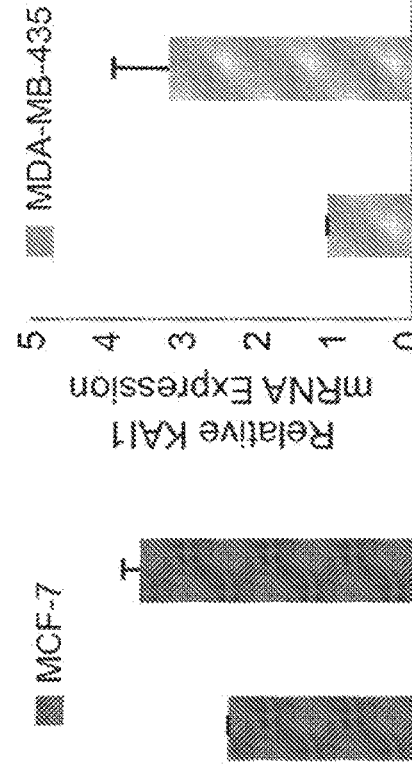
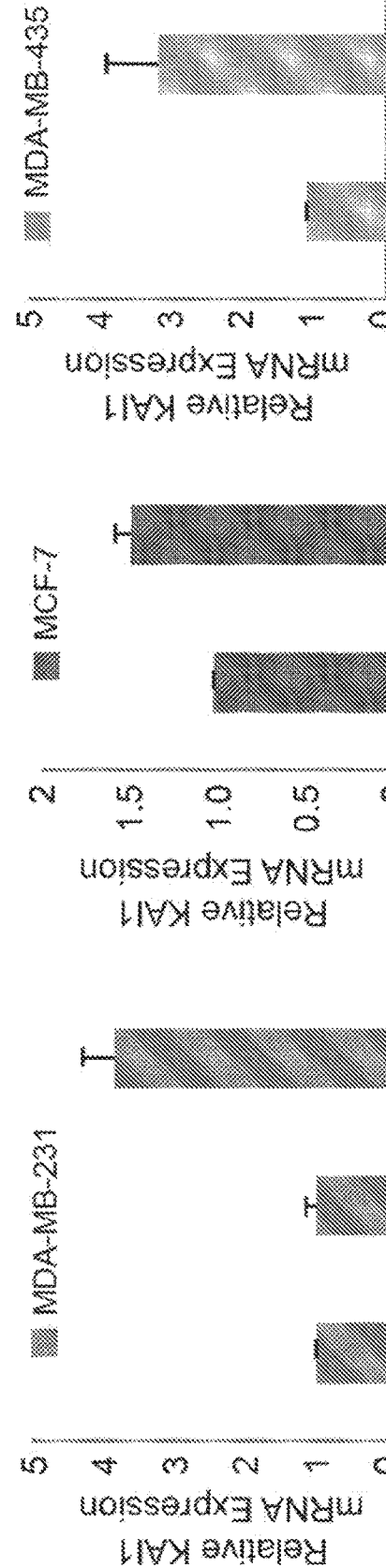
Fig. 12A    Fig. 12B    Fig. 12C

SEQUENCE LISTING

```
<160> NUMBER OF SEQ ID NOS: 50

<210> SEQ ID NO 1
<211> LENGTH: 801
<212> TYPE: DNA
<213> ORGANISM: Homo sapiens
<220> FEATURE:
<221> NAME/KEY: misc_feature
<223> OTHER INFORMATION: Sense KAI1 ORF

<400> SEQUENCE: 1
atgggctcag cctgtatcaa agtcaccaaa tactttctct tcctcttcaa cttgatcttc      60
tttatcctgg gcgcagtgat cctgggcttc ggggtgtgga tcctggccga caagagcagt     120
ttcatctctg tcctgcaaac ctcctccagc tcgcttagga tggggccta tgtcttcatc      180 ggcgtggggg cagtcactat gctcatgggc ttcctgggct gcatcggcgc cgtcaacgag     240
gtccgctgcc tgctggggct gtactttgct ttcctgctcc tgatcctcat tgcccaggtg     300
acggccgggg ccctcttcta cttcaacatg ggcaagctga agcaggagat gggcggcatc     360
gtgactgagc tcattcgaga ctacaacagc agtcgcgagg acagcctgca ggatgcctgg     420
gactacgtgc aggctcaggt gaagtgctgc ggctgggtca gcttctacaa ctggacagac     480
aacgctgagc tcatgaatcg ccctgaggtc acctacccct gttcctgcga agtcaagggg     540
gaagaggaca acagcctttc tgtgaggaag ggcttctgcg aggcccccgg caacaggacc     600
cagagtggca accaccctga ggactggcct gtgtaccagg agggctgcat ggagaaggtg     660
caggcgtggc tgcaggagaa cctgggcatc atcctcggcg tgggcgtggg tgtggccatc     720
atcgagctcc tggggatggt cctgtccatc tgcttgtgcc ggcacgtcca ttccgaagac     780
tacagcaagg tccccaagta c                                              801

<210> SEQ ID NO 2
<211> LENGTH: 801
<212> TYPE: DNA
<213> ORGANISM: Homo sapiens
<220> FEATURE:
<221> NAME/KEY: misc_feature
<223> OTHER INFORMATION: Anti-Sense KAI1 ORF

<400> SEQUENCE: 2
gtacttgggg accttgctgt agtcttcgga atggacgtgc cggcacaagc agatggacag      60
gaccatcccc aggagctcga tgatggccac acccacgccc acgccgagga tgatgcccag     120
gttctcctgc agccacgcct gcaccttctc catgcagccc tcctggtaca caggccagtc     180
ctcagggtgg ttgccactct gggtcctgtt gccggggggcc tcgcagaagc ccttcctcac     240
agaaaggctg ttgtcctctt ccccttgac ttcgcaggaa caggggtagg tgacctcagg      300
gcgattcatg agctcagcgt tgtctgtcca gttgtagaag ctgacccagc cgcagcactt     360
cacctgagcc tgcacgtagt cccaggcatc ctgcaggctg tcctcgcgac tgctgttgta     420
gtctcgaatg agctcagtca cgatgccgcc catctcctgc ttcagcttgc ccatgttgaa     480
```

```
gtagaagagg gccccggccg tcacctgggc aatgaggatc aggagcagga aagcaaagta    540
cagccccagc aggcagcgga cctcgttgac ggcgccgatg cagcccagga agcccatgag    600
catagtgact gccccacgc cgatgaagac ataggccccc atcctaagcg agctggagga     660
ggtttgcagg acagagatga aactgctctt gtcggccagg atccacaccc cgaagcccag    720
gatcactgcg cccaggataa agaagatcaa gttgaagagg aagagaaagt atttggtgac    780
tttgatacag gctgagccca t                                              801
```

<210> SEQ ID NO 3
<211> LENGTH: 22
<212> TYPE: DNA
<213> ORGANISM: Artificial Sequence
<220> FEATURE:
<223> OTHER INFORMATION: shRNA non-silencing

<400> SEQUENCE: 3

```
atctcgcttg ggcgagagta ag                                             22
```

<210> SEQ ID NO 4
<211> LENGTH: 97
<212> TYPE: DNA
<213> ORGANISM: Artificial Sequence
<220> FEATURE:
<223> OTHER INFORMATION: shRNA-1, directed against KAI1 as-lncRNA (T for
      U)
<220> FEATURE:
<221> NAME/KEY: misc_feature
<223> OTHER INFORMATION: Synthetic

<400> SEQUENCE: 4

```
tgctgttgac agtgagcgca caactcatgg gtactctcgt tagtgaagcc acagatgtaa    60
cgagagtacc catgagttgt gtgcctactg cctcgga                             97
```

<210> SEQ ID NO 5
<211> LENGTH: 21
<212> TYPE: DNA
<213> ORGANISM: Artificial Sequence
<220> FEATURE:
<223> OTHER INFORMATION: target-like sequence (the actual sequence is
      present in the 792 bp long KAI1 as-lncRNA)
<220> FEATURE:
<221> NAME/KEY: misc_feature
<223> OTHER INFORMATION: Synthetic

<400> SEQUENCE: 5

```
acaactcatg ggtactctcg t                                              21
```

<210> SEQ ID NO 6
<211> LENGTH: 21
<212> TYPE: DNA
<213> ORGANISM: Artificial Sequence
<220> FEATURE:
<223> OTHER INFORMATION: inverted repeat (guide) sequence of the
      target-like sequence of SEQ ID NO. 5
<220> FEATURE:
<221> NAME/KEY: misc_feature
<223> OTHER INFORMATION: Synthetic

<400> SEQUENCE: 6

```
acgagagtac ccatgagttg t                                              21
```

<210> SEQ ID NO 7
<211> LENGTH: 19
<212> TYPE: DNA
<213> ORGANISM: Artificial Sequence

```
<220> FEATURE:
<223> OTHER INFORMATION: hairpin loop within shRNA-1
<220> FEATURE:
<221> NAME/KEY: misc_feature
<223> OTHER INFORMATION: Synthetic

<400> SEQUENCE: 7
tagtgaagcc acagatgta                                                   19

<210> SEQ ID NO 8
<211> LENGTH: 19
<212> TYPE: DNA
<213> ORGANISM: Artificial Sequence
<220> FEATURE:
<223> OTHER INFORMATION: Flanking sequence within shRNA-1
<220> FEATURE:
<221> NAME/KEY: misc_feature
<223> OTHER INFORMATION: Synthetic

<400> SEQUENCE: 8
tgctgttgac agtgagcgc                                                   19

<210> SEQ ID NO 9
<211> LENGTH: 17
<212> TYPE: DNA
<213> ORGANISM: Artificial Sequence
<220> FEATURE:
<223> OTHER INFORMATION: Flanking sequence within shRNA-1
<220> FEATURE:
<221> NAME/KEY: misc_feature
<223> OTHER INFORMATION: Synthetic

<400> SEQUENCE: 9
gtgcctactg cctcgga                                                     17

<210> SEQ ID NO 10
<211> LENGTH: 40
<212> TYPE: DNA
<213> ORGANISM: Artificial Sequence
<220> FEATURE:
<223> OTHER INFORMATION: Primer used to amplify shRNA-1
<220> FEATURE:
<221> NAME/KEY: misc_feature
<223> OTHER INFORMATION: Synthetic

<400> SEQUENCE: 10
cagaaggctc gagaaggtat attgctgttg acagtgagcg                            40

<210> SEQ ID NO 11
<211> LENGTH: 35
<212> TYPE: DNA
<213> ORGANISM: Artificial Sequence
<220> FEATURE:
<223> OTHER INFORMATION: Primer used to amplify shRNA-1
<220> FEATURE:
<221> NAME/KEY: misc_feature
<223> OTHER INFORMATION: Synthetic

<400> SEQUENCE: 11
ctaaagtagc cccttgaatt ccgaggcagt aggca                                 35

<210> SEQ ID NO 12
<211> LENGTH: 22
<212> TYPE: DNA
<213> ORGANISM: Artificial Sequence
<220> FEATURE:
<223> OTHER INFORMATION: KAI1 ORF Forward
<220> FEATURE:
<221> NAME/KEY: misc_feature
```

<223> OTHER INFORMATION: Synthetic

<400> SEQUENCE: 12
atgggctcag cctgtatcaa ag                                              22

<210> SEQ ID NO 13
<211> LENGTH: 22
<212> TYPE: DNA
<213> ORGANISM: Artificial Sequence
<220> FEATURE:
<223> OTHER INFORMATION: KAI1 ORF Reverse
<220> FEATURE:
<221> NAME/KEY: misc_feature
<223> OTHER INFORMATION: Synthetic

<400> SEQUENCE: 13
tcagtacttg gggaccttgc tg                                              22

<210> SEQ ID NO 14
<211> LENGTH: 18
<212> TYPE: DNA
<213> ORGANISM: Artificial Sequence
<220> FEATURE:
<223> OTHER INFORMATION: AgeI-SnaBI-EcoRI adapter upper strand
<220> FEATURE:
<221> NAME/KEY: misc_feature
<223> OTHER INFORMATION: Synthetic

<400> SEQUENCE: 14
ccggtgtacg tacgtacg                                                   18

<210> SEQ ID NO 15
<211> LENGTH: 14
<212> TYPE: DNA
<213> ORGANISM: Artificial Sequence
<220> FEATURE:
<223> OTHER INFORMATION: 5' to 3' EcoRI-SnaBI-AgeI adapter lower strand
<220> FEATURE:
<221> NAME/KEY: misc_feature
<223> OTHER INFORMATION: Synthetic

<400> SEQUENCE: 15
aattcgtacg taca                                                       14

<210> SEQ ID NO 16
<211> LENGTH: 20
<212> TYPE: DNA
<213> ORGANISM: Artificial Sequence
<220> FEATURE:
<223> OTHER INFORMATION: Primer used for determining the orientation of
      the insert (sense or antisense) of KAI1 ORF sequence into TRIPZ
<220> FEATURE:
<221> NAME/KEY: misc_feature
<223> OTHER INFORMATION: Synthetic

<400> SEQUENCE: 16
cgtatgtcga ggtaggcgtg                                                 20

<210> SEQ ID NO 17
<211> LENGTH: 78
<212> TYPE: RNA
<213> ORGANISM: Artificial Sequence
<220> FEATURE:
<223> OTHER INFORMATION: 78 bp sequence mutual to all four transcripts
<220> FEATURE:
<221> NAME/KEY: misc_feature
<223> OTHER INFORMATION: Synthetic

<400> SEQUENCE: 17

```
ccagccucag guccugaguc acaggcuuga gcugcccag cuugccugga cuggccccug    60
gggaaguagc ccagaaca                                                 78

<210> SEQ ID NO 18
<211> LENGTH: 60
<212> TYPE: DNA
<213> ORGANISM: Artificial Sequence
<220> FEATURE:
<223> OTHER INFORMATION: KAI1- shRNA-1 upper (for insertion into SHC203)
<220> FEATURE:
<221> NAME/KEY: misc_feature
<223> OTHER INFORMATION: Synthetic

<400> SEQUENCE: 18
cccggacaac tcatgggtac tctcgtctcg agacgagagt acccatgagt tgttttttgt    60

<210> SEQ ID NO 19
<211> LENGTH: 60
<212> TYPE: DNA
<213> ORGANISM: Artificial Sequence
<220> FEATURE:
<223> OTHER INFORMATION: KAI1- shRNA-1 lower (for insertion into SHC203)
<220> FEATURE:
<221> NAME/KEY: misc_feature
<223> OTHER INFORMATION: Synthetic

<400> SEQUENCE: 19
aacaaaaaac aactcatggg tactctcgtc tcgagacgag agtacccatg agttgtccgg    60

<210> SEQ ID NO 20
<211> LENGTH: 1198
<212> TYPE: DNA
<213> ORGANISM: Artificial Sequence
<220> FEATURE:
<223> OTHER INFORMATION: Sense KAI1 promoter-enhancer 1198
<220> FEATURE:
<221> NAME/KEY: misc_feature
<223> OTHER INFORMATION: Synthetic

<400> SEQUENCE: 20
gtcagctgca caggtgaatg cccctggtca ttaaccaggt aatctgcctg aggctagtcc    60
tctggagcct gggagggcag agggctggga cgcagggtgg gcaccgcagc cacctagaga   120
gctcttgcag cccacctcaa ttttgggcca cttttttcttc agggagaaag ccagctttga   180
gggcttaggc ccacagcccc tcctgccact attctcatca cccacacct cctccctcac    240 ctcaggcagc tgctgggcac tgccccagca ctggttgttc tgggctactt ccccagggge   300 cagtccaggc aagctggggc agctcaagcc tgtgactcag gacctgaggc tggatcccgc   360
tcacgcccgc ctccatgaga ttcagagccc tcgacttccc ttctctgagc cttaaactgc   420
gcattagtaa aataggcgca acgagagtac ccatgagttg tgggaattca agggctagaa   480
ctgtattcag cgcttggcat agagcctggc ccctggcaag gattcaatca atggtagtca   540
gtattttcaa aaagttcctg ggcccaggcc gcctcctgat agaggcccg acttaggaca    600 caaaccgctc ccacgccgtt cccggcggc accggatac acccgccctg gaatgccagc    660
gtgggggccc cagggctacc cgcccagat gagaggggca gggcaggca ggattaggaa    720 ggcgctgagc ccaggctggt gcggggaggg gcgtggcctc accctactag gccggggga    780 tgggggtgggc tcgaaggaga aagtgaagga ggcgggggcg ctgggagggc ccggaggag   840 accgggagga cgaggtaggc gggagctggg cgggaccgtt aggcagcgcc gtgagtggac    900
agggctggag cggggcgggc ttaatcccca gtgtaacctg ggggcggggc tgccgggata    960
```

```
gaggagagac tccgtagcgg ggcggggcct cagctccagc tgggcccggg ggcgaggctg    1020
gttggggtac ggccatagtg ggcggggcct ggccggcggg agcgcaccgc cttcccaaag    1080
ggctcggggg cggggccggc ggaggggggcg tgtcttctgg gggcggggcc tgccgagtcc    1140
gcggcgttcc ccggctgcag ccgggagggg gccgaggagt gactgagccc cgggctgt     1198
```

<210> SEQ ID NO 21
<211> LENGTH: 1198
<212> TYPE: DNA
<213> ORGANISM: Artificial Sequence
<220> FEATURE:
<223> OTHER INFORMATION: Anti-Sense KAI1 promoter-enhancer 1198
<220> FEATURE:
<221> NAME/KEY: misc_feature
<223> OTHER INFORMATION: Synthetic

<400> SEQUENCE: 21

```
acagcccggg gctcagtcac tcctcggccc cctcccggct gcagccgggg aacgccgcgg    60
actcggcagg ccccgccccc agaagacacg cccctccgc cggccccgcc cccgagccct    120
ttgggaaggc ggtgcgctcc cgccggccag gccccgccca ctatggccgt accccaacca    180
gcctcgcccc cgggcccagc tggagctgag gccccgcccc gctacggagt ctctcctcta    240
tcccggcagc cccgccccca ggttacactg gggattaagc ccgcccccgct ccagccctgt    300 ccactcacgg cgctgcctaa cggtcccgcc cagctcccgc ctaccctgtc ctcccggtct    360
cctcccgggc cctcccagcg cccccgcctc cttcactttc tccttcgagc ccaccccatc    420 cccggccct agtagggtga ggccacgccc ctccccgcac cagcctgggc tcagcgcctt    480
cctaatcctg ccctgccctg ccctctcat ctcgggcggg tagccctggg gccccacgc    540 tggcattcca gggcgggtgt atccgggtgc cgccggggaa cggcgtggga gcggtttgtg    600
tcctaagtcg gggcctctat caggaggcgg cctgggccca ggaactttt gaaaatactg    660 actaccattg attgaatcct tgccaggggc caggctctat gccaagcgct gaatacagtt    720
ctagcccttg aattcccaca actcatgggt actctcgttg cgcctatttt actaatgcgc    780
agtttaaggc tcagagaagg gaagtcgagg gctctgaatc tcatggaggc gggcgtgagc    840
gggatccagc ctcaggtcct gagtcacagg cttgagctgc cccagcttgc ctggactggc    900
ccctggggaa gtagcccaga caaccagtg ctggggcagt gccagcagc tgcctgaggt    960 gagggaggag gtgtggggttg atgagaatag tggcaggagg ggctgtgggc ctaagccctc    1020
aaagctggct ttctccctga agaaaaagtg gcccaaaatt gaggtgggct gcaagagctc    1080
tctaggtggc tgcggtgccc accctgcgtc ccagccctct gccctcccag gctccagagg    1140
actagcctca ggcagattac ctggttaatg accaggggca ttcacctgtg cagctgac    1198
```

<210> SEQ ID NO 22
<211> LENGTH: 23
<212> TYPE: DNA
<213> ORGANISM: Artificial Sequence
<220> FEATURE:
<223> OTHER INFORMATION: Forward primer for sequencing the
    SHC203-shRNA-1 plasmid
<220> FEATURE:
<221> NAME/KEY: misc_feature
<223> OTHER INFORMATION: Synthetic

<400> SEQUENCE: 22

```
tttcttgggt agtttgcagt ttt                                            23
```

```
<210> SEQ ID NO 23
<211> LENGTH: 22
<212> TYPE: DNA
<213> ORGANISM: Artificial Sequence
<220> FEATURE:
<223> OTHER INFORMATION: Reverse primer for sequencing the
      SHC203-shRNA-1 plasmid
<220> FEATURE:
<221> NAME/KEY: misc_feature
<223> OTHER INFORMATION: Synthetic

<400> SEQUENCE: 23
accgtaagtt atgtaacgcg ga                                              22

<210> SEQ ID NO 24
<211> LENGTH: 20
<212> TYPE: DNA
<213> ORGANISM: Artificial Sequence
<220> FEATURE:
<223> OTHER INFORMATION: KAI1 RealTime Forward
<220> FEATURE:
<221> NAME/KEY: misc_feature
<223> OTHER INFORMATION: Synthetic

<400> SEQUENCE: 24
cggcaacagg acccagagtg                                                 20

<210> SEQ ID NO 25
<211> LENGTH: 21
<212> TYPE: DNA
<213> ORGANISM: Artificial Sequence
<220> FEATURE:
<223> OTHER INFORMATION: KAI1 RealTime Reverse
<220> FEATURE:
<221> NAME/KEY: misc_feature
<223> OTHER INFORMATION: Synthetic

<400> SEQUENCE: 25
cggcacaagc agatggacag g                                               21

<210> SEQ ID NO 26
<211> LENGTH: 20
<212> TYPE: DNA
<213> ORGANISM: Artificial Sequence
<220> FEATURE:
<223> OTHER INFORMATION: KAI1 qRT-PCR pair a forward
<220> FEATURE:
<221> NAME/KEY: misc_feature
<223> OTHER INFORMATION: Synthetic

<400> SEQUENCE: 26
caggatgcct gggactacgt                                                 20

<210> SEQ ID NO 27
<211> LENGTH: 20
<212> TYPE: DNA
<213> ORGANISM: Artificial Sequence
<220> FEATURE:
<223> OTHER INFORMATION: KAI1 qRT-PCR pair a reverse
<220> FEATURE:
<221> NAME/KEY: misc_feature
<223> OTHER INFORMATION: Synthetic

<400> SEQUENCE: 27
gacctcaggg cgattcatga                                                 20

<210> SEQ ID NO 28
<211> LENGTH: 20
<212> TYPE: DNA
```

```
<213> ORGANISM: Artificial Sequence
<220> FEATURE:
<223> OTHER INFORMATION: KAI1 qRT-PCR pair b forward
<220> FEATURE:
<221> NAME/KEY: misc_feature
<223> OTHER INFORMATION: Synthetic

<400> SEQUENCE: 28
tctgtgagga agggcttctg                                              20

<210> SEQ ID NO 29
<211> LENGTH: 20
<212> TYPE: DNA
<213> ORGANISM: Artificial Sequence
<220> FEATURE:
<223> OTHER INFORMATION: KAI1 qRT-PCR pair b reverse
<220> FEATURE:
<221> NAME/KEY: misc_feature
<223> OTHER INFORMATION: Synthetic

<400> SEQUENCE: 29
gtacttgggg accttgctgt                                              20

<210> SEQ ID NO 30
<211> LENGTH: 20
<212> TYPE: DNA
<213> ORGANISM: Artificial Sequence
<220> FEATURE:
<223> OTHER INFORMATION: KAI1 qRT-PCR pair c forward
<220> FEATURE:
<221> NAME/KEY: misc_feature
<223> OTHER INFORMATION: Synthetic

<400> SEQUENCE: 30
ggagaacctg ggcatcatcc                                              20

<210> SEQ ID NO 31
<211> LENGTH: 20
<212> TYPE: DNA
<213> ORGANISM: Artificial Sequence
<220> FEATURE:
<223> OTHER INFORMATION: KAI1 qRT-PCR pair c reverse
<220> FEATURE:
<221> NAME/KEY: misc_feature
<223> OTHER INFORMATION: Synthetic

<400> SEQUENCE: 31
ttggggacct tgctgtagtc                                              20

<210> SEQ ID NO 32
<211> LENGTH: 18
<212> TYPE: DNA
<213> ORGANISM: Artificial Sequence
<220> FEATURE:
<223> OTHER INFORMATION: KAI1 RT 2
<220> FEATURE:
<221> NAME/KEY: misc_feature
<223> OTHER INFORMATION: Synthetic

<400> SEQUENCE: 32
tcagcgcttg gcatagag                                                18

<210> SEQ ID NO 33
<211> LENGTH: 20
<212> TYPE: DNA
<213> ORGANISM: Artificial Sequence
<220> FEATURE:
<223> OTHER INFORMATION: KAI1 RT 3
<220> FEATURE:
```

<221> NAME/KEY: misc_feature
<223> OTHER INFORMATION: Synthetic

<400> SEQUENCE: 33
gcactggttg ttctgggcta                                          20

<210> SEQ ID NO 34
<211> LENGTH: 20
<212> TYPE: DNA
<213> ORGANISM: Artificial Sequence
<220> FEATURE:
<223> OTHER INFORMATION: KAI1 RT 5
<220> FEATURE:
<221> NAME/KEY: misc_feature
<223> OTHER INFORMATION: Synthetic

<400> SEQUENCE: 34
caacggtgtg ttgtgagagg                                          20

<210> SEQ ID NO 35
<211> LENGTH: 19
<212> TYPE: DNA
<213> ORGANISM: Artificial Sequence
<220> FEATURE:
<223> OTHER INFORMATION: KAI1 Promoter 3 Forward
<220> FEATURE:
<221> NAME/KEY: misc_feature
<223> OTHER INFORMATION: Synthetic

<400> SEQUENCE: 35
cctgatagag gccccgact                                           19

<210> SEQ ID NO 36
<211> LENGTH: 18
<212> TYPE: DNA
<213> ORGANISM: Artificial Sequence
<220> FEATURE:
<223> OTHER INFORMATION: KAI1 Promoter 3 Reverse
<220> FEATURE:
<221> NAME/KEY: misc_feature
<223> OTHER INFORMATION: Synthetic

<400> SEQUENCE: 36
attccagggc gggtgtat                                            18

<210> SEQ ID NO 37
<211> LENGTH: 18
<212> TYPE: DNA
<213> ORGANISM: Artificial Sequence
<220> FEATURE:
<223> OTHER INFORMATION: KAI1 RT2 reverse complement
<220> FEATURE:
<221> NAME/KEY: misc_feature
<223> OTHER INFORMATION: Synthetic

<400> SEQUENCE: 37
ctctatgcca agcgctga                                            18

<210> SEQ ID NO 38
<211> LENGTH: 20
<212> TYPE: DNA
<213> ORGANISM: Artificial Sequence
<220> FEATURE:
<223> OTHER INFORMATION: KAI1 RT3 reverse complement
<220> FEATURE:
<221> NAME/KEY: misc_feature
<223> OTHER INFORMATION: Synthetic

<400> SEQUENCE: 38

```
tagcccagaa caaccagtgc                                                    20
```

<210> SEQ ID NO 39
<211> LENGTH: 60
<212> TYPE: DNA
<213> ORGANISM: Artificial Sequence
<220> FEATURE:
<223> OTHER INFORMATION: KAI1 60 mer nc
<220> FEATURE:
<221> NAME/KEY: misc_feature
<223> OTHER INFORMATION: Synthetic

<400> SEQUENCE: 39

```
ctctgagcct taaactgcgc attagtaaaa taggcgcaac gagagtaccc atgagttgtg        60
```

<210> SEQ ID NO 40
<211> LENGTH: 267
<212> TYPE: PRT
<213> ORGANISM: Homo sapiens
<220> FEATURE:
<221> NAME/KEY: MISC_FEATURE
<223> OTHER INFORMATION: AA seq. of KAI1 (267 aa) GenBank: AAC51205.1

<400> SEQUENCE: 40

```
Met Gly Ser Ala Cys Ile Lys Val Thr Lys Tyr Phe Leu Phe Leu Phe
1               5                   10                  15

Asn Leu Ile Phe Phe Ile Leu Gly Ala Val Ile Leu Gly Phe Gly Val
            20                  25                  30

Trp Ile Leu Ala Asp Lys Ser Ser Phe Ile Ser Val Leu Gln Thr Ser
        35                  40                  45

Ser Ser Ser Leu Arg Met Gly Ala Tyr Val Phe Ile Gly Val Gly Ala
    50                  55                  60

Val Thr Met Leu Met Gly Phe Leu Gly Cys Ile Gly Ala Val Asn Glu
65                  70                  75                  80

Val Arg Cys Leu Leu Gly Leu Tyr Phe Ala Phe Leu Leu Leu Ile Leu
                85                  90                  95

Ile Ala Gln Val Thr Ala Gly Ala Leu Phe Tyr Phe Asn Met Gly Lys
            100                 105                 110

Leu Lys Gln Glu Met Gly Gly Ile Val Thr Glu Leu Ile Arg Asp Tyr
        115                 120                 125

Asn Ser Ser Arg Glu Asp Ser Leu Gln Asp Ala Trp Asp Tyr Val Gln
    130                 135                 140

Ala Gln Val Lys Cys Cys Gly Trp Val Ser Phe Tyr Asn Trp Thr Asp
145                 150                 155                 160

Asn Ala Glu Leu Met Asn Arg Pro Glu Val Thr Tyr Pro Cys Ser Cys
                165                 170                 175

Glu Val Lys Gly Glu Glu Asp Asn Ser Leu Ser Val Arg Lys Gly Phe
            180                 185                 190

Cys Glu Ala Pro Gly Asn Arg Thr Gln Ser Gly Asn His Pro Glu Asp
        195                 200                 205

Trp Pro Val Tyr Gln Glu Gly Cys Met Glu Lys Val Gln Ala Trp Leu
    210                 215                 220

Gln Glu Asn Leu Gly Ile Ile Leu Gly Val Gly Val Gly Val Ala Ile
225                 230                 235                 240

Ile Glu Leu Leu Gly Met Val Leu Ser Ile Cys Leu Cys Arg His Val
                245                 250                 255

His Ser Glu Asp Tyr Ser Lys Val Pro Lys Tyr
            260                 265
```

<210> SEQ ID NO 41
<211> LENGTH: 18
<212> TYPE: DNA
<213> ORGANISM: Artificial Sequence
<220> FEATURE:
<223> OTHER INFORMATION: HPRT-1 qRT-PCR Forward
<220> FEATURE:
<221> NAME/KEY: misc_feature
<223> OTHER INFORMATION: Synthetic

<400> SEQUENCE: 41
gccctggcgt cgtgatta                                                 18

<210> SEQ ID NO 42
<211> LENGTH: 21
<212> TYPE: DNA
<213> ORGANISM: Artificial Sequence
<220> FEATURE:
<223> OTHER INFORMATION: HPRT-1 qRT-PCR Reverse
<220> FEATURE:
<221> NAME/KEY: misc_feature
<223> OTHER INFORMATION: Synthetic

<400> SEQUENCE: 42
ccctttccaa atcctcagca t                                             21

<210> SEQ ID NO 43
<211> LENGTH: 22
<212> TYPE: DNA
<213> ORGANISM: Artificial Sequence
<220> FEATURE:
<223> OTHER INFORMATION: TBP Forward
<220> FEATURE:
<221> NAME/KEY: misc_feature
<223> OTHER INFORMATION: Synthetic

<400> SEQUENCE: 43
cacaggagcc aagagtgaag aa                                            22

<210> SEQ ID NO 44
<211> LENGTH: 24
<212> TYPE: DNA
<213> ORGANISM: Artificial Sequence
<220> FEATURE:
<223> OTHER INFORMATION: TBP Reverse
<220> FEATURE:
<221> NAME/KEY: misc_feature
<223> OTHER INFORMATION: Synthetic

<400> SEQUENCE: 44
aagaacttag ctggaaaacc caac                                          24

<210> SEQ ID NO 45
<211> LENGTH: 19
<212> TYPE: DNA
<213> ORGANISM: Artificial Sequence
<220> FEATURE:
<223> OTHER INFORMATION: GFPtpz qRT-PCR forward
<220> FEATURE:
<221> NAME/KEY: misc_feature
<223> OTHER INFORMATION: Synthetic

<400> SEQUENCE: 45
gttcagcgtg tccgcgagg                                                19

<210> SEQ ID NO 46
<211> LENGTH: 792

```
<212> TYPE: RNA
<213> ORGANISM: Homo sapiens
<220> FEATURE:
<221> NAME/KEY: misc_feature
<223> OTHER INFORMATION: Sequence of the 792 bp lncRNA Suppressor of
      KAI1 in breast cancer (SKA1BC)

<400> SEQUENCE: 46
caccagccug ggcucagcgc cuuccuaauc cugcccugcc cugccccucu caucucgggc    60
ggguagcccu ggggccccca cgcuggcauu ccagggcggg uguauccggg ugccgccggg   120
gaacggcgug ggagcgguuu guguccuaag ucggggccuc uaucaggagg cggccugggc   180
ccaggaacuu uuugaaaaua cugacuacca uugauugaau ccuugccagg ggccaggcuc   240
uaugccaagc gcugaauaca guucuagccc uugaauuccc acaacucaug gguacucucg   300
uugcgccuau uuuacuaaug cgcaguuuaa ggcucagaga agggaagucg agggcucuga   360
aucucaugga ggcgggcgug agcgggaucc agccucaggu ccugagucac aggcuugagc   420
ugccccagcu ugccuggacu ggccccuggg gaaguagccc agaacaacca gugcugggc    480 agugcccagc agcugccuga ggugagggag gaggugu ggg uugaugagaa uaguggcagg   540
aggggcugug ggccuaagcc cucaaagcug gcuuucuccc ugaagaaaaa gugggcccaaa  600 auugagugg gcugcaagag cucucuaggu ggcugcggug cccacccugc gucccagccc   660
ucugcccucc caggcuccag aggacuagcc ucaggcagau uaccugguua augaccaggg   720
gcauucaccu gugcagcuga caaagcucuu ucacuuccau uaucacaaug uccucucaca   780
acacaccguu gu                                                       792

<210> SEQ ID NO 47
<211> LENGTH: 21
<212> TYPE: DNA
<213> ORGANISM: Artificial Sequence
<220> FEATURE:
<223> OTHER INFORMATION: Broad-1 shRNA
<220> FEATURE:
<221> NAME/KEY: misc_feature
<223> OTHER INFORMATION: Synthetic

<400> SEQUENCE: 47
ctctatgcca agcgctgaat a                                              21

<210> SEQ ID NO 48
<211> LENGTH: 21
<212> TYPE: DNA
<213> ORGANISM: Artificial Sequence
<220> FEATURE:
<223> OTHER INFORMATION: Broad-2 shRNA
<220> FEATURE:
<221> NAME/KEY: misc_feature
<223> OTHER INFORMATION: Synthetic

<400> SEQUENCE: 48
tttactaatg cgcagtttaa g                                              21

<210> SEQ ID NO 49
<211> LENGTH: 78
<212> TYPE: DNA
<213> ORGANISM: Artificial Sequence
<220> FEATURE:
<223> OTHER INFORMATION: DNA Sequence encoding a segment mutual to all
      four transcripts, known as the KAI1 enhancer with its
      transcription proteins binding sites
<220> FEATURE:
<221> NAME/KEY: misc_feature
<223> OTHER INFORMATION: Synthetic
```

```
<400> SEQUENCE: 49
tgttctgggc tacttcccca ggggccagtc caggcaagct ggggcagctc aagcctgtga      60
ctcaggacct gaggctgg                                                   78

<210> SEQ ID NO 50
<211> LENGTH: 1607
<212> TYPE: DNA
<213> ORGANISM: Homo sapiens
<220> FEATURE:
<221> NAME/KEY: misc_feature
<223> OTHER INFORMATION: Human metastasis suppressor (KAI1) mRNA,
      complete cds GenBank: U20770.1

<400> SEQUENCE: 50
ccgactgagg cacgagcggg tgacgctggg cctgcagcgc ggagcagaaa gcagaacccg      60
cagagtcctc cctgctgctg tgtggacgac acgtgggcac aggcagaagt gggccctgtg     120
accagctgca ctggtttcgt ggaaggaagc tccaggactg gcgggatggg ctcagcctgt     180
atcaaagtca ccaaatactt tctcttcctc ttcaacttga tcttctttat cctgggcgca     240
gtgatcctgg gcttcggggt gtggatcctg gccgacaaga gcagtttcat ctctgtcctg     300
caaacctcct ccagctcgct taggatgggg gcctatgtct tcatcggcgt gggggcagtc     360
actatgctca tgggcttcct gggctgcatc ggcgccgtca acgaggtccg ctgcctgctg     420
gggctgtact ttgctttcct gctcctgatc ctcattgccc aggtgacggc cggggccctc     480
ttctacttca acatgggcaa gctgaagcag gagatgggcg gcatcgtgac tgagctcatt     540
cgagactaca acagcagtcg cgaggacagc ctgcaggatg cctgggacta cgtgcaggct     600
caggtgaagt gctgcggctg ggtcagcttc tacaactgga cagacaacgc tgagctcatg     660
aatcgccctg aggtcaccta cccctgttcc tgcgaagtca aggggaaga ggacaacagc     720 ctttctgtga ggaagggctt ctgcgaggcc cccggcaaca ggacccagag tggcaaccac     780
cctgaggact ggcctgtgta ccaggagggc tgcatggaga aggtgcaggc gtggctgcag     840
gagaacctgg gcatcatcct cggcgtgggc gtgggtgtgg ccatcatcga gctcctgggg     900
atggtcctgt ccatctgctt gtgccggcac gtccattccg aagactacag caaggtcccc     960
aagtactgag gcagctgcta tccccatctc cctgcctggc ccccaacctc agggctccca    1020
ggggtctccc tggctccctc ctccaggcct gcctcccact tcactgcgaa gaccctcttg    1080
cccaccctga ctgaaagtag ggggcttct ggggcctagc gatctctcct ggcctatccg    1140
ctgccagcct tgagccctgg ctgttctgtg gttcctctgc tcaccgccca tcagggttct    1200
cttatcaact cagagaaaaa tgctccccac agcgtccctg gcgcaggtgg gctggacttc    1260
tacctgccct caagggtgtg tatattgtat agggcaact gtatgaaaaa ttggggagga    1320
gggggccggg cgcggtgctc acgcctgtaa tcccagcact ttgggaggcc gaggcgggtg    1380
gatcacgagg tcaggagatc gagaccatcc tggctaacat ggtgaaaccc cgtctctact    1440
aaaaatacaa aaaaattta gccgggcgcg gtggcgggca cctgtagtcc cagctacttg    1500
ggaggctgag gcaggagaat ggtgtgaacc cgggagcgga ggttgcagtg agctgagatc    1560
gtgctactgc actccagcct gggggacaga aagagactcc gtctcaa                 1607
```

MODULATORS OF HUMAN KAI1 METASTASIS SUPPRESSOR GENE, METHODS AND USES THEREOF

FIELD OF THE INVENTION

The present disclosure generally relates to modulators of cancer and tumor metastasis. More specifically the present disclosure pertains to modulators of KAI1 as-lncRNA also referred to herein as SKAI1BC, an antisense long non-coding RNA which was found to be an epigenetic suppressor of the metastasis suppressor gene KAI1/cluster of differentiation 82 (CD82), compositions, methods and uses thereof for decreasing proliferation, metastasis and invasion of cancer cells.

BACKGROUND ART

References considered to be relevant as background to the presently disclosed subject matter are listed below:
Albrecht, Anne-Susann and Ulf Andersson Ørom. (2016). "Bidirectional Expression of Long ncRNA/protein-Coding Gene Pairs in Cancer." *Briefings in functional genomics* 15 (3): 167-173.
Avivi Shira, Mor Amir, Dotan Iris, Tzadok Sivan, Kanter Itamar, Kinor Noa, Canaani Dan, and Shav-Tal Yaron (2017). *PNAS USA* 114: E8837-88460.
Chodroff, Rebecca A. et al. (2010). *Genome biology* 11(7): R72.
Cohen Z. R., Ramishetti S., Fehes-Yaloz N., Goldsmith M., Wohl., Zibly Z., and Peer D. (2015). *ACS Nano* 9: 1581-1591.
Duttke, Sascha H. C. et al. (2015). *Molecular cell* 57(4): 674-84.
Feng J. et al., (2015). *Cancer Metastasis Rev.* 34: 619-632.
Holen I, Speirs V, Morrissey B, Blyth K (2017). *Dis Model Mech.* 10: 359-371.
Iyer M. K. et al., (2015). *Nat. Genet.* 47: 199-208.
Lee, Ji Hee, Young-Woo Seo, Sei Ryun Park, Young Jin Kim, and Kyung Keun Kim. (2003). *Cancer research* 63(21): 7247-55.
Malik, Faraz Arshad, Andrew J. Sanders, Mahmood A. Kayani, and Wen G. Jiang. (2009). *Cancer genomics & proteomics* 6(4): 205-13.
Marques, Ana C. and Chris P. Ponting. (2009). *Genome biology* 10(11): R124.
Marreiros, Alexandra, Robert Czolij, Gina Yardley, Merlin Crossley, and Paul Jackson. (2003). *Gene* 302(1-2): 155-64.
Martianov, Igor, Aroul Ramadass, Ana Serra Barros, Natalie Chow, and Alexandre Akoulitchev. (2007). *Nature* 445 (7128): 666-70.
Morris, Kevin V, Sharon Santoso, Anne-Marie Turner, Chiara Pastori, and Peter G. Hawkins. (2008). *PLoS genetics* 4(11): e1000258.
Morris K. V. and Mattick J. S. (2014). *Nat. Rev. Genet.* 15: 423-437.
Orom, Ulf Andersson and Ramin Shiekhattar. (2011). *Trends in genetics: TIG* 27(10):433-39.
Osato, Naoki, Yoshiyuki Suzuki, Kazuho Ikeo, and Takashi Gojobori. (2007). *Genetics* 176(2): 1299-1306.
Schmitt A. H. and Chang H. Y. (2016). *Cancer Cell* 29: 452-463.
Wang, Xiangting et al. (2008). *Nature* 454(7200): 126-30.
Yang, X. et al. (2000). *Clinical cancer research: an official journal of the American Association for Cancer Research* 6(9): 3424-29.
Yu, Wenqiang et al. (2008). *Nature* 451(7175): 202-6.
Zhang, Fan, Liang Zhang, and Caiguo Zhang. (2016). *Tumour biology: the journal of the International Society for Oncodevelopmental Biology and Medicine* 37(1): 163-75.

Acknowledgement of the above references herein is not to be inferred as meaning that these are in any way relevant to the patentability of the presently disclosed subject matter.

BACKGROUND OF THE INVENTION

Classically, mostly proteins were considered to be involved in cellular functions. However, research in the past ten years caused this paradigm to totter. Large-scale sequencing of cDNA libraries elucidated many noncoding RNAs (ncRNAs), besides the already known ribosomal RNAs (rRNAs), transfer RNAs (tRNAs), nuclear RNAs and nucleolar RNAs. Prominent among this newly identified group being noncoding RNAs longer than 200 nucleotides, named accordingly long noncoding RNAs (lncRNAs). Although the vast majority of annotated lncRNAs remain under-explored, more and more regulatory functions of RNA transcripts have been elucidated, suggesting that lncRNA play an important role in cellular processes (reviewed by Morris and Mattick, 2014; Schmitt and Chang, 2016).

Contrary to short ncRNAs (<200 nts), lncRNAs are not always highly conserved but can be enriched in conserved sequence motifs (Chodroff et al., 2010; Iyer et al., 2015). Sequence conservation among different species can even implicate biological functions in mammals. It is known that the transcription of lncRNA can regulate the expression of genes in close proximity (cis-acting) or target distant transcriptional activators/suppressors (trans-acting). The majority of intergenic lncRNAs are expressed at much lower levels compared with protein coding mRNA transcripts and are tissue specific (Marques and Ponting, 2009). If promoters of the lncRNA and protein coding gene lie in close proximity, a co-regulation may occur via "transcriptional interference", when the transcription machinery elongates through a promoter sequence and suppresses the initiation of another transcriptional event (Osato et al., 2007; Martianov et al., 2007). Another mechanism has been reported by Wang et al., (2008) in which a lncRNA is induced by ionizing radiation upstream of the cyclin D1 (CCND1) promoter. The lncRNA transcript recruits a RNA-binding protein that inhibits the histone acetyltransferases through allosteric interactions, resulting in decreased CCND1 expression (Wang et al., 2008). Many experiments have shown that lncRNA can also act on distal genomic locations (Ørom and Shiekhattar, 2011).

Curiously, only a small percentage of cancer causations is attributed to variations of protein coding sequences, while more frequent being changes in gene expression levels (Zhang, Zhang, and Zhang, 2016). Recently, growing evidence indicate that lncRNAs are involved in tumorigenesis by showing aberrant expression in cancer cells in comparison to healthy tissue cells (Zhang, Zhang, and Zhang, 2016). Therefore, lncRNAs emerge as new players in cancer, showing potential roles in oncogenic and tumor suppressive pathways (Schmitt and Chang, 2016). Two early on examples has to do with the tumor suppressors p15 and p21 and their promoters' spanning lncRNAs (p15-AS; p21-AS). Ectopic expression of siRNAs against natural promoter spanning antisense lncRNAs of p15 and p21, the transcriptionally silenced tumor suppressor genes have been re-activated, which indicates oncogenic features of these antisense lncRNAs (Yu et al., 2008; Morris et al., 2008, respectively). These latter results point toward the potential of promoter-directed shRNAs to activate2c gene expression of tumor/metastasis suppressor genes, silenced by promoter spanning as-lncRNAs. Divergent transcription that results in a sense mRNA and an antisense lncRNA (as-lncRNA) has been observed in ~50-80% of human protein coding gene promoters (Duttke et al., 2015). These bi-directional promoters are associated among others with neuronal functions, regulation of tumor suppressors and oncogenes (Albrecht and Ørom, 2016). Two other prominent examples of breast cancer linked lncRNAs are represented by HOTAIR and MALAT1 (Schmitt and Chang, 2016). HOTAIR is an lncRNA acting as a scaffold molecule by interacting with a chromatin modification complex that enables the HOXD gene silencing in trans. In primary and metastatic breast cancer cells, the HOTAIR level is up to hundreds fold higher than in normal breast epithelia. This leads to transcription silencing of metastasis suppressor genes and results in tumor metastasis (Schmitt and Chang, 2016). The MALAT1 (Metastasis-associated lung adenocarcinoma transcript 1), an evolutionary conserved abundant nuclear lncRNA promotes cancer cell proliferation and metastasis in non-small cell lung carcinoma (Schmitt and Chang, 2016).

The KAI1 metastasis suppressor gene (also known as CD82 or Tspan27), is located on human chromosome 11p11.2 and encodes for a 267 amino acid transmembrane protein that belongs to the tetraspanin family. According to the Ensembl gene browser, the KAI1 transcript can be found in 14 splice variants of which only the main variant leads to translation of the functional protein. Members of the tetraspanin protein family are characterized by four transmembrane domains and short intracellular N- and C-termini. The predicted molecular weight of the KAI1 protein varies from 25-90 kDa due to varying degrees of glycosylation. Post-translational modifications of KAI1, such as glycosylation or palmitoylation, are common events.

The human KAI1 promoter is very GC rich (68% GC). In myeloma cells low KAI1 expression has been described to be associated with a hypermethylated CpG island in the promoter region, whereas in pancreatic cancer cells the CpG island is only partly methylated. The TATA- and CCAAT-box less promoter has three known regulatory regions: an enhancer region, a negative regulatory region and a minimal promoter region. The 76-78 bp long enhancer region harbors binding sites for the transcription initiation proteins AP1, AP2 and p53. However, a simple model for KAI1 regulation by p53 has been ruled out (Feng et al., 2015).

The promotion of homotypic cell-cell adhesion is an important metastasis suppressive function of KAI1. Tumor cells must detach from the cell mass in order to invade adjacent tissue. The ability to invade is associated with the transition of cell-cell and cell-ECM adhesion molecules. It has been suggested that KAI1 has the ability to reorganize the assembly of membrane proteins and molecular concentration of integrins, which modulate the adhesive strength of the cell and promotes cell aggregation (Feng et al., 2015). In high grade prostate cancer cells it has been shown how up regulation of the primary fibronectin receptor a5 integrin restores the fibronectin matrix assembly, leading to increased cell cohesion and impeded detachment of the cells from the primary tumor. Numerous in vitro studies have shown that KAI1 overexpression inhibits cell motility and invasion (Feng et al., 2015). The molecular basis of these metastasis suppressive effects have not been completely elucidated, but recent reports propose a combination of altered KAI1-protein interactions and signaling pathways. It has been suggested that KAI1 interacts directly with the epidermal growth factor receptor (EGF-R) which weakens migration signaling by rapid desensitization of EGF-induced signals (Feng et al., 2015). Also the actin cytoskeleton organizing FAK-Lyn-p130$^{CAS}$-CrkII pathway is attenuated by KAI1 mediated inhibition of the active p130$^{CAS}$-CrkII complex formation. As a metastasis suppressor, KAI1 has not only the task to suppress cell motility but also to prevent invasion of tumor cells by inactivating proteases that degrade the extracellular matrix. KAI1 causes a redistribution of urokinase plasminogen activator surface receptor (uPAR) and 5031 integrins. This redistribution results in macromolecular assemblies that prevent uPAR from binding its ligand urokinase-type plasminogen activator (uPA) and subsequently in a reduced ECM proteolysis.

Originally, KAI1 has been identified as a metastasis suppressor in rat prostate cancer cells and has ever since been confirmed with the same function in human prostate, melanoma, sarcoma, pancreatic and breast cancer cell lines. In the following solid tumors: melanoma, non-small cell lung, pancreatic, bladder, colon, cervical, ovarian, hepatocarcinoma, gastric, thyroid, laryngeal, and breast cancer, a direct correlation of a good prognosis and KAI1 expression has been observed (Feng et al., 2015). Whereas in malignant tumors, KAI1 expression is significantly reduced (see Yang et al., 2000 as an example for breast cancer). Noteworthy, in at least three solid tumors (gastric, cervical, and ovarian cancers) KAI1 affects not only tumor metastasis but also tumor proliferation. Whether KAI1 expression is reduced in primary ER-negative breast cancers is currently controversial (Feng et al., 2015). The regulatory mechanisms of KAI1 silencing, which do not involve DNA mutation, are slowly being revealed in ER-positive breast cancers, where ER suppresses KAI1 expression. In Hepatocellular carcinoma cells increased level of miR-197 inhibits KAI1 expression via direct interaction with its 3' UTR mRNA sequence (in Feng et al., 2015). Sequence of a human long noncoding RNA of 792 bases without a 3' polyA tail derived from a cDNA library of the GM12878 cell line, contig_343318 has been deposited in the UCSC data base as UCSC Accession no. wgEncodeEH000148; one of many thousands of transcripts derived off this cell line. However, no other information was known about this RNA transcript. There is therefore a need for efficient modulators of KAI1 that may serve in modulating cell migration—invasion and may be used as therapeutic agents for treating malignant disorders.

SUMMARY OF THE INVENTION

In a first aspect, the invention relates to a modulator of at least one antisense long non-coding RNA found by the present inventors to be a Suppressor of the metastasis suppressor gene KAI1/cluster of differentiation 82 (CD82) in Breast Cancer (named accordingly SKAI1BC, or KAI1 as-lncRNA). In some non-limiting examples, KAI1 is a metastasis suppressor gene in human breast cancer. The modulators of the invention may modulate in some embodiments, at least one of, the level/s and activity of the KAI1 as-lncRNA. For example, the modulator of the invention may modulate the levels of the KAI1 as-lncRNA by modulating its synthesis and/or its stability. More specifically, the modulator of the invention may lead to degradation and/or inhibition in the synthesis of KAI1 as-lncRNA, inhibit the activity/ies of SKAI1BC or alternatively, increase stability thereof and/or enhance the synthesis of said KAI1 as-lncRNA. More specifically, in some embodiments, the KAI1 as-lncRNA modulated by the modulators of the invention has a length of about 700 to about 1000 nucleotides and is encoded upstream of the human KAI1/CD82 gene transcription start site (TSS), in an antisense orientation.

In yet another aspect, the invention relates to a delivery vehicle comprising at least one modulator of at least one KAI1 as-lncRNA. More specifically, the vehicles of the invention comprise any of the modulators defined herein.

A further aspect of the invention relates to a composition comprising an effective amount of at least one modulator of at least one KAI1 as-lncRNA, or any vehicle, matrix, nano- or micro-particle comprising the same, specifically, any of the modulators of the invention. In some alternative embodiments, the compositions of the invention may optionally further comprise at least one of pharmaceutically acceptable carrier/s, excipient/s, auxiliaries, and/or diluent/s.

A further aspect of the invention relates to a method for modulating the expression of the KAI1 gene in a cell. In more specific embodiments, the method of the invention may comprise the step of contacting said cell with a modulatory effective amount of at least one modulator of at least one KAI1 as-lncRNA, as defined by the invention or with any vehicle, matrix, nano- or micro-particle, or a composition comprising the same.

Still further aspect of the invention relates to a method of treating, preventing, inhibiting, reducing, eliminating, protecting or delaying the onset or ameliorating the severity of a malignant disorder in a subject in need thereof. More specifically, the method of the invention may comprise the step of administering to the subject a therapeutically effective amount of at least one modulator of at least one KAI1 as-lncRNA, as defined by the invention or with any vehicle, matrix, nano- or micro-particle, or a composition comprising the same.

Still further, the invention provides a diagnostic or prognostic method for diagnosing, determining the progression or monitoring a malignant disorder in a subject. More specifically, the method comprising: in a first step (a) determining the expression level of at least one KAI1 as-lncRNA in at least one biological sample of said subject, to obtain an expression value; and (b) determining if the expression value obtained in step (a) is positive or negative with respect to a predetermined standard expression value or to an expression value of said KAI1 as-lncRNA in at least one control sample.

In yet a further aspect, the invention provides a kit comprising:

(a) at least one detecting molecule specific for determining the level of expression of at least one KAI1 as-lncRNA in a biological sample. In some specific embodiments, the kit of the invention may optionally further comprise at least one of: (b) pre-determined calibration curve/s or predetermined standard/s providing standard expression values of said at least one KAI1as-lncRNA; and (c) at least one control sample.

These and other aspects of the invention will become apparent by the hand of the following description.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which:

FIG. 1. Actinomycin D in RT of KAI1 lncRNA transcript

Total MDA-MB-231 RNA has been reverse transcribed with M-MLV RTase with/without 50 ng/µl Actinomycin D in a total volume of 20 µl. Using for the RT primers recited in Table 2 below for the PCR a 252 bp KAI1 as-lncRNA product (and a 178 bp KAI1 mRNA product as control for RNA intactness) were amplified after dilution of Actinomycin D to 2.5 ng/µl (5/100) or 1.25 ng/µl (5/200). Abbreviations: −RT=no RT enzyme added. −Primer/−Pri (+)=no primer in RT reaction. +RT=with RT enzyme. −tpl=no template in PCR. +ActD=50 ng/µl Actinomycin D in RT reaction. 100 bp=DNA ladder.

FIG. 2A-FIG. 2C. RTase-dependence of KAI1 as-lncRNA transcript

FIG. 2A. Total MDA-MB-231 RNA was reverse transcribed with either M-MLV RTase or AMV RTase using varying units, and a transcript specific RT-primer. Amplification with two different primer pairs results in 168 bp or 254 bp DNA products. FIGS. 2B and 2C. Total MDA-MB-231 RNA was reverse transcribed with M-MLV RTase (200 U) and AMV RTase (25 U) using Hexamer priming. 50 ng/µl Actinomycin D was added per RT-reaction. Amplification of 654 bp long product with Hot start Taq-Polymerase. Abbreviations: −RT=no RT enzyme added. +RT=with RT enzyme. −tpl/no tpl=no template in PCR. +ActD=50 ng/µl Actinomycin D in RT reaction. 100 bp=DNA ladder.

Figure 3:
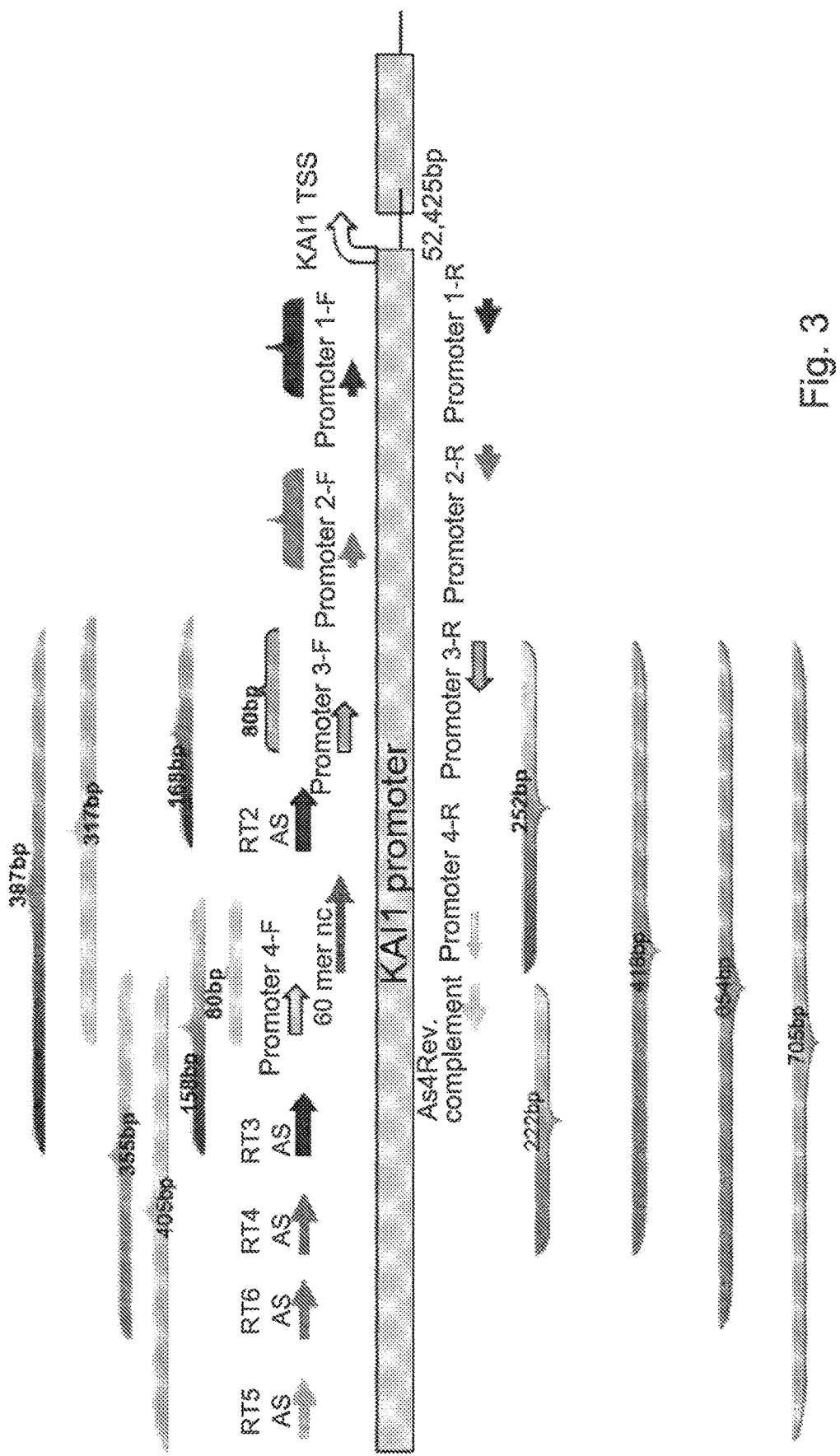

FIG. 3. Scheme of primer walk on KAI1 as-lncRNA transcript

Arrows indicate position of designed primer in either sense or antisense orientation.

FIG. 4. 705 bp amplified PCR product of KAI1 as-lncRNA

MDA-MB-231 RNA DNase and periodate treated was reverse transcribed with specific RT5 primer (+RT). PCR amplification leads to 705 bp product. Abbreviations: −RT=no RTase control; −tpl=no template control; M=DNA marker; gnmc=genomic DNA.

FIG. 5A-FIG. 5B. KAI1 as-lncRNA is nuclear and non-polyadenylated

FIG. 5A. Polyadenylated MDA-MB-231 RNA was pulled down with magnetic beads, while polyA minus-RNA remained in the flow through fraction. Both fractions and total RNA were reverse transcribed with KAI1 as-lncRNA specific primer. PCR amplifies 168 bp product. FIG. 5B. MDA-MB-231 RNA (2 ug nuclear or total RNA fraction) was reverse transcribed with KAI1 as-lncRNA specific primer in presence (+RT) or absence (−RT) of RTase. 317 bp amplified PCR product indicated with an arrow. Abbreviations: −PrN=no primer control in nuclear RNA fraction; −PrT=no primer control in total RNA fraction; gnmc=genomic DNA control; M=DNA marker; −RT=no RTase in total RNA sample; −tpl=no template control. Red arrow indicates the expected 168 bp product.

Figure 6:
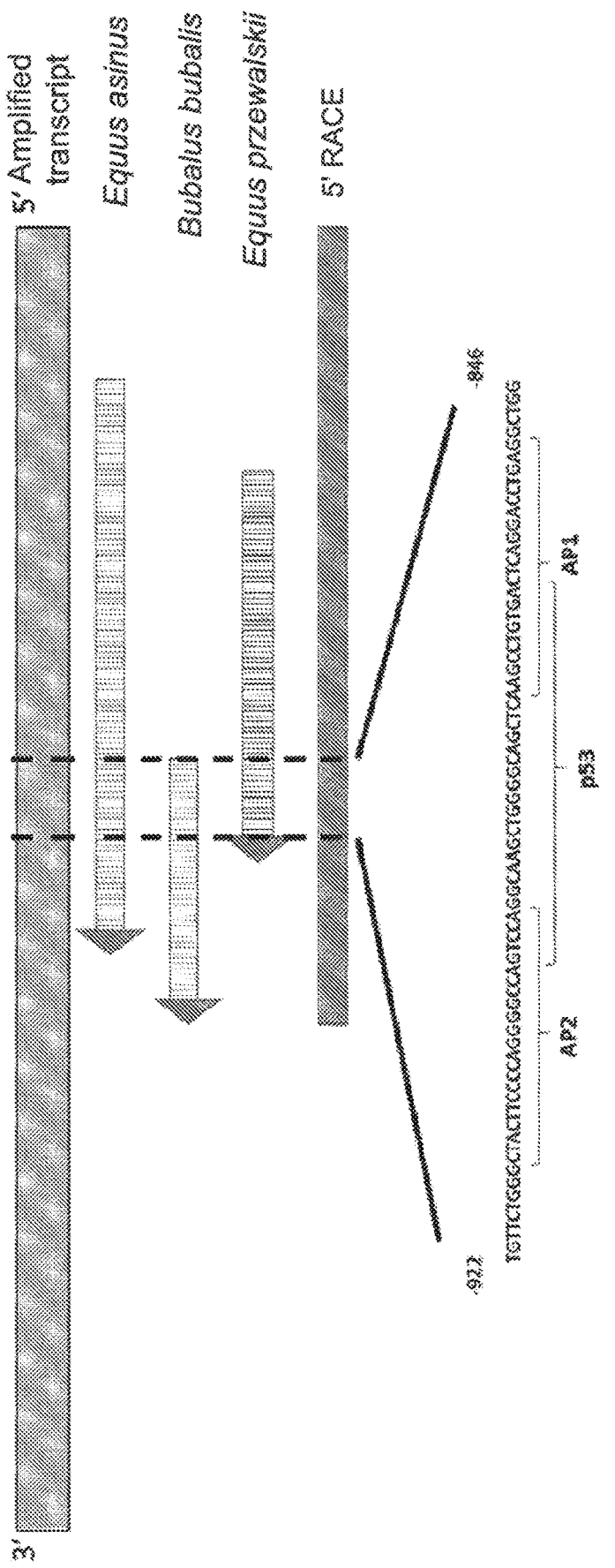

FIG. 6. Mammalian transcripts homologue to KAI1 as-lncRNA

Schematic illustration of the characterized KAI1 as-lncRNA transcript (top) and relative position of homologue transcripts found in *Equus asinus*, *Equus przewalskii* and *Bubalus bubalis* (middle three lines). 5' end of KAI1 as-lncRNA product (bottom line), with 78 nucleotide DNA sequence (also denoted by SEQ ID NO. 49) mutual to all transcripts known as the KAI1 enhancer with its transcription proteins binding sites.

FIG. 7A-FIG. 7E. KAI1 bidirectional promoter-luciferase assay

FIG. 7A. 1198 bp region relative to the KAI1 gene.

FIG. 7B. pGL3-luciferase constructs. Upper: pGL3-luc-basic-1198 bp KAI1 promoter in antisense orientation; middle: pGL3-luc-basic-1198 bp KAI1 promoter in sense orientation; lower: pGL3-luc-basic. FIG. 7C. Dual luciferase assay in HEK293T cells. FIG. 7D. Dual luciferase assay in MCF-7 cells. FIG. 7E. Dual luciferase assay in MDA-MB-231 cells.

Figure 8:
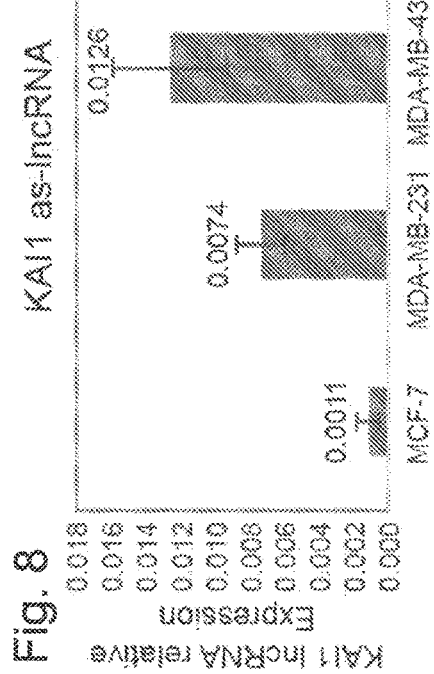

FIG. 8. KAI1 as-lncRNA Expression

MCF-7, MDA-MB-231, MDA-MB-435 and SUM159PT cell lines derived RNAs were subjected to DNase. Then 1 μg RNA of each was reverse transcribed with RevertAid Premium. KAI1 as-lncRNA levels relative to KAI1 mRNA were evaluated by quantitative Real-Time PCR method. Average of three independent experiments measured in triplicates.

Figure 9:
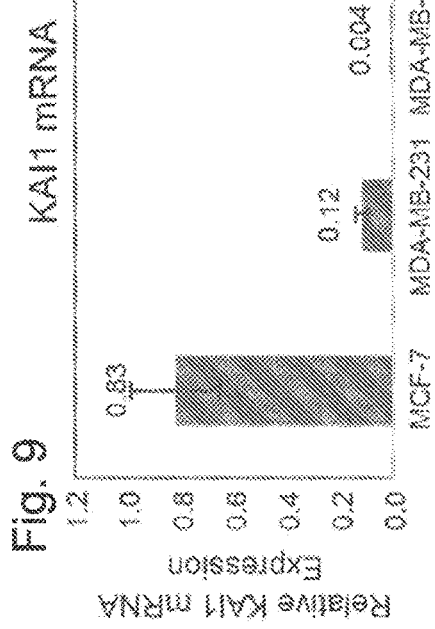

FIG. 9. KAI1 mRNA Expression

MCF-7, MDA-MB-231, MDA-MB-435 and SUM159PT cell lines derived RNAs were subjected to DNase. Then 1 μg RNA of each was reverse transcribed using Oligo dT(15) priming. KAI1 mRNA levels relative to endogenous control HPRT mRNA were evaluated by quantitative Real-Time PCR method. Average of three independent experiments measured in triplicates.

Figure 10:
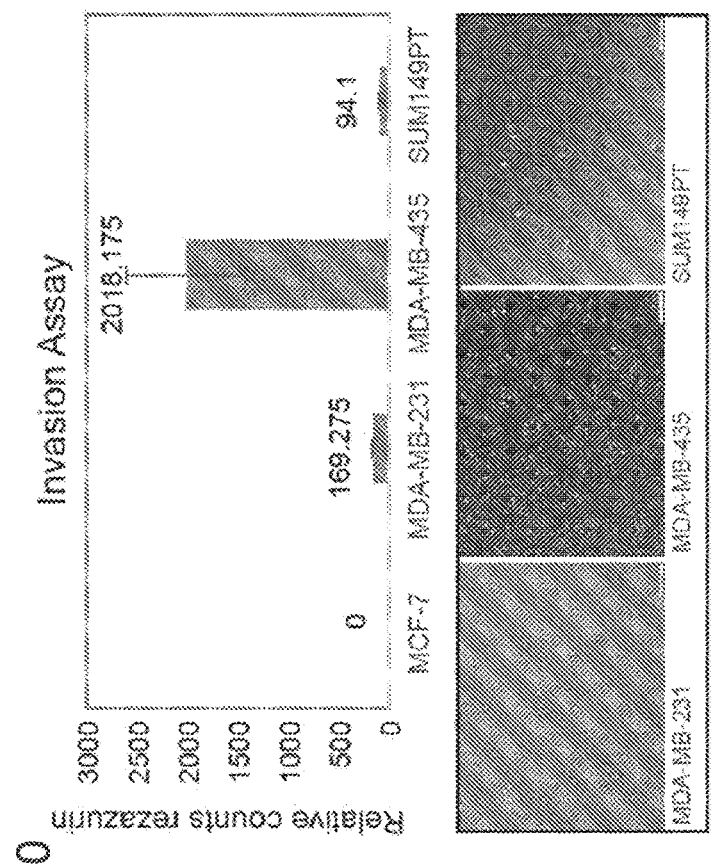

FIG. 10. Invasion Assay

MCF-7, MDA-MB-231, MDA-MB-435 and SUM159PT cells were seeded in Matrigel coated transwell chambers. Cells invading from upper chamber to the chemoattractant (10% serum) in the lower chamber were detected using resazurin cell viability assay. Images of random fields were taken by light-field microscope camera as illustrative support.

FIG. 11A-FIG. 11C. Quantitation of KAI1 as-lncRNA following its knockdown in MDA-MB-231, MDA-MB-435 and MCF-7 cells Quantitative Real-Time PCR after MDA-MB-231 (FIG. 11A), MDA-MB-435 (FIG. 11B) or MCF-7 (FIG. 11C) infection with SHC-shRNA vector empty, SHC-shRNA-non-silencing (ns) or shRNA against KAI1 as-lncRNA ("SHC-shRNA-1"). All samples were reverse transcribed with RevertAid Premium RTase (or without RTase as control). Results are average of five independent experiments in triplicates. HPRT served as endogenous control. Pv ("SHC-shRNA-1")<0.001 and pv (ns)>0.05 in all three cell lines.

FIG. 12A-FIG. 12C. KAI1 mRNA expression following KAI1 as-lncRNA knockdown via SHC lentiviral based vector MDA-MB-231 (FIG. 12A), MCF-7 (FIG. 12B), and MDA-MB-435 (FIG. 12C) cells infected with SHC203-KAI1-as-lncRNA-shRNA ("SHC-shRNA-1"), non-silencing shRNA or empty vector control. Relative KAI1 mRNA Expression quantified by Real-Time PCR with HPRT-1 as endogenous control. Abbreviations: "SHC-shRNA-1": knockdown: p<0.01. P-value ns=not significant.

Figure 13B:
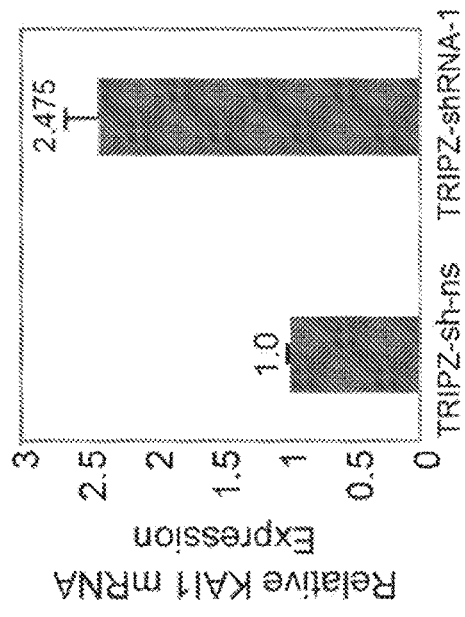
Figure 13A:
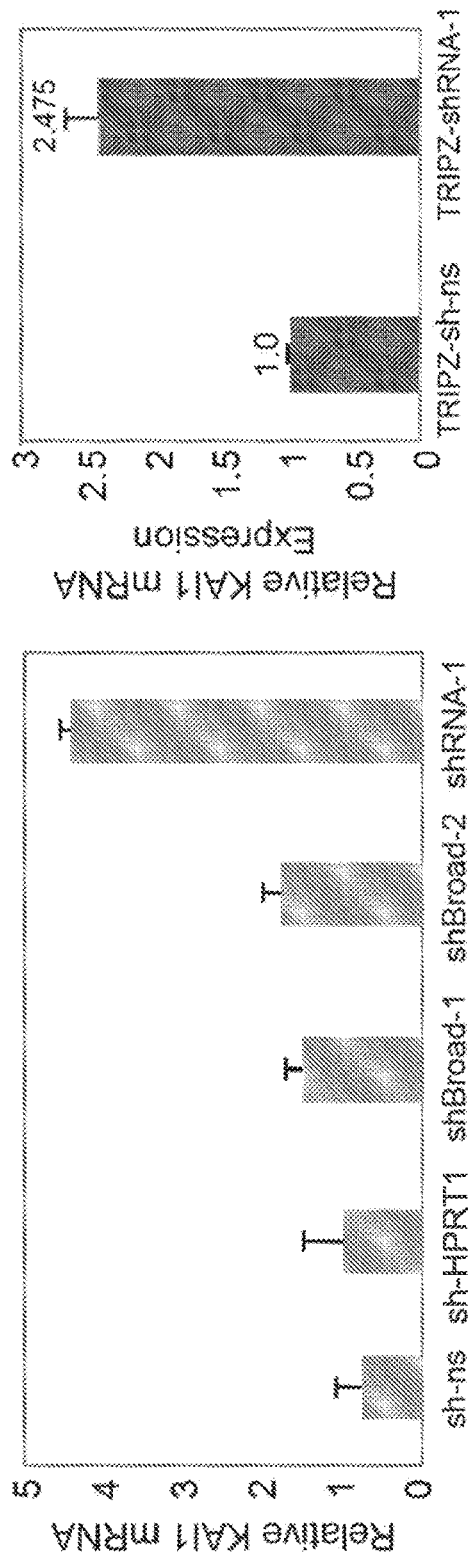

FIG. 13A-13B. KAI1 mRNA level following KAI1 as-lncRNA knockdown via the TRIPZ lentiviral based vector MDAMB-435 (FIG. 13A) and MDA-MB-231 (FIG. 13B) cells were infected with TRIPZ-shRNA-1 (A & B) or with TRIPZ-Broad-1- or TRIPZ-Broad-2 shRNAs expressing lentiviruses (A), to disrupt the KAI1 as-lncRNA (see their structure/construction in Experimental procedures). Doxycycline 2.5 μg/μl and/or puromycin 0.1-1 μg/ml were added 24 hours post infection. Relative KAI1 mRNA Expression was quantified by Real-Time PCR with HPRT-1 as endogenous control. In panel B knockdown: p<0.01.

Figure 14:
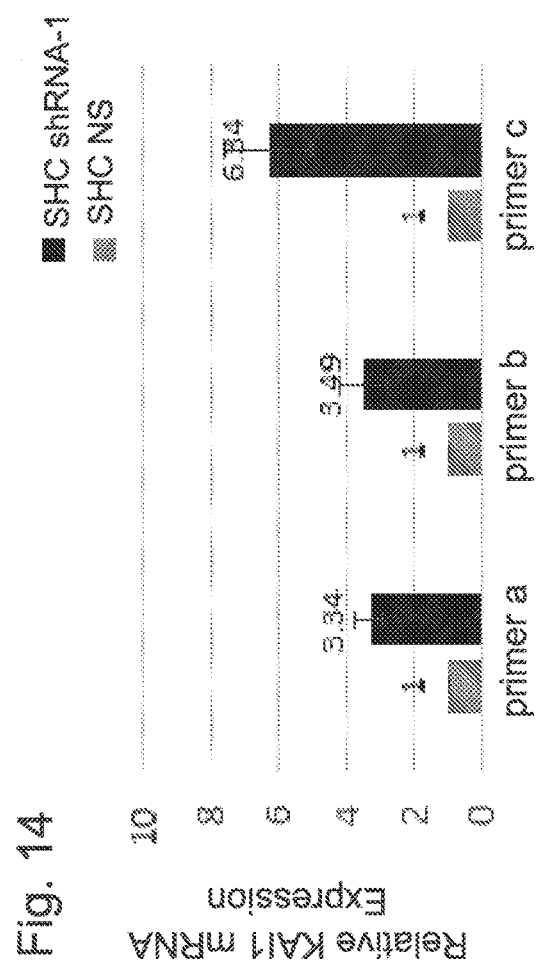

FIG. 14. KAI1 mRNA variants expression levels following KAI1 as-lncRNA knockdown MDA-MB-231 cells infected with SHC203-KAI1-as-ncRNA-shRNA ("SHC-shRNA-1") or non-silencing shRNA control. Relative KAI1 mRNA expression quantified by Real-Time PCR with HPRT-1 as endogenous control. Primers pair "a" amplifies KAI1 transcript variants 01, 02, 07, 12 and 14; primers pair "b" amplifies KAI1 transcripts 01, 07 and 14; primers pair "c" amplifies KAI1 transcript 01.

Figure 15A:
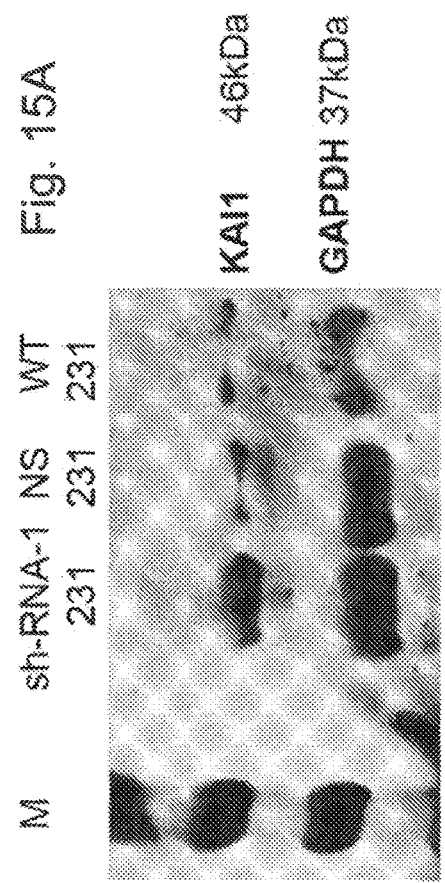
Figure 15B:
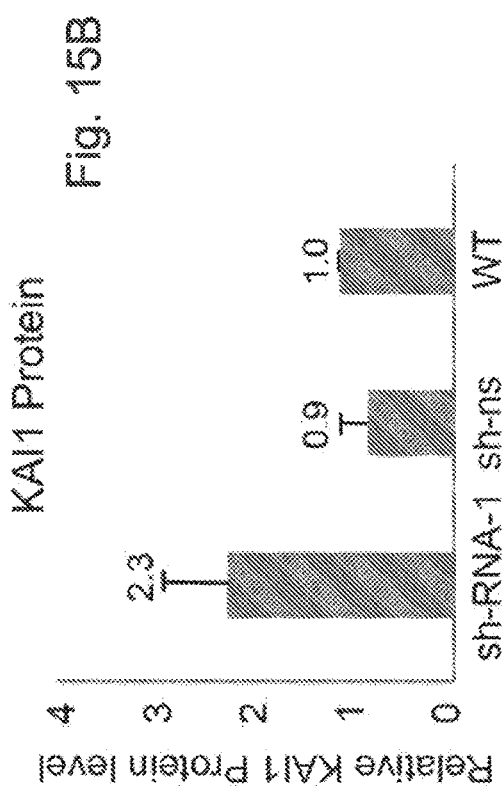

FIG. 15A-FIG. 15B. KAI1 protein expression following KAI1 as-lncRNA knockdown via SHC lentiviral based vector FIG. 15A. Wild type MDA-MB-231 cells (WT), or those infected with SHC-Lentivirus encoding either shRNA "SHC-shRNA-1" directed against KAI1 as-lncRNA, or expressing scrambled "non-silencing" shRNA (NS). Proteins were lysed in 2% CHAPS. 80 μg protein were loaded on 10% SDS-PAGE gel, immunostained with C-16 anti KAI1 and FL-335 anti GAPDH (both Santa Cruz) and detected using the Odyssey Infrared Imager. Quantitative analysis was performed with ImageJ Software. FIG. 15B. Average of quantitative analysis of three independent experiments performed as in 14 A.

Figure 16A:
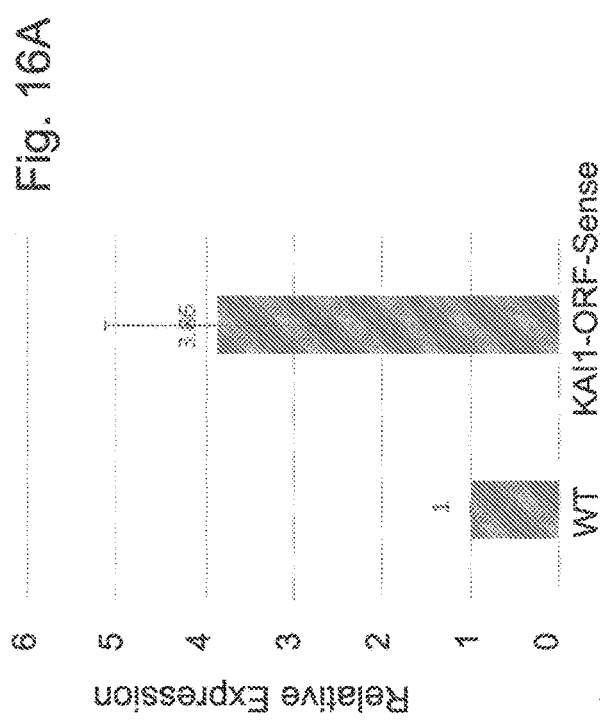
Figure 16B:
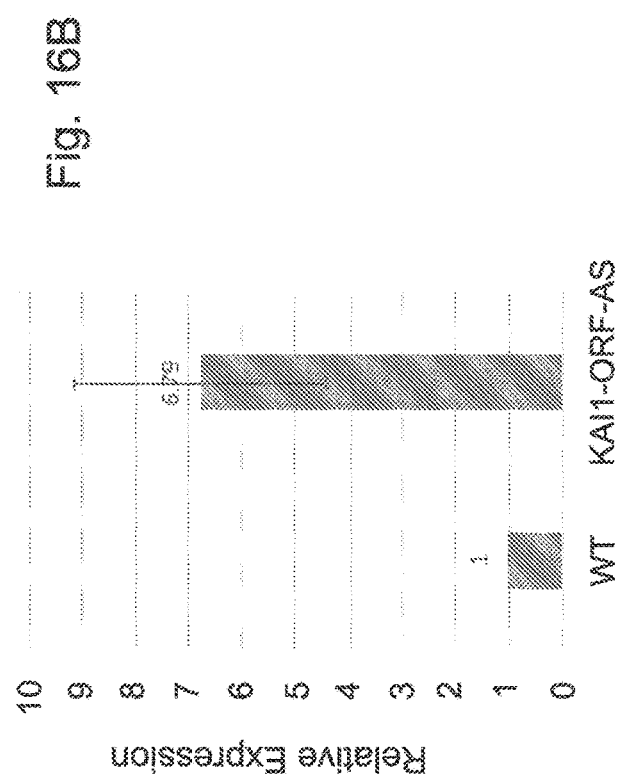
Figure 16C:
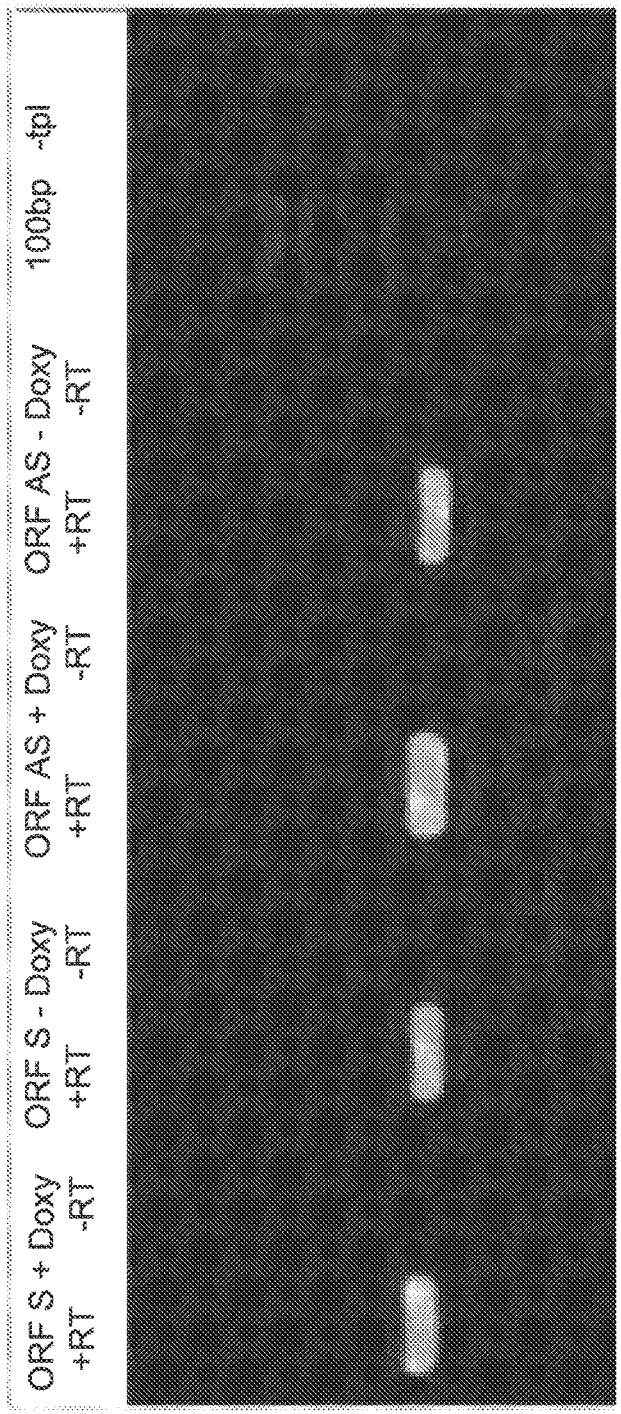
Figure 16E:
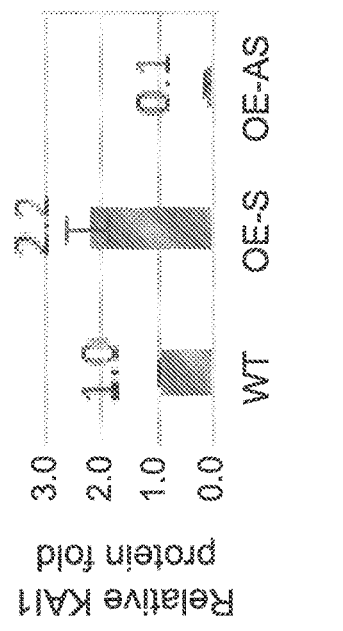
Figure 16D:
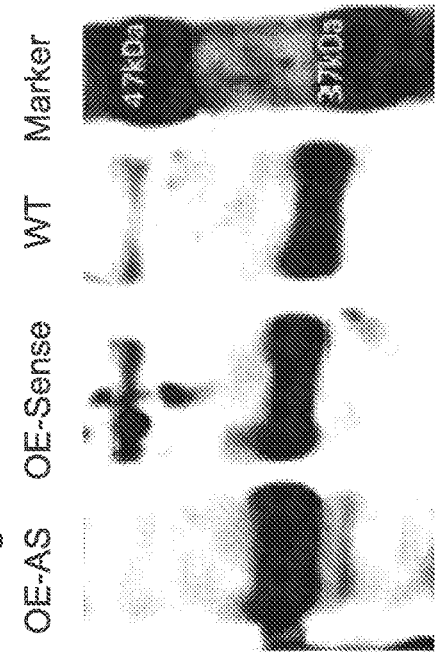

FIG. 16A-FIG. 16E. Ectopic KAI1 RNA expression following KAI1 ORF expression in sense or antisense orientation KAI1 ORF in sense (ORF Sense, FIG. 16A) or antisense (ORF AS, FIG. 16B) orientation were overexpressed in MDA-MB-231. Quantitative Real-Time PCR with overexpression induced by Doxycycline (+Dox) or not induced (−Dox). FIG. 16C. Semi-quantitative KAI1 ORF sense or ORF antisense overexpression. Amplified product (40 cycles) of quantitative Real Time-PCR loaded on 2% agarose gel. +RT=reverse transcription with RTase. −RT=no RTase control. −tpl=no template control. 100 bp=DNA ladder. +Doxy=induced overexpression. −Doxy=not induced overexpression. FIG. 16D. Western Blot. MDA-MB-231 cells infected with TRIPZ-ORF Sense or Antisense Vector. 50 ug protein on 12% SDS-PAGE Gel. Antibody KAI1: 47 kDa; Antibody endogenous control GAPDH: 37 kDa. FIG. 16E. Semi-quantitative Image analysis with ImageJ of three independent experiments.

Figure 17:
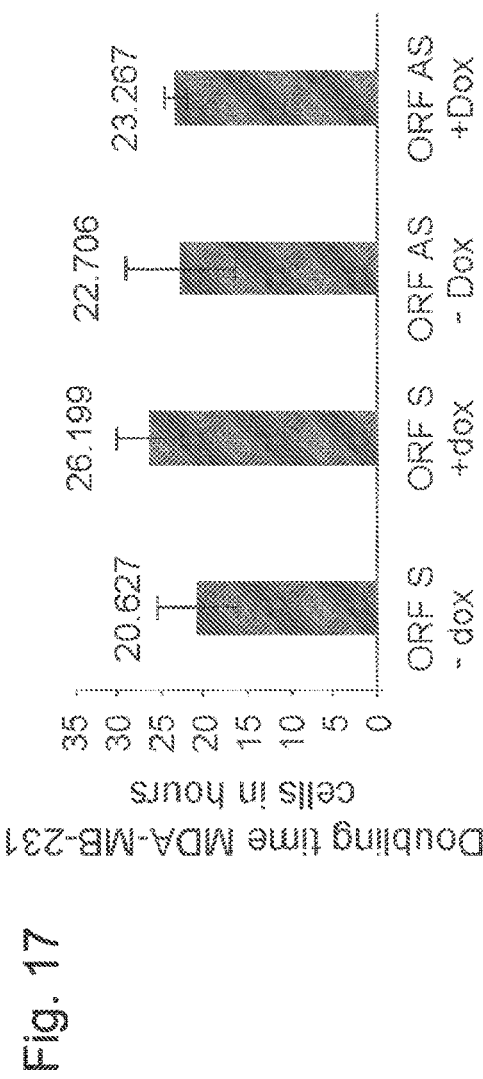

FIG. 17. Doubling time of MDA-MB-231 cells after KAI1 overexpression

MDA-MB-231 cells infected with the lentivirus TRIPZ-KAI1 ORF in sense or antisense orientation, under doxycycline induced (+dox) or non-induced (−dox) conditions. Doubling time tracked by resazurin cell viability assay over four days.

Figure 18:
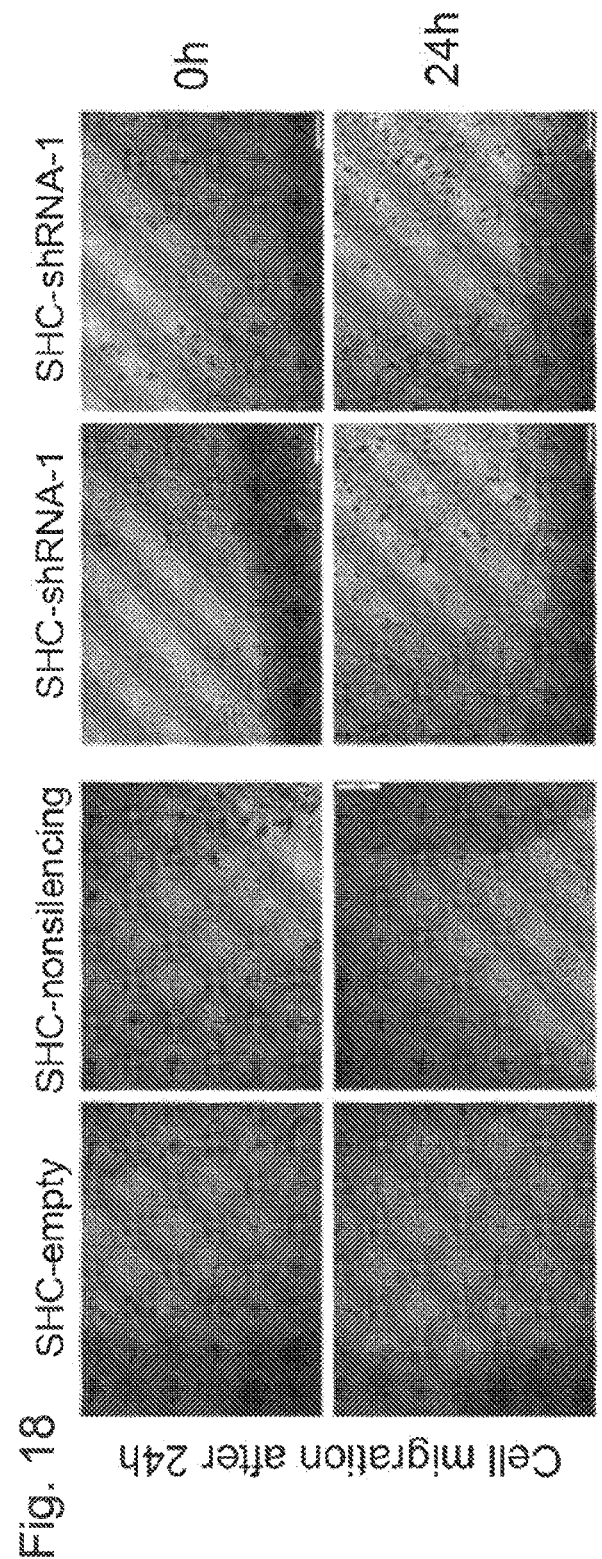

FIG. 18. Wound healing assay in KAI1 as-lncRNA knockdown cells infected with SHC lentivirus MDA-MB-231 cells infected with respective SHC-shRNA lentiviral vector generated virus subjected to in vitro scratch wounding. Images captured after 0 and 24 hours using light-field microscope. Images represent four repetitions with duplicates.

Figure 19:
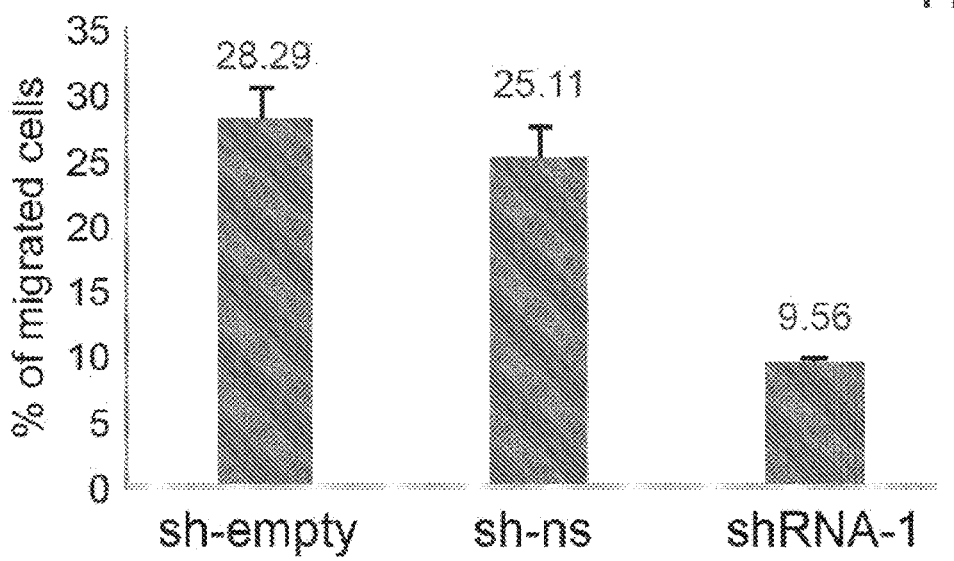

FIG. 19. Migration assay of KAI1 as-lncRNA knockdown MDA-MB-231 cells

MDA-MB-231 cells infected with respective SHC-shRNA-vector based lentiviruses and seeded in uncoated transwell chamber. Cells invading from upper chamber to the chemoattractant (10% serum) in lower chamber were detected using resazurin cell viability assay. Percent of invaded cells calculated by mock migration control. Images were taken by light-field microscope camera as illustrative support. pv SHC-shRNA-1 <0.05; pv ns >0.05.

Figure 20:
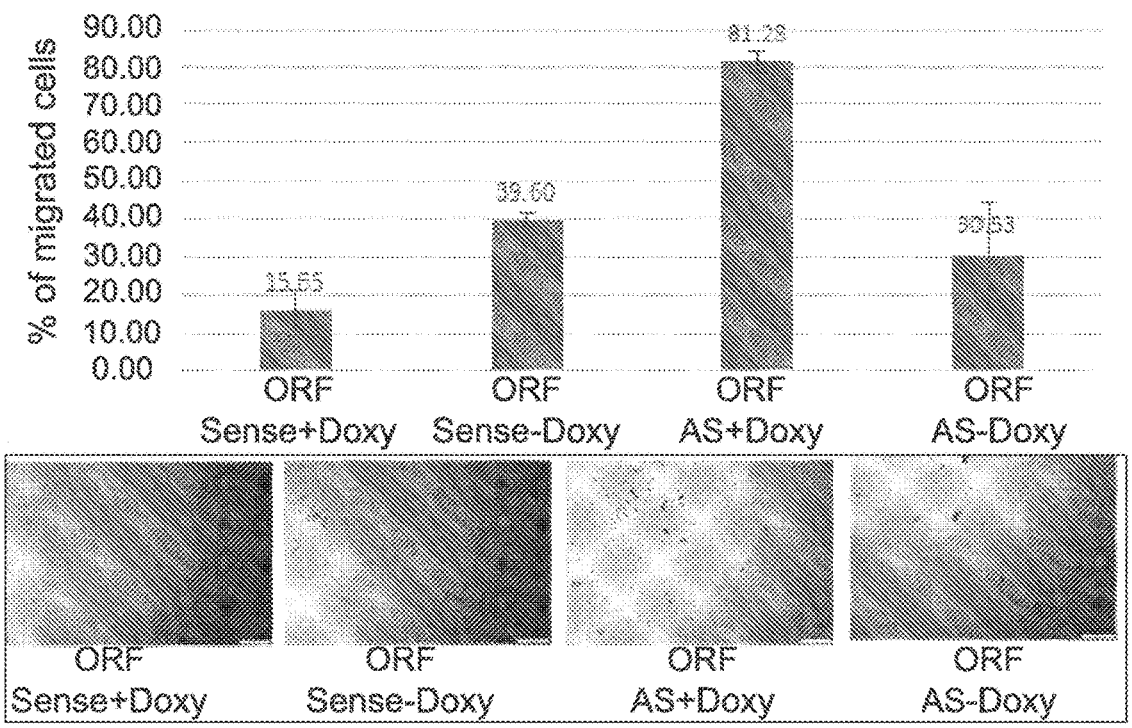

FIG. 20. Migration assay of KAI1 overexpressing MDA-MB-231 cells

Doxycycline induced or non-induced MDA-MB-231 cells infected with respective TRIPZ KAI1-ORF sense or anti-sense lentiviruses and seeded in trans-well chamber. Cells invading from upper chamber to chemoattractant (10% serum) in lower chamber were detected using resazurin cell viability assay. Percent of invaded cells calculated by mock FIG. 21. Fibronectin Adhesion assay of KAI1 as-lncRNA knockdown MDA-MB-231 cells 50,000 MDA-MB-231 cells infected with respective SHC-shRNA expressing viruses were seeded on fibronectin coated 48-well plate and were allowed to attach for 30 min. Attached cells were detected using resazurin cell viability assay and compared to control cells. Average of three independent experiments using triplicates as samples. P-value n.s. =not significant; p-value **=<0.01.

Figure 22:
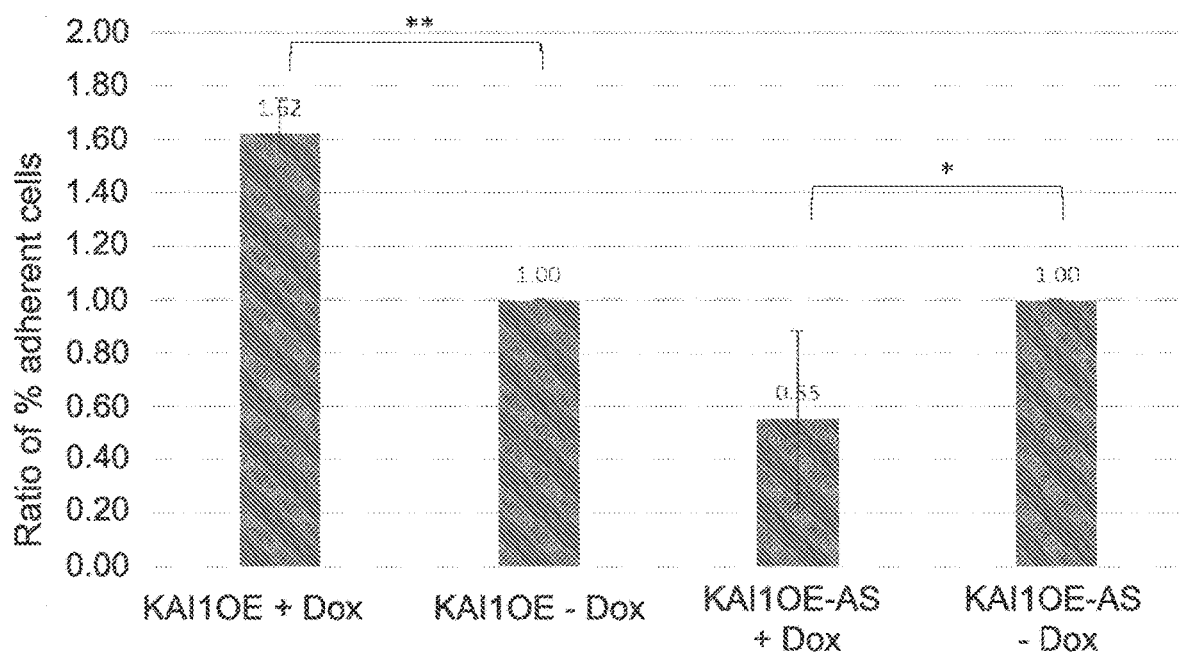

FIG. 22. Fibronectin Adhesion assay of KAI1 overexpressing MDA-MB-231 cells

About 50,000 induced or non-induced MDA-MB-231 cells infected with respective TRIPZ-KAI1 over-expressing viruses (or the OE-AS under-expressing viruses) were seeded on fibronectin coated 48-well and were allowed to attach for 30 min. Attached cells were detected using resazurin cell viability assay and compared to control cells. Average of three independent experiments using triplicates as samples. P-value *=0.41; p-value **=0.03

Figure 23:
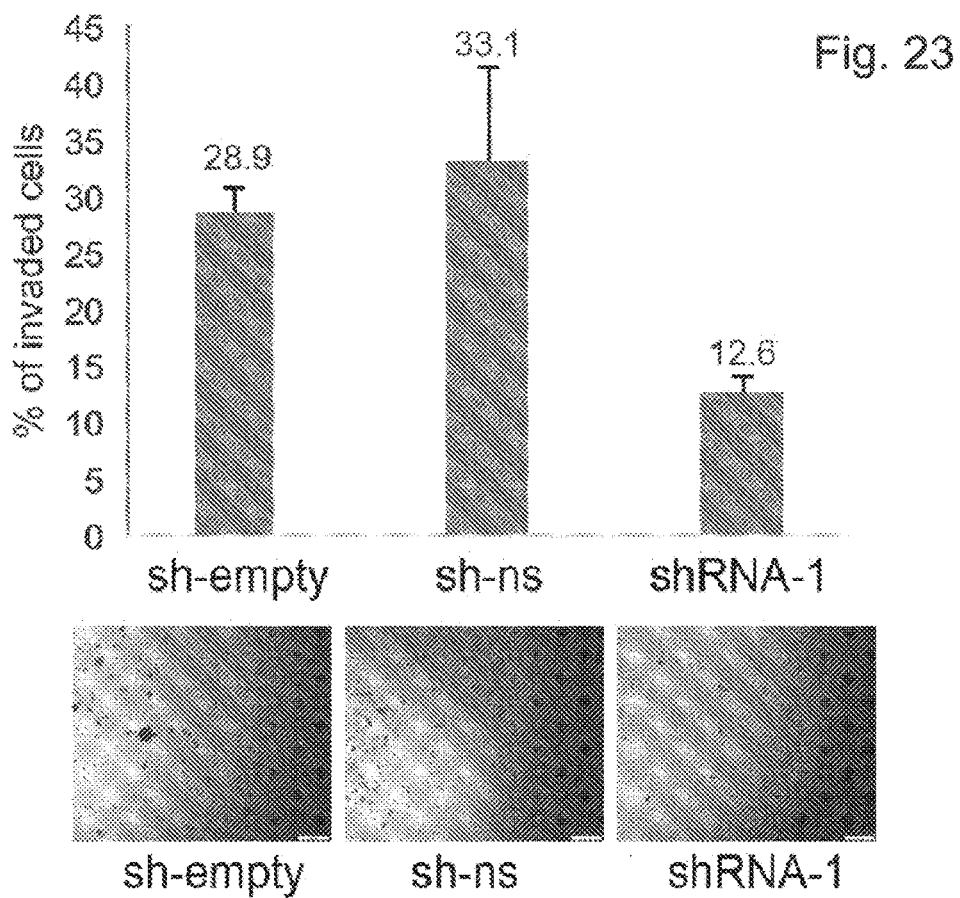

FIG. 23. Invasion Assay of KAI1 as-lncRNA knockdown MDA-MB-231 cells infected with SHC lentivirus MDA-MB-231 cells infected with respective SHC-shRNA-vector and seeded in Matrigel coated transwell chamber. Cells invading from upper chamber to chemoattractant (10% serum) in lower chamber were detected using resazurin cell viability assay. Percent of invaded cells calculated by mock invasion control. Images were taken by light-field microscope camera. pv "SHC-shRNA-1"<0.05; pv ns >0.05.

Figure 24:
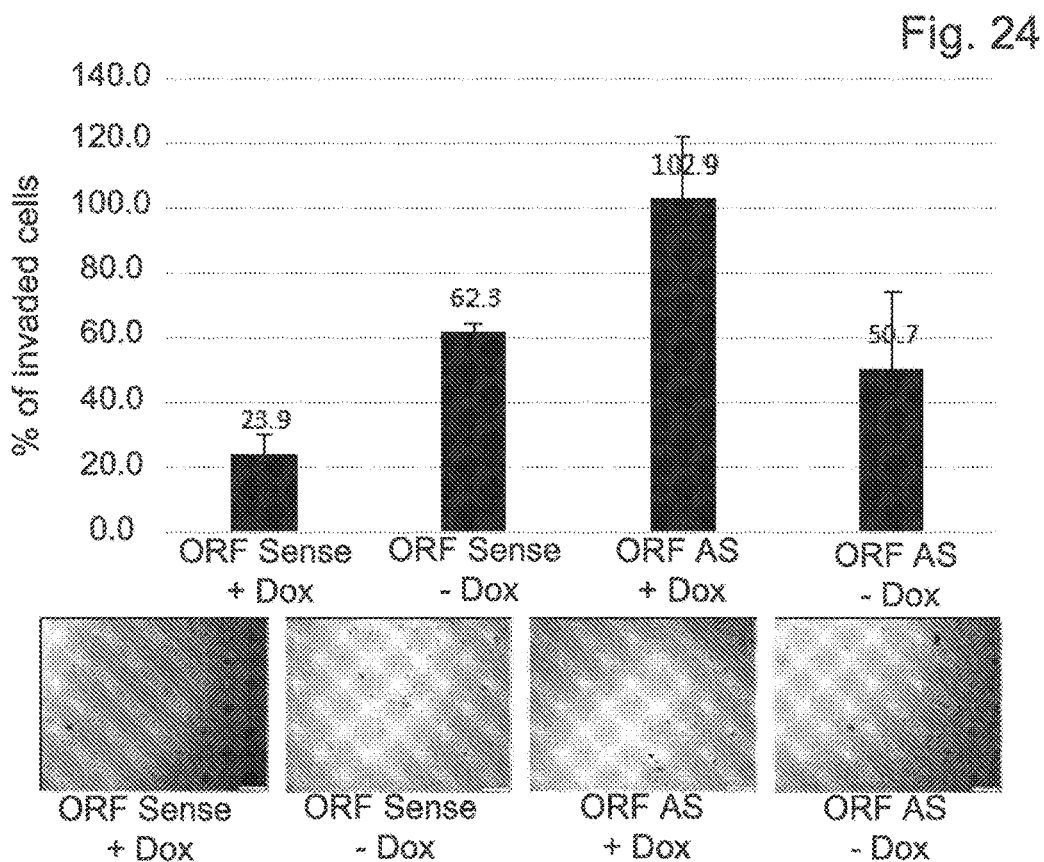

FIG. 24. Invasion Assay of KAI1 overexpressing MDA-MB-231 cells infected with TRIPZ virus Induced or non-induced MDA-MB-231 cells infected with respective TRIPZ-KAI1ORF over-expressing viruses (or ORF-AS under-expressing viruses) and seeded in Matrigel coated trans-well chamber. Cells invading from upper chamber to chemoattractant (10% serum) in lower chamber were detected using resazurin cell viability assay. Percent of invaded cells calculated by mock invasion control. Images were taken by light-field microscope camera.

DETAILED DESCRIPTION OF THE INVENTION

Inactivation of tumor/metastasis suppressor genes via epigenetic silencing is a frequent event in human cancers, including breast cancer. KAI1 is a metastasis suppressor gene whose normal protecting activity is deficient in at least twelve different malignancies. However, as no point mutations have been found in this gene, it is being assumed that KAI1 expression is being epigenetically silenced in these human tumors. The inventors have identified and characterized a 792 bases long non-polyadenylated, primarily nuclear, human antisense (as) lncRNA, initiating 386 bp upstream of the KAI1 (CD82) human metastasis suppressor gene transcription start site; and thus elongating in the opposite direction to KAI1 mRNA. KAI1/CD82 has been demonstrated as a metastasis suppressor in at least the following solid human cancers: prostate, melanoma, thyroid, pancreatic, bladder, ovarian, cervical, gastric, colorectal, hepatocarcinoma, lung and breast. The inventors have now shown that the expression of this transcript, named herein as KAI1 as-lncRNA, emerges to be inversely related to the KAI1 mRNA expression, and in direct relationship to the invasiveness level of human breast cancer derived cell lines. Moreover, knockdown of the KAI1 as-lncRNA in the triple negative breast cancer cell line MDA-MB-231 have led to increased KAI1 mRNA and protein expression, manifested in stronger adhesion to fibronectin, retardation of cell migration and reduced cell invasion in vitro. These results uncover a potential way to harness tumor metastasis via targeting the KAI1 as-lncRNA in human breast cancer, as well as in the other mentioned cancers. These observations also raise the possibility of using the KAI1 as-lncRNA as a novel biomarker for cancer progression/aggressiveness.

Thus, in a first aspect, the invention relates to a modulator of at least one antisense long non-coding RNA of the metastasis suppressor gene KAI1/cluster of differentiation 82 (CD82) (KAI1as-lncRNA). More specifically, in some embodiments, the KAI1 as-lncRNA has a length of about 700 to about 1000 nucleotides and is encoded upstream of the KAI1/CD82 gene transcription start site (TSS), specifically, the major TSS.

As used herein, the term "long non-coding RNA" or "lncRNA" or "long ncRNA" is functionally defined as non-protein coding RNA transcript that is longer than approximately 200 nucleotides and therefore should be distinguished from small regulatory RNAs such as microRNAs (miRNAs), short interfering RNAs (siRNAs), Piwi-interacting RNAs (piRNAs), small nucleolar RNAs (snoRNAs), and other short RNAs. It has been recently recognized that lncRNAs are exquisitely regulated, are restricted to specific cell types and frequently have evolutionarily conserved function, secondary structure and regions of micro homology. It is now recognized that lncRNAs may interact with proteins to modulate protein function, regulate protein-protein interactions or direct localization within cellular compartments, and as such may play a role in the control of mRNA stability, splicing and translation. In some embodiments, as being located upstream to the KAI1/CD82 gene, the KAI1 as-lncRNA of the invention may regulate, at least one of the transcription, stability, splicing and translation of the KAI1 gene.

As used herein, an "antisense long non-coding RNA" is a long non-coding RNA whose transcription occurs in the antisense orientation as defined herein below.

More specifically, in some embodiments, the lncRNA of the invention may be located upstream of the KAI1/CD82 gene transcription start site (TSS). The term "transcription" as known in the art refers to the first step of gene expression, in which a particular DNA segment is copied into RNA, for example messenger RNA (mRNA), by the RNA polymerase enzyme. During transcription, a DNA sequence is read by an RNA polymerase, which produces a complementary, anti-parallel RNA strand. Transcription proceeds in the following general steps: first an RNA polymerase, together with one or more transcription factors (TFs), binds to promoter DNA. RNA polymerase then creates a transcription bubble, which separates the two strands of the DNA helix. Next the RNA polymerase adds RNA nucleotides (which are complementary to the nucleotides of one DNA strand) and then RNA sugar-phosphate backbone forms with assistance from RNA polymerase to form an RNA strand. Hydrogen bonds of the RNA-DNA helix then break, freeing the newly synthesized RNA strand. The RNA may be further processed by for example polyadenylation, capping, and splicing.

The stretch of DNA transcribed into an RNA molecule is termed "sense" strand when encoding at least one protein. If the gene encodes a protein, the template for transcription is termed "antisense" strand (namely the complementary DNA molecule) and transcription produces mRNA identical to the sense strand that serves as a template for protein synthesis by translation. Alternatively, the transcribed gene may encode for example non-coding RNA such as microRNA (miRNA), ribosomal RNA (rRNA), transfer RNA (tRNA), and the like.

Therefore, the term "antisense orientation" as used herein refers to the 3' to 5' directionality on the coding DNA strand (sense strand). The coding DNA strand is identical to the messenger RNA (mRNA) and is used to encode the expected protein; for example, ATG in the sense DNA may correspond to an AUG codon in the mRNA, encoding the amino acid methionine.

As indicated above, the KAI1 as-lncRNA of the invention is located upstream of the KAI TSS. The core promoter is the minimal region of DNA required for the RNA polymerase to assemble with the general transcription factors and form the pre-initiation complex for transcription. The core promoter contains the transcription start site (TSS), which is defined as the most 3' nucleotide of the RNA encoding strand which is transcribed into mRNA by the RNA Polymerase, i.e. the exact location where transcription starts.

As noted above, the lncRNA of the invention may be located upstream of the KAI1/CD82 gene, and therefore may play a role in the regulation of KAI1/CD82 gene expression, function and stability.

KAI1, as used herein refers to the human KAI1 metastasis suppressor gene encoding for a 267 amino acid plasma membrane glycoprotein, which has four transmembrane domains and one large and one small extracellular domain. Plasma membrane expression of KAI1 is downregulated during the progression of several cancers to a metastatic state, including prostate, lung, and pancreatic cancers. KAI1 protein is a member of the transmembrane four superfamily (TM4SF). Members of the TM4SF are cell membrane proteins that contain four hydrophobic, presumably transmembrane, domains and one large extracellular, hydrophilic domain that often contains potential N-linked glycosylation sites. KAI1 (CD82) contains three potential N-linked glycosylation sites and is thus a glycoprotein. KAI1 is identical to the previously characterized antigens R2, IA4, C33 and 4F9 and is designated CD82 by the clusters of differentiation (CD) nomenclature. In some specific embodiments, the KAI1 protein as used herein refers to the human KAI1 protein. More specifically, this protein may comprise the amino acid sequence as disclosed by GenBank: AAC51205.1, specifically, the amino acid sequence as denoted by SEQ ID NO. 40. In yet some further embodiments, the human KAI1 protein is encoded by the nucleic acid sequence as disclosed by GenBank: U20770.1, specifically as denoted by SEQ ID NO. 50.

The KAI1 as-lncRNA of the invention is located upstream of the KAI1 gene. The term used herein "upstream" and "downstream" both refer to a relative position in DNA or RNA. Each strand of DNA or RNA has a 5' end and a 3' end, so named for the carbon position on the deoxyribose (or ribose) ring. By convention, upstream and downstream relate to the 5' to 3' direction in which RNA transcription takes place. Upstream is toward the 5' end of the DNA or RNA molecule and downstream is toward the 3' end. When considering double-stranded DNA, upstream is toward the 5' end of the protein coding strand for the gene in question and downstream is toward the 3' end. Due to the anti-parallel nature of DNA, this means the 3' end of the mRNA template strand is upstream of the gene and the 5' end is downstream.

As used herein, the term "5'" refers to the part of the strand that is closer to the 5' end or 5' terminus, i.e. to the extremity of the DNA or RNA strand that has a phosphate group attached to the fifth carbon in the sugar-ring of the deoxyribose or ribose at its terminus. Furthermore, the term "3'" refers to the part of the strand that is closer to the 3' end or 3' terminus, i.e. to the extremity of the DNA or RNA strand that has a hydroxyl group linked to the 3rd carbon in the sugar-ring of the deoxyribose or ribose at its terminus.

In addition, in order to define the position of a nucleotide on a DNA coding strand, the terms "minus" (also represented by the "−" symbol) or "plus" (also represented by the "+" symbol) are employed. The term "minus" corresponds to a position which is upstream to the TSS (considered as the position "one") and the term "plus" corresponds to a position which is downstream to the TSS. As indicated above, the KAI1 as-lncRNA, specifically, the 5' terminus thereof may be located in a position of between about 10 to 1000 bp upstream or the KAI1/CD82 gene TSS, specifically, about 10, 20, 30, 40, 50, 60, 70, 80, 90, 100, 150, 200, 250, 300, 350, 400, 450, 500, 550, 600, 650, 700, 750, 800, 850, 900, 950, 1000 or more base pairs upstream to KAI1/CD82 gene TSS. In yet some further embodiments, the 5' terminus of the KAI1 as-lncRNA in accordance with the invention may be located at position of between about 250 to 500 bp upstream of the KAI1 TSS, specifically, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500 bp or more upstream of the KAI1 TSS. In yet some further specific embodiments, the KAI1 as-lncRNA in accordance with the invention may be located at position of between about 375, 376, 377, 378, 379, 380, 381, 382, 383, 384, 385, 386, 387, 388, 389, 390 or more bp upstream of the KAI1 TSS. In some particular and non-limiting embodiments, the 5' terminus of the KAI1 as-lncRNA referred to by the invention may be located 386 bp upstream of the KAI1 TSS. Thus, in some specific embodiments, the 5' terminus of the KAI1 as-lncRNA is located at position −386 of the KAI1 gene transcription start site (TSS). In yet some further specific embodiments, the KAI1 as-lncRNA is located in an antisense orientation. Therefore as used herein, the "position −386 of the KAI1 gene transcription start site (TSS)" corresponds to the 386$^{th}$ nucleotide in the upstream direction (i.e. toward the 5' end) on the DNA coding strand from the TSS of the KAI1 gene.

Still further, according to some embodiments, the KAI1 as-lncRNA of the invention has a length of between about 200 to 1000 or more nucleotides, specifically, 200, 250, 300, 350, 400, 450, 500, 550, 600, 650, 700, 750, 800, 850, 900, 950, 1000 or more nucleotides. More specifically, the KAI1 as-lncRNA of the invention has a length of between about 700 or less to 800 or more nucleotides, specifically, 700, 705, 710, 715, 720, 725, 730, 735, 740, 745, 750, 755, 760, 765, 770, 775, 780, 785, 790, 795, 800 or more nucleotides. In yet some further specific embodiments the KAI1 as-lncRNA of the invention has a length of 780 or less to about 800 or more nucleotides, specifically, 780, 781, 782, 783, 784, 785, 786, 787, 788, 789, 790, 791, 792, 793, 794, 795, 796, 797, 798, 799, 800 or more nucleotides. In certain embodiments, the KAI1 as-lncRNA is about 792 nucleotides long, specifically, the KAI1 as-lncRNA is 792 nucleotides long.

In yet some further embodiments, the modulator of the invention modulates KAI1 as-lncRNA that in certain embodiments may be the human KAI1 as-lncRNA, also referred to herein as suppressor of KAI1 in breast cancer (SKAIBC).

In yet some further specific embodiments, the modulator of the invention modulates the human KAI1 as-lncRNA that comprises a nucleic acid sequence as denoted by SEQ ID NO: 46, or any fragments, homologs or variants thereof.

In some embodiments, the modulator of the invention modulates the amount or levels and/or the activity of KAI1 as-lncRNA (also referred to herein as SKAI1BC), thereby modulating the expression of the KAI1/CD82 gene. In some specific embodiments, the modulator of the invention may modulate the levels the KAI1 as-lncRNA, for example by modulating the stability (e.g., increases or decreases the degradation) and/or the synthesis of the KAI1 as-lncRNA transcript. In yet some alternative or additional embodiments, the modulator/s of the invention may modulate the actual activity of SKAI1BC (e.g., via binding and thus blocking its active site/s).

As noted above, the invention provides modulators of KAI1 as-lncRNA that may either inhibit or alternatively enhance KAI1 as-lncRNA levels and/or activity.

More specifically, the terms "inhibition", "moderation", "reduction" or "attenuation" as referred to herein, relate to the retardation, restraining or reduction of the KAI1 as-lncRNA levels and/or activity by the modulator/s of the invention by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, or about 99% to 99.9% or more, specifically, 100%. Alternatively, the terms "increase", "augmentation" and "enhancement" as used herein relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of the KAI1 as-lncRNA levels and/or activity by the modulator/s of the invention. It should be appreciated that 10%, 50%, 120%, 500%, etc., are interchangeable with "fold change" values, i.e., 0.1, 0.5, 1.2, 5, etc., respectively. 10%, 50%, 120%, 500%, etc., are interchangeable with "fold change" values, i.e., 0.1, 0.5, 1.2, 5, etc., respectively. Therefore, the term increase refers to an increase of about 2, 3, 4, 5, 6, 7, 8, 9, 10, 20, 30, 40, 50, 60, 70, 80, 90, 100, 200, 300, 400, 500, 600, 700, 800, 900, 1000 folds or more.

"SKAI1BC levels" or "KAI1 as-lncRNA levels", as used herein may indicate the amount of SKAI1BC that may reflect either the rate of its synthesis, e.g., transcription (e.g., as defined herein before) and/or its stability.

Stability of RNA, as used herein refers to any modulation in the stability of the KAI1 as-lncRNA RNA of the invention by the modulators disclosed herein. More specifically, RNA modifications are changes to the chemical composition of ribonucleic acid (RNA) molecules post-synthesis that have the potential to alter function or stability.

RNA modifications that increases stability may include capping i.e. the addition of a methylated guanine nucleotide cap to the 5' end of mRNAs, cleavage and polyadenylation i.e. cleavage of the 3' end of the RNA and then the addition of about 250 adenine residues to form a poly(A) tail. Thus, in some embodiments, the modulators of the invention may modulate the KAI1 as-lncRNA RNA stability by directly or indirectly modulating any of the processes involved in capping, cleavage and/or polyadenylation.

In yet some further embodiments, the modulators of the invention may modulate KAI1 as-lncRNA RNA stability by directly or indirectly modulating its degradation. More specifically, RNA degradation is mediated by three major classes of intracellular RNA-degrading enzymes (ribonucleases or RNases): endonucleases that cut RNA internally, 5' exonucleases that hydrolyze RNA from the 5' end, and 3' exonucleases that degrade RNA from the 3' end. The specificity of RNA degradation mechanisms is frequently conferred by cofactors such as helicases, polymerases and chaperones.

The ATP-dependent RNA helicases are a large protein family that participates in almost all pathways of RNA processing and degradation. The eukaryotic exosome complex exhibit both 3' exonuclease and endonuclease activity and function together with helicase family members Mtr4 and Ski2, in the RNA degradation process.

Still further, in some additional or alternative embodiments, the modulators provided and used by the invention may either increase or decrease the translation of the KAI1 as-lncRNA of the invention.

In yet some further embodiments, the modulator/s or the invention may modulate the activity of the KAI1 as-lncRNA or the SKAI1BC.

Without being bound by any theory, the KAI1 as lncRNA may bind in the nuclei its complementary DNA sequences in the region of KAI1 promoter/enhancer and in that way inhibits KAI1 mRNA synthesis. Alternatively, or additionally, this lncRNA may bind protein/s which constitute part of the chromatin complex in this region (the KAI1 bi-directional promoter/enhancer). Such proteins may include transcription factor/s unique for KAI1 gene or for a group of genes.

Thus, in some embodiments, the KAI1 as lncRNA "activity" as referred to herein may include the inhibition of KAI1 synthesis (transcription), by blocking at least one of, the KAI1 promoter and/or enhancer, by inhibiting binding, recognition or activity of required transcription factors or alternatively, by disturbing or reducing the stability of the KAI1 gene product, for example, by any of the stability or degradation processes disclosed herein above.

Thus, in some embodiments, a compound that would bind the lncRNA may either distract it from (or alternatively enhance) inhibiting the transcription of KAI1.

More specifically, in some particular embodiments, the invention provides modulator/s that may lead, either directly or indirectly to reduction in at least one of the level and activity of the KAI1 as-lncRNA transcript, thereby increasing the expression of the KAI1/CD82 gene.

In some specific embodiments, the modulator of the invention may reduce the synthesis of KAI1 as-lncRNA, for example, by inhibiting transcription thereof, thereby increasing the expression of the KAI1/CD82 gene. Non-limiting embodiments for inhibiting transcription of the KAI1 as-lncRNA, may include for example, inhibiting unique transcription factor/s required for KAI1 as-lncRNA transcription.

In yet some further specific embodiments, the modulator of the invention may reduce the levels of KAI1 as-lncRNA, by reducing its stability.

In some particular embodiments, the invention provides modulator/s that may lead, either directly or indirectly to reduction in the activity of the KAI1 as-lncRNA transcript, thereby increasing the expression of the KAI1/CD82 gene.

In yet some further embodiments, the modulator of the invention may comprise at least one of at least one nucleic acid molecule at least one polypeptide, at least one Peptide-Nucleic Acid (PNA), at least one aptamer, at least one small organic molecule and any combinations thereof.

In more specific embodiments, the modulator of the invention may be a nucleic acid molecule. In more particular embodiments, such nucleic acid molecule may be a molecule comprising at least one of a single stranded DNA (ssDNA), a single stranded RNA (ssRNA), a double stranded DNA (dsDNA), a double stranded RNA (dsRNA), nucleic acid molecule having at least one modified nucleotide/s and any combinations thereof.

More specifically, in certain embodiments a modulator that reduces the amount or levels of KAI1 as-lncRNA (either by reducing the stability, increasing the degradation and/or reducing synthesis thereof), and/or inhibiting or reducing the activity of KAI1 as-lncRNA, may be a nucleic acid molecule that may comprise at least one of a short hairpin RNA (shRNA), a small interfering RNA (siRNA), microRNA (miRNA), antisense oligonucleotide (ASO), locked nucleic acid (LNA), as well as other nucleic acids derivatives.

As noted above, in some embodiments, the modulator of the invention may be a dsRNA molecule participating in RNA interference. RNA interference (RNAi) is a general conserved eukaryotic pathway which down regulates gene expression in a sequence specific manner. It is the process of sequence-specific, post-transcriptional gene silencing in animals and plants, initiated by siRNA that is homologous in its duplex region to the sequence of the silenced gene. Gene silencing is induced and maintained by the formation of partly or perfectly double-stranded RNA (dsRNA) between the target RNA and the siRNA/shRNA derived 'guide" RNA strand. The expression of the gene is either completely or partially inhibited.

As known in the art RNAi is a multistep process. In a first step, there is cleavage of large dsRNAs into 21-23 ribonucleotides-long double-stranded effector molecules called "small interfering RNAs" or "short interfering RNAs" (siRNAs). These siRNAs duplexes then associate with an endonuclease-containing complex, known as RNA-induced silencing complex (RISC). The RISC specifically recognizes and cleaves the endogenous mRNAs/RNAs containing a sequence complementary to one of the siRNA strands. One of the strands of the double-stranded siRNA molecule (the "guide" strand) comprises a nucleotide sequence that is complementary to a nucleotide sequence of the target gene, or a portion thereof, and the second strand of the double-stranded siRNA molecule (the passenger" strand) comprises a nucleotide sequence substantially similar to the nucleotide sequence of the target gene, or a portion thereof.

In more particular embodiments, siRNAs comprise a duplex, or double-stranded region, of about 18-25 nucleotides long. Often, siRNAs contain from about two to four unpaired nucleotides at the 3' end of each strand. At least a portion of one strand of the duplex or double-stranded region of a siRNA is substantially homologous to or substantially complementary to a target sequence within the gene product (i.e. RNA) molecule as herein defined. The strand complementary to a target RNA molecule is the "antisense guide strand", the strand homologous to the target RNA molecule is the "sense passenger strand" (which is also complementary to the siRNA antisense guide strand). siRNAs may also be contained within structured such as miRNA and shRNA which has additional sequences such as loops, linking sequences as well as stems and other folded structures.

More specifically, the strands of a double-stranded interfering RNA (e.g., siRNA) may be connected to form a hairpin or stem-loop structure (e.g., shRNA). Thus, as mentioned above the modulator of the present invention may also be a short hairpin RNA (shRNA), as exemplified below by the Inventors.

According to other embodiments the modulator according to the present disclosure may be a micro-RNA (miRNA). miRNAs are small RNAs made from genes encoding primary transcripts of various sizes. They have been identified in both animals and plants. The primary transcript (termed the "pri-miRNA") is processed through various nucleolytic steps to a shorter precursor miRNA, or "pre-miRNA." The pre-miRNA is present in a folded form so that the final (mature) miRNA is present in a duplex, the two strands being referred to as the miRNA. The pre-miRNA is a substrate for a form of dicer that removes the miRNA duplex from the precursor, after which, similarly to siRNAs, the duplex can be taken into the RISC complex. Unlike, siRNAs, miRNAs bind to transcript sequences with only partial complementarity and usually repress translation without affecting steady-state RNA levels. Both miRNAs and siRNAs are processed by Dicer and associate with components of the RNA-induced silencing complex (RISC).

More specific embodiments relate to the modulator of the invention being a nucleic acid modulator that may comprise at least one shRNA molecule. In more particular embodiments, such shRNA may comprise a nucleic acid sequence complementary at least in part to KAI1 as-lncRNA or to any fragment/s or variant/s thereof. The term "shRNA", as used herein, refers to an RNA agent having a stem-loop structure, comprising a first and second region of complementary sequence. The degree of complementarity and orientation of the regions being sufficient such that base pairing occurs between the regions. The first and second regions being joined by a loop region, the loop resulting from a lack of base pairing between nucleotides (or nucleotide analogs) within the loop region. Some of the nucleotides in the loop can be involved in base-pair interactions with other nucleotides in the loop.

In some specific embodiments, the shRNA used as the modulator of the invention may comprise a sequence complementary to the target KAI1 as lncRNA, having a length of between about 5 to 50 nucleotides, specifically, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 46, 37, 38, 39, 40, 41, 42, 43, 44, 45, 46, 47, 48, 49, 50 or more nucleotides. In more specific embodiments, the complementary sequence may be in a length ranging between 9 to 29 nucleotides.

More specific embodiments of the invention provide a modulator that comprises an shRNA molecule. As shown in the Examples, specifically, FIGS. 11-15, an effective shRNA molecule provided by the invention as a modulator of KAI1 as lncRNA that reduces at least one of its levels and/or activity, may be an shRNA molecule designated herein as shRNA-1. Thus, in yet some further specific embodiments the modulator of the invention may be an shRNA molecule that may comprise a nucleic acid sequence comprising at least one of the nucleic acid sequence as denoted by SEQ ID NO: 6 and SEQ ID NO: 5 or any analogs or derivatives thereof. As shown in FIG. 13, further shRNA molecules were provided by the invention. These molecule, for example, molecules designated as Broad-1 and Broad-2, although may be in some embodiments less effective as compared with shRNA-1 in elevating KAI1 levels, are also provided by the invention. Thus, in yet some further embodiments, the nucleic acid sequence/s of an alternative shRNA molecule that may be used as a regulator of the invention may comprise the nucleic acid sequences as denoted by any one of SEQ ID NO. 47 and 48, also referred to herein as Broad-1 and Broad-2, respectively.

In certain embodiments, the modulator of the invention may be an shRNA molecule comprising nucleic acid sequences as denoted by SEQ ID NO: 5 and SEQ ID NO: 6, both separated by a loop region having a length of about 5 to about 50 nucleotides. In some specific embodiments, the loop region may have a length of about 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 45, 46, 37, 38, 39, 40, 41, 42, 43, 44, 45, 46, 47, 48, 49, 50 or more nucleotides. In more specific embodiments, the loop may have the length of 6 to 19 nucleotides, specifically, 6, 7, 8, 9, 10, 11, 12, 13, 14, 15, 16, 17, 18, 19 or more nucleotides.

In yet some further specific and non-limiting embodiments, the modulator of the invention may be an shRNA molecule comprising the nucleic acid sequence as denoted by at least one of SEQ ID NO. 4, SEQ ID NO. 18 and SEQ ID NO. 19, or any fragments, variants or derivatives thereof.

In some alternative embodiments, the polynucleotide modulators of the present invention may comprise heterocyclic nucleosides consisting of purines and the pyrimidines bases, bonded in a 3' to 5' phosphodiester linkage.

Examples of specific polynucleotide modulators useful according to this aspect of the present invention include polynucleotide modulators containing modified backbones or non-natural internucleoside linkages.

Modified polynucleotide backbones include, for example, phosphorothioates, chiral phosphorothioates, phosphorodithioates, phosphotriesters, aminoalkyl phosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3-5' linkages, 2-5' linked analogs of these, and those having inverted polarity wherein the adjacent pairs of nucleoside units are linked 3'-5' to 5'-3' or 2'-5' to 5'-2'. Various salts, mixed salts and free acid forms can also be used.

Alternatively, modified polynucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

Other polynucleotide modulators that can be used according to the present invention, are those modified in both sugar and the internucleoside linkage, i.e., the backbone, of the nucleotide units are replaced with novel groups. The base units are maintained for complementation with the appropriate polynucleotide target. An example for such a polynucleotide mimetic includes peptide nucleic acid (PNA). A PNA polynucleotide refers to a polynucleotide where the sugar-backbone is replaced with an amide containing backbone, in particular an aminoethylglycine backbone. The bases are retained and are bound directly or indirectly to aza nitrogen atoms of the amide portion of the backbone.

The polynucleotide modulators of the present invention may also include base modifications or substitutions. As used herein, "unmodified" or "natural" bases include the purine bases adenine (A) and guanine (G), and the pyrimidine bases thymine (T), cytosine (C) and uracil (U). Modified bases include but are not limited to other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine.

The polynucleotide modulators of the present invention may be generated according to any polynucleotide synthesis method known in the art such as enzymatic synthesis or solid phase synthesis. Equipment and reagents for executing solid-phase synthesis are commercially available from, for example, Applied Biosystems. Any other means for such synthesis may also be employed; the actual synthesis of the polynucleotides is well within the capabilities of one skilled in the art and can be accomplished via established methodologies utilizing solid phase chemistry, e.g. cyanoethyl phosphoramidite followed by deprotection, desalting and purification by for example, an automated trityl-on method or HPLC.

As indicated above and herein, in some embodiments the modulators of the invention may be also small molecules. By the term "small molecule drug" (SMD) it is meant a biologically active low molecular weight organic compounds, characterized as having molecular weight up to 900 Daltons and a size in the order of 10 nm. Most drugs are SMDs. It is thus conceived that the molecular weight of the modulators of the invention may be in the range of at least about 1-1000 Daltons, or 100-900 Daltons, or 200-800 Daltons, or 300-700 Daltons, or 400-600 Daltons. It is further conceived that such modulators in the range of 1-10 nm, or 1-20 nm, or 1-30 nm, or 1-40 nm or 1-50 nm.

SMDs are more likely to be absorbed, although some of them are only absorbed after oral administration if given as prodrugs. One advantage that SMDs have over "large molecule" biologics (mainly peptides and proteins), is that they can be designed as metabolically stable and orally active, and can be taken orally.

In yet another aspect, the invention relates to a delivery vehicle comprising at least one modulator of at least one KAI1 as lncRNA. More specifically, the KAI1 as-lncRNA modulated by the modulator of the invention may have a length of about 700 to about 1000 nucleotides and is encoded upstream of the KAI1 gene TSS, specifically, the major TSS in antisense orientation.

In yet some further embodiments, the delivery vehicle of the invention may comprise any of the modulators as defined by the invention herein before.

Still further, the delivery vehicle of the invention may be a viral vector.

In some specific embodiments the vectors used by the invention may be any viral vectors, particular viral vectors useful in the invention may include but are not limited to lentivirus, adenovirus, or an adeno-associated virus (AAV).

In some specific embodiments, the viral vectors of the invention may be TRIPZ-shRNA to KAI1 as-lncRNA lentivirus and the SHC203-shRNA to KAI1 as-lncRNA lentivirus.

As used herein the term "nucleic acid delivery vehicle" in the context of the present disclosure is used in its broadest sense. "Vehicles" or "delivery Vehicles" as used herein encompass vectors such as bacteriophage, plasmids, phagemides, viruses, integratable DNA fragments, episomal plasmids/viruses, and other vehicles or system, which enable the transfer of nucleic acid molecules into a desired target host cell, or enable the integration of a specific nucleic acid molecule in a particular location and in some further embodiments, leads to expression of said transduced nucleic acid molecule in the target cell. Non limiting examples for systems that may be used by the invention for specific targeted transfer of nucleic acid molecules may include the Clustered Regularly Interspaced Short Palindromic Repeat (CRISPR/Cas) system, the transcription activator effector nuclease (TALEN), the zinc finger protein (ZEN) systems and any equivalent system.

Vectors are typically self-replicating DNA or RNA constructs containing the desired nucleic acid sequences, and operably linked genetic control elements that are recognized in a suitable host cell and effect the transcription and translation of the desired gene. Generally, the genetic control elements can include a prokaryotic promoter system or a eukaryotic promoter expression control system. Such system typically includes a transcriptional promoter, transcription enhancers to elevate the level of RNA expression. Vectors usually contain an origin of replication that allows the vector to replicate independently of the host cell. However there are vectors which are deliberately designed to be replication defective, enabling delivery into the cell and integration into the host genome, be it at random or at predesigned sites.

Accordingly, the term control and regulatory elements includes promoters, terminators and other expression control elements. Such regulatory elements are described in Molecular Cell Biology Editors: H. Lodish et al., $7^{th}$ edition 2013 (or $8^{th}$ edition 2016). For instance, any of a wide variety of expression control sequences that control the expression of a DNA sequence when operatively linked to it may be used in these vectors to express DNA sequences encoding any desired RNA or protein using the method of this invention.

A vector or delivery vehicle may additionally include appropriate restriction sites, antibiotic resistance, fluorescence tags or other markers for positive selection (such as G418 resistance) or negative selection (such as the Herpes viral TK) of vector-containing cells. Plasmids are the most commonly used form of vectors but other forms of vectors which serve an equivalent function and which are, or become, known in the art are suitable for use herein. See, e.g., Ausubel F et al., Current Protocols in Molecular Biology (2016) Wiley on line library.

In some embodiments the delivery vehicle according to the present disclosure may be at least one viral vector, specifically, lentivirus, adeno virus or AAV.

A further aspect of the invention relates to a composition comprising an effective amount of at least one modulator of at least one KAI1 as-lncRNA, or any vehicle, matrix, nano- or micro-particle comprising the same. More specifically, the KAI1 as-lncRNA modulated by the modulator used by the composition of the invention may have a length of about 700 to about 1000 nucleotides and is encoded upstream of the KAI1 gene TSS in an antisense orientation. In some alternative embodiments, the composition of the invention may optionally further comprise at least one pharmaceutically acceptable carrier/s, excipient/s, auxiliaries, and/or diluent/s.

In some particular embodiments, the composition of the invention may comprise any of the modulators described by the invention.

Still further, the invention provides any of the compositions described herein for use in a method of treating, preventing, inhibiting, reducing, eliminating, protecting or delaying the onset, ameliorating the severity of a malignant disorder.

It should be appreciated that the modulators of the invention may be encompassed in any vectors, delivery vehicles or any formulations. Of particular relevance are formulations of compositions of the invention adapted for use as a nano- or micro-particles. Nanoscale drug delivery systems using liposomes and nanoparticles are emerging technologies for the rational drug delivery, which offer improved pharmacokinetic properties, controlled and sustained release of drugs and, more importantly, lower systemic toxicity. A particularly desired solution allows for externally triggered release of encapsulated compounds. Externally controlled release can be accomplished if drug delivery vehicles, such as liposomes or polyelectrolyte multilayer capsules, incorporate nanoparticle (NP) actuators.

More specifically, Controlled drug delivery systems (DDS) have several advantages compared to the traditional forms of drugs. A drug is transported to the place of action, hence, its influence on vital tissues and undesirable side effects can be minimized. Accumulation of therapeutic compounds at the target site increases and, consequently, the required drug doses are lower. This modern form of therapy is especially important when there is a discrepancy between the dose or the concentration of a drug and its therapeutic results or toxic effects. Cell-specific targeting can be accomplished by attaching drugs to specially designed carriers. Various nanostructures, including liposomes, polymers, nano-conjugates, dendrimers, silicon, gold or carbon materials, and magnetic nanoparticles, have been tested as carriers in drug delivery systems. Polymeric nanoparticles are one technology being developed to enable clinically feasible oral delivery. More specifically, the term "nanostructure" or "nanoparticle" is used herein to denote any microscopic particle smaller than about 100 nm in diameter. In some other embodiments, the carrier is an organized collection of lipids. When referring to the structure forming lipids, specifically, micellar formulations or liposomes, it is to be understood to mean any biocompatible lipid that can assemble into an organized collection of lipids (organized structure). In some embodiments, the lipid may be natural, semi-synthetic or fully synthetic lipid, as well as electrically neutral, negatively or positively charged lipid. In some embodiments, the lipid may be a naturally occurring phospholipid. Examples of lipids forming glycerophospholipids include, without being limited thereto, glycerophospholipid. phosphatidylglycerols (PG) including dimyristoyl phosphatidylglycerol (DMPG); phosphatidylcholine (PC), including egg yolk phosphatidylcholine, dimyristoyl phosphatidylcholine (DMPC), 1-palmitoyl-2-oleoylphosphatidyl choline (POPC), hydrogenated soy phosphatidylcholine (HSPC), distearoylphosphatidylcholine (DSPC); phosphatidic acid (PA), phosphatidylinositol (PI), phosphatidylserine (PS). Non-limiting examples of cationic lipids may include, for example, 1,2-dimyristoyl-3-trimethylammonium propane (DMTAP) 1,2-dioleyloxy-3-(trimethylamino) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3f3[N—(N',N'-dimethylaminoethane) carbamoyl] cholesterol (DC-Chol); and dimethyl-dioctadecylammonium (DDAB), N-[2-[[2,5-bis[3-aminopropyl)amino]-1-oxopentyl]amino]ethyl]-N,N-dimethyl-2,3-bis[(1-oxo-9-octadecenyl)oxy]-1-propanaminium (DOSPA), and ceramide carbamoyl spermine (CCS), or the neutral lipid dioleoylphosphatidyl ethanolamine (DOPE) derivatized with polylysine to form a cationic lipopolymer.

As indicated above, the compositions of the invention may optionally further comprise at least one of pharmaceutically acceptable carrier/s, excipient/s, auxiliaries, and/or diluent/s. The phrase "pharmaceutically acceptable carrier" used herein includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome containing formulations.

Formulations include those suitable for topical, oral, rectal, nasal, or parenteral (including subcutaneous, intramuscular, intraperitoneal (IP), intravenous (IV) and intradermal) administration. The nature, availability and sources, and the administration of all such compounds including the effective amounts necessary to produce desirable effects in a subject are well known in the art.

A further aspect of the invention relates to a method for modulating at least one of the level/s and activity of the KAI1 gene product in a cell. In some embodiments, the invention provide methods for modulating the expression of the KAI1 gene. In more specific embodiments, the method of the invention may comprise the step of contacting said cell with a modulatory effective amount of at least one modulator of at least one KAI1 as-lncRNA, or of any vehicle, matrix, nano- or micro-particle, or a composition comprising the same. More specifically, the KAI1 as-lncRNA modulated by the modulator used by the method of the invention may have a length of about 700 to about 1000 nucleotides and is encoded upstream of the KAI1 gene TSS, specifically, the major TSS in an antisense orientation.

In more specific embodiments, the method of the invention may use any of the modulators of the invention, as defined herein before.

The term "contacting" means to bring, put, incubate or mix together. As such, a first item is contacted with a second item when the two items are brought or put together, e.g., by touching them to each other or combining them. In the context of the present invention, the term "contacting" includes all measures or steps, which allow interaction between the modulators of the invention and the cells to be modulated.

As indicated above, the method provided by the invention comprises the step of contacting the cell with "a modulatory effective amount". The terms "effective amount" or "sufficient amount" mean an amount necessary to achieve a selected result. In this connection, the methods of the invention refer to an amount of the modulator of the invention as described herein, in an amount sufficient to achieve modulation of the levels and/or activity of the KAI1 as-lncRNA. In yet some further embodiments, modulation of the KAI1 as-lncRNA may accordingly lead to modulation in the levels (e.g., expression and/or stability) of the KAI1 gene product, specifically as defined herein above.

It should be appreciated that "modulation" as used herein encompasses either "inhibition of the levels and/or activity of the KAI1 as-lncRNA, or alternatively, enhancement thereof.

More specifically, the terms "inhibition", "moderation", "reduction" or "attenuation" as referred to herein, relate to the retardation, restraining or reduction of the levels and/or activity of the KAI1 as-lncRNA by any one of about 1% to 99.9%, or even, 100% specifically, about 1%, 5%, 10%, 15%, 20%, 25%, 30%, 35%, 40%, 45%, 50%, 55%, 60%, 65%, 70%, 75%, 80%, 85%, 90%, 95%, 99%, 99.9% or 100%. Alternatively, the terms "increase", "augmentation" and "enhancement" as used herein relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of the levels and/or activity of the KAI1 as-lncRNA as compared to a suitable control. It should be appreciated that 10%, 50%, 120%, 500%, etc., are interchangeable with "fold change" values, i.e., 0.1, 0.5, 1.2, 5, etc., respectively. 10%, 50%, 120%, 500%, etc., are interchangeable with "fold change" values, i.e., 0.1, 0.5, 1.2, 5, etc., respectively. Therefore, the term decrease or alternatively, increase, refers to either a decrease or an increase of about 2, 3, 4, 5, 6, 7, 8, 9, 10, 20, 30, 40, 50, 60, 70, 80, 90, 100, 200, 300, 400, 500, 600, 700, 800, 900, 1000 folds or more of the levels and activity of the KAI1 as-lncRNA.

In yet some further particular embodiments, the method of the invention may lead to reduction in at least one of the levels and the activity of the KAI1 as lncRNA, thereby increasing the expression of the KAI1/CD82 gene, and the levels of the KAI1 gene product. In yet more specific embodiments, the method of the invention may lead to reduction in the level/s of the of the KAI1 as lncRNA, by either reducing transcription thereof, and/or reducing its stability (increasing its degradation). In yet some other alternative or additional embodiments, the methods of the invention may result in reduction of the activity of KAI1 as lncRNA, as discussed above.

In more specific embodiments, the method of the invention may result in at least one of reduction of cell migration, retardation of cell motility, increased cell adhesion, reduced or ablated cell invasion/metastasis and/or cell proliferation.

More specifically, cell proliferation is the process that results in an increase of the number of cells, and is defined by the balance between cell divisions and cell loss through cell death or differentiation.

Cell migration is a central process in the development and maintenance of multicellular organisms. Tissue formation during embryonic development, wound healing and immune responses require the orchestrated movement of cells in particular directions to specific locations. Cells often migrate in response to specific external signals, including chemical signals and mechanical signals.

Cells achieve active movement by several different mechanisms and generally involves drastic changes in cell shape which are driven by the cytoskeleton.

There are two models for cell migration: the cytoskeletal model and the membrane flow model. It seems that both underlying processes contribute to cell extension.

More specifically, the cytoskeletal model, rapid actin polymerization at the cell's front edge leads to the formation of actin filaments that "push" the leading edge forward. This is the main motile force for advancing the cell's front edge.

According to the membrane flow model, extension of the leading edge occurs primarily by addition of membrane at the front of the cell. The actin filaments that form at the front might stabilize the added membrane so that a structured extension, or lamella, is formed rather than a bubble-like structure (or bleb) at its front. As cell migration enhances the metastatic potential of tumor cell/s, in some embodiments, the modulators of the invention as well as methods using these modulators, inhibit cell migration and motility, as also shown by the Examples.

More specifically, Cell motility is the spontaneous movement of a cell from one location to another by consumption of energy. The term encompasses several types of motion, including swimming (or flagellar motility), crawling (or amoeboid movement), gliding and swarming. The modulators of the invention and any of the methods provided herein may in some embodiments, modulate and specifically in some embodiments inhibit any of the cell motility type discussed herein.

Still further, in some embodiments, the modulators of the invention may modulate and specifically decrease cell invasion. Cell invasion is related to cell migration, and defines the ability of cells to become motile and to navigate through the extracellular matrix within a tissue or to infiltrate neighboring tissues. Cancer cells that become invasive may disseminate to secondary sites and form metastases.

Metastasis is the spread of cancer cells to new areas of the body (often by way of the lymph system or bloodstream). A metastatic cancer, or metastatic tumor, is one which has spread from the primary site of origin (where it started) into different area(s) of the body. Tumors formed from cells that have spread are called secondary tumors. The cancer may have spread to areas near the primary site (regional metastasis), or to parts of the body that are farther away (distant metastasis).

In yet some further embodiments, the modulators and methods provided by the invention may modulate cell adhesion. Cell adhesion is the process by which cells interact and attach to a surface, substrate or another cell, mediated by interactions between molecules of the cell surface. Cell adhesion occurs from the action of transmembrane glycoproteins, called cell adhesion molecules. Examples of these proteins include selectins, integrins, syndecans, and cadherins. Cellular adhesion is essential in maintaining multicellular structure. Cancer metastasis tumors that spread through the circulatory system use mechanisms of cell adhesion to establish new tumors in the body. In yet some further embodiments, as metastatic cells tend to lose their adhesion properties, the modulators of the invention may enhance cell adhesion, thereby reduce the metastatic potential of tumor cells.

Thus, in some embodiments, using modulators of KAI1 as lncRNA as described herein, the method of the invention may lead to reduction or inhibition of cell migration, cell motility cell invasion/metastasis and/or cell proliferation. More specifically, the terms "inhibition", "moderation", "reduction" or "attenuation" as referred to herein, relate to the retardation, restraining and/or reduction of at least one of cell migration, cell motility cell invasion/metastasis and/or cell proliferation by any one of about 1% to 99.9%, or even 100%, specifically, about 1%, 5%, 10%, 15%, 20%, 25%, 30%, 35%, 40%, 45%, 50%, 55%, 60%, 65%, 70%, 75%, 80%, 85%, 90%, 95%, 99%, 99.9% or 100%.

Still further, using modulators of KAI1 as lncRNA as described herein, the method of the invention may lead to an "increase", "augmentation" and "enhancement" of cell adhesion. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of cell adhesion as compared to a suitable control. It should be appreciated that 10%, 50%, 120%, 500%, etc., are interchangeable with "fold change" values, i.e., 0.1, 0.5, 1.2, 5, etc., respectively. 10%, 50%, 120%, 500%, etc., are interchangeable with "fold change" values, i.e., 0.1, 0.5, 1.2, 5, etc., respectively. Therefore, the term increase refers to an increase of about 2, 3, 4, 5, 6, 7, 8, 9, 10, 20, 30, 40, 50, 60, 70, 80, 90, 100, 200, 300, 400, 500, 600, 700, 800, 900, 1000 folds or more.

In certain embodiments, the wound healing assay described by Example 12, provides information that relates to the migration of the cells. Adhesion to fibronectin as described in Example 13 demonstrates the adhesion of the cells and the Matrigel assay described in Example 14, demonstrates the invasion and motility of the cells.

In some specific embodiments, the cell modulated by the method of the invention may be a cell of a subject suffering from a malignant disorder.

According to some embodiments, the invention further provides modulation of the expression of the KAI1 gene in a cell in a subject in need thereof. This specific method involves the administration of the modulators of the invention to said subject.

In yet a further aspect, the invention relates to a method of treating, preventing, inhibiting, reducing, eliminating, protecting or delaying the onset or ameliorating the severity of a malignant disorder or of any KAI1 associated disorders in a subject in need thereof. More specifically, the method of the invention may comprise the step of administering to the subject a therapeutically effective amount of at least one modulator of at least one KAI1as-lncRNA, or of any vehicle, matrix, nano- or micro-particle, or a composition comprising the same. More specifically, the KAI1 as lncRNA modulated by the modulator used by the method of the invention has a length of about 700 to about 1000 nucleotides and is encoded upstream of the KAI1 gene major TSS.

In some embodiments, the modulator used by the method of the invention is as defined by the invention herein above.

In some embodiments, the method of the invention may be applicable for any malignant disorder, specifically, at least one of carcinoma, melanoma, sarcoma, lymphoma, leukemia, and myeloma.

In yet some further embodiments, such malignant disorder may be a solid tumor. A non-limiting example for a solid tumor treatable by the methods of the invention may be any carcinoma, specifically any one of breast carcinoma, prostate carcinoma, pancreatic carcinoma, non-small cell lung carcinoma, ovarian carcinoma, colorectal carcinoma, bladder carcinoma, cervical carcinoma, hepatocellular carcinoma, gastric carcinoma, laryngeal carcinoma, and cancer of the thyroid gland. In yet some further embodiments, the methods of the invention may be applicable for treating melanoma.

As indicated above, in some specific embodiments, the methods of the invention may be used for treating malignant disorders, specifically, cancer. The term "cancer" is used herein interchangeably with the term "tumor" and denotes a mass of tissue found in or on the body that is made up of abnormal cells. As used herein to describe the present invention, "metastatic disorder", "cancer", "tumor" and "malignancy" all relate equivalently to a hyperplasia of a tissue or organ as a result of a metastatic process. If the tissue is a part of the lymphatic or immune systems, malignant cells may include non-solid tumors of circulating cells. Malignancies of other tissues or organs may produce solid tumors. In general, the methods of the present invention may be applicable for treatment of a patient suffering from any one of primary, advanced or metastatic solid tumors and non-solid tumors.

Malignancy, as contemplated in the present invention may be any one of carcinomas, melanomas, sarcomas, myelomas, lymphomas and leukemia's.

Carcinoma as used herein, refers to an invasive malignant tumor consisting of transformed epithelial cells. Alternatively, it refers to a malignant tumor composed of transformed cells of unknown histogenesis, but which possess specific molecular or histological characteristics that are associated with epithelial cells, such as the production of cytokeratins or intercellular bridges. This may include, but is not limited to, carcinomas of: the GI tract, colon, lung, liver, breast, prostate, pancreas, bladder, ovary, and cervix carcinoma. The invention may be applicable as well for the treatment or inhibition of solid tumors such as tumors in lip and oral cavity, pharynx, larynx, paranasal sinuses, major salivary glands, esophagus, stomach, small intestine, colorectum, anal canal, gallbladder, lacrimal gland, extraliepatic bile ducts, ampulla of vater, exocrine pancreas, pleural mesothelioma, bone, soft tissue sarcoma, carcinoma and malignant melanoma of the skin, vulva, vagina, cervix uteri, corpus uteri, fallopian tube, gestational trophoblastic tumors, penis, testis, kidney, ureter, urethra, carcinoma of the eyelid, carcinoma of the conjunctiva.

Melanoma as used herein is a malignant tumor of melanocytes. Melanocytes are cells that produce the dark pigment, melanin, which is responsible for the color of skin. They predominantly occur in skin, but are also found in other parts of the body, including the bowel and the eye. Melanoma can occur in any part of the body that contains melanocytes, such as malignant melanoma of the conjunctiva, malignant melanoma of the uvea.

Leukemia refers to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number of abnormal cells in the blood-leukemic or aleukemic (subleukemic).

Sarcoma is a cancer that arises from transformed connective tissue cells. These cells originate from embryonic mesoderm, or middle layer, which forms the bone, cartilage, and fat tissues. This is in contrast to carcinomas, which originate in the epithelium. This may include, but is not limited to sarcoma of the orbit, brain, spinal cord, vascular system, hemangiosarcoma and Kaposi's sarcoma.

Myeloma as mentioned herein is a cancer of plasma cells, a type of white blood cell normally responsible for the production of antibodies. Collections of abnormal cells accumulate in bones, where they cause bone lesions, and in the bone marrow where they interfere with the production of normal blood cells. Most cases of myeloma also feature the production of a paraprotein, an abnormal antibody that can cause kidney problems and interferes with the production of normal antibodies leading to immunodeficiency. Hypercalcemia (high calcium levels) is often encountered.

Lymphoma is a cancer in the lymphatic cells of the immune system. Typically, lymphomas present as a solid tumor of lymphoid cells. These malignant cells often originate in lymph nodes, presenting as an enlargement of the node (a tumor). It can also affect other organs in which case it is referred to as extranodal lymphoma. Non limiting examples for lymphoma include Hodgkin's disease, non-Hodgkin's lymphomas and Burkitt's lymphoma.

Further malignancies that may find utility in the present invention can comprise but are not limited to hypoplastic and aplastic anemia (both virally induced and idiopathic), myelodysplastic syndromes, all types of paraneoplastic syndromes (both immune mediated and idiopathic) and retinoblastoma.

It should be appreciated that any of the modulators described by the invention may be applicable for treating and/or ameliorating any of the disorders disclosed herein or any condition associated therewith. It is understood that the interchangeably used terms "associated", "linked" and "related", when referring to pathologies herein, mean diseases, disorders, conditions, or any pathologies which at least one of: share causalities, co-exist at a higher than coincidental frequency, or where at least one disease, disorder condition or pathology causes the second disease, disorder, condition or pathology. More specifically, as used herein, "disease", "disorder", "condition", "pathology" and the like, as they relate to a subject's health, are used interchangeably and have meanings ascribed to each and all of such terms.

In some specific embodiments, the method of the invention may be particularly applicable for treating breast carcinoma.

In certain embodiments, the method of the invention may be particularly applicable for treating breast cancer. As used herein, the term "breast cancer" refers to a cancer that develops from breast tissue. Development of breast cancer is often associated with a lump in the breast, a change in breast shape, dimpling of the skin, fluid coming from the nipple, or a red scaly patch of skin.

Breast cancer classification divides breast cancer into categories according to different schemes, each based on different criteria and serving a different purpose. The major categories are the histopathological type, the grade of the tumor, the stage of the tumor, and the expression of proteins and genes.

The purpose of classification among others is to select the appropriate treatment regimen. For example, breast cancers that tend to be aggressive and life-threatening should be treated with aggressive treatments that have major adverse effects. Other breast cancers which are less aggressive can be treated with less aggressive treatments.

Breast cancers can be classified by criteria, each one influences treatment response and prognosis. Classification includes at least one of the following parameters: histopathological type, grade, stage (TNM), receptor status, and the presence or absence of certain receptors and markers:

Staging of breast cancer may be done by various methods for example using TNM staging which takes into account the size of the tumor (T), whether the cancer has spread to the lymph glands (lymph nodes) (N), and whether the tumor has spread anywhere else in the body (M—for metastases).

Alternatively, staging can be expressed as a number on a scale of 0 through IV—with stage 0 describing non-invasive cancers that remain within their original location and stage IV describing invasive cancers that have spread outside the breast to other parts of the body.

In some embodiments, the breast tumor is a non-invasive tumor. In some other embodiments, the breast tumor is an invasive tumor. When referring to "non-invasive" cancer it should be noted as a cancer that does not grow into or invade normal tissues within or beyond the primary location, for example the breast. Non-invasive cancers are sometimes called carcinoma in situ ("in the same place") or pre-cancers. In connection with breast cancer, non-invasive cancer stays in milk ducts or lobules in the breast. When referring to "invasive cancers" it should be noted as caner that invades and grows in normal, healthy tissues to form metastasis.

As used herein the term "metastatic cancer" or "metastatic status" refers to a cancer that has spread from the place where it first started to another place in the body and specifically to the lymph node. Such a tumor formed by metastatic cancer cells is called a metastatic tumor or a metastasis.

As used herein the term lymph node negative (LNN) refers to a primary non-invasive breast tumor that remain within the breast. The term lymph node positive (LNP) refers to a primary invasive breast tumor that has spread outside the breast into the lymph node.

It should be understood that characterization of a breast tumor as non-invasive or invasive may depend on information collected from different methods and depends on the detection capability of each one of the methods. Therefore, when referring to LNN or LNP it should be understood as detection level of the method used.

Receptor status can also be used for classification of breast cancer into several molecular classes. The three most important receptors in the classification being: estrogen receptor (ER), progesterone receptor (PR), and HER2/neu. In some embodiments, the methods of the invention may be applicable for treating breast cancer classified as a triple negative breast cancer (TNBC). More specifically, breast cancer cells tested negative for estrogen receptors (ER−), progesterone receptors (PR−), and HER2 (HER2−) means the cancer is triple-negative.

These negative results mean that the growth of the cancer is not supported by the hormones estrogen and progesterone, nor by the presence of HER2 receptors. Therefore, triple-negative breast cancer does not respond to hormonal therapy (such as tamoxifen or aromatase inhibitors) or therapies that target HER2 receptors, such as Herceptin (chemical name: trastuzumab) and the like.

The present invention relates to the treatment of subjects or patients, in need thereof. By "patient" or "subject in need" it is meant any organism who may be affected by the above-mentioned conditions, and to whom the monitoring and diagnosis methods described herein after is desired, including humans, (domestic and non-domestic mammals such as canine and feline subjects, bovine, simian, equine and murine subjects, rodents, domestic birds, aquaculture, fish and exotic aquarium fish. It should be appreciated that the subject may be also any reptile or zoo animal. More specifically, the methods of the invention are intended for mammals. By "mammalian subject" is meant any mammal for which the proposed therapy is desired, including human, livestock, equine, canine, and feline subjects, most specifically humans.

The term "treatment or prevention" as used herein, refers to the complete range of therapeutically positive effects of administrating to a subject including inhibition, reduction of, alleviation of, and relief from, a proliferative condition and illness, proliferative condition-related symptoms or undesired side effects or proliferative disorders. More specifically, treatment or prevention of relapse or re-recurrence of the disease, includes the prevention or postponement of development of the disease, prevention or postponement of development of symptoms and/or a reduction in the severity of such symptoms that will or are expected to develop. These further include ameliorating existing symptoms, preventing additional symptoms and ameliorating or preventing the underlying metabolic causes of symptoms.

It should be appreciated that the terms "inhibition", "moderation", "reduction", "decrease" or "attenuation" as referred to herein, relate to the retardation, restraining or reduction of a process by any one of about 1% to 99.9%, specifically, about 1% to about 5%, about 5% to 10%, about 10% to 15%, about 15% to 20%, about 20% to 25%, about 25% to 30%, about 30% to 35%, about 35% to 40%, about 40% to 45%, about 45% to 50%, about 50% to 55%, about 55% to 60%, about 60% to 65%, about 65% to 70%, about 75% to 80%, about 80% to 85% about 85% to 90%, about 90% to 95%, about 95% to 99%, about 99% to 99.9%, or even 100%.

With regards to the above, it is to be understood that, where provided, percentage values such as, for example, 10%, 50%, 120%, 500%, etc., are interchangeable with "fold change" values, i.e., 0.1, 0.5, 1.2, 5, etc., respectively.

Still further, the invention provides a diagnostic or prognostic method for diagnosing, determining the progression or monitoring a malignant disorder in a subject. More specifically, the method comprising: in a first step (a) determining the expression level of at least one KAI1 as lncRNA in at least one biological sample of said subject, to obtain an expression value; and (b) determining if the expression value obtained in step (a) is positive or negative with respect to a predetermined standard expression value or to an expression value of said KAI1 as lncRNA in at least one control sample.

It should be noted that (i) a positive expression value of said KAI1 as lncRNA in said sample, indicates that the subject belongs to a pre-established population associated with a positive metastatic status of said malignant disorder; and (ii) a negative expression value of said KAI1 as lncRNA in said sample, indicates that said subject belongs to a pre-established population associated with a negative metastatic status of said malignant disorder. In yet some other embodiments, the diagnostic methods of the invention may involve the steps of determining the expression level of at least one KAI1 as lncRNA in at least one biological sample and optionally in at least one control sample (e.g., positive sample obtained from a subject suffering from a malignant disorder, negative sample of a healthy subject or a subject that is not suffering from a malignant disorder), and comparing the levels of KAI1 as lncRNA in the tested sample with the controls levels or control expression values. In some embodiments, expression of KAI1 as lncRNA that is higher as compared to a healthy control sample, indicates that the tested subject is suffering from a malignant disorder.

In accordance with some embodiments, in the first step (a) of the method of the invention, the expression level of at least one of the KAI1 as-lncRNA described herein is being determined. The terms "level of expression" or "expression level" are used interchangeably and generally refer to a numerical representation of the amount (quantity) of a nucleic acid product in a biological sample. In some embodiments, the "level of expression" or "expression level" refers to the numerical representation of the amount (quantity) of polynucleotide which may be gene in a biological sample.

"Expression" generally refers to the process by which gene-encoded information is converted into the structures present and operating in the cell. For example, the expression may be measured at the nucleic acid level, by hybridization to DNA microarrays, via RNA-seq. or for example using Real-Time Polymerase Chain Reaction, which in the case of RNA is also referred to as RT-PCR or RT-quantitative PCR (RT-qPCR or qRT-PCR). The luminosity in case of RT-PCR, or any other tag is captured by a detector that converts the signal intensity into a numerical representation which is said expression value, in terms of biomarker as-lncRNA.

Therefore, according to the invention "expression" of a gene, specifically, any of the KAI1 as-lncRNA of the invention may refer to transcription into a polynucleotide. Fragments of the transcribed polynucleotide shall also be regarded as expressed whether they originate from a transcript generated by alternative splicing or a degraded transcript. Methods for determining the level of expression of the KAI1as-lncRNA of the invention will be described in more detail herein after. It should be appreciated that the methods of the invention, as well as the compositions and kits disclosed herein after, refer to the level of the KAI1as-lncRNA in the sample. It should be understood that the level of the as-lncRNA reflects the level of expression (transcription), but also reflects the stability of the KAI1as-lncRNA.

In certain and specific embodiments, the method of the invention further comprises an additional and optional step of normalization. According to this embodiment, in addition to determination of the level of expression of the KAI1as-lncRNA of the invention, the level of expression of at least one suitable control reference as-lncRNA, or alternatively, other controls such as cytoplasmic HPRT1 or the TBP transcript, is being determined.

The term "expression value" refers to the result of a calculation, that uses as an input the "level of expression" or "expression level" obtained experimentally and by normalizing the "level of expression" or "expression level" by at least one normalization step as detailed herein, the calculated value termed herein "expression value" is obtained.

More specifically, as used herein, "normalized values" are the quotient of raw expression values of marker KAI1as-lncRNAs, divided by the expression value of a control reference of either as-lncRNA or another stable RNA/mRNA from the same sample. Any assayed sample may contain more or less biological material than is intended, due to human error and equipment failures. Importantly, the same error or deviation applies to both the KAI1 as-lncRNA of the invention and to the control reference be it cytoplasmic/nuclear mRNA or nuclear as-lncRNA, whose expression is essentially constant. Thus, division of the KAI1 as-lncRNA raw expression value by the control reference raw expression value yields a quotient which is essentially free from any technical failures or inaccuracies (except for major errors which destroy the sample for testing purposes) and constitutes a normalized expression value of said KAI1as-lncRNA. This normalized expression value may then be compared with normalized cutoff values, i.e., cutoff values calculated from normalized expression values.

Normalized KAI1as-lncRNA expression level values that are higher (positive) or lower (negative) in comparison with a corresponding predetermined standard expression value or a cut-off value in a control sample predict to which population of patients the tested sample belongs or more specifically the disease stage, or the metastatic status of the subject.

It should be appreciated that an important step in the method of the inventions is determining whether the normalized expression value of any one of the KAI1 as-lncRNA is changed compared to a pre-determined cut off, or is within the range of expression of such cutoff.

More specifically, as noted above, after determining the expression values of KAI1 as-lncRNA of the invention, the next step of the method of the invention involves calculating and determining if the expression value obtained in step (a) is any one of positive or negative with respect to a predetermined standard expression value or to an expression value of said KAI1as-lncRNA in at least one control sample. Such step involves calculating and measuring the difference between the expression values of the examined sample and the cutoff value pre-determined for a certain population and determining whether the examined sample can be defined as positive or negative, with respect to said population. In some particular and non-limiting embodiments, a control sample or control expression value, standard expression value or expression value of said KAI1as-lncRNA in at least one control sample, may be calculated using cell lines, specifically, cancerous cell lines, more specifically, non-invasive cancer cell lines. In one specific and non-limiting embodiments, a non-invasive cancer cell line that may be applicable as control sample in the diagnostic method of the invention may be the MCF-7 cell line. Alternatively, the control sample may be derived from healthy adjacent tissue from the same individual, or other individuals having either primary tumor or no malignancy at all; the latter certainly in cases where the affected patient tissue harbors primary tumor.

In yet more specific embodiments, the second step (b) of the method of the invention involves comparing the expression values determined for the tested sample with predetermined standard values or cutoff values, or alternatively, with expression values of at least one control sample. As used herein the term "comparing" denotes any examination of the expression level and/or expression values obtained in the samples of the invention as detailed throughout in order to discover similarities or differences between at least two different samples. It should be noted that in some embodiments, comparing according to the present invention encompasses the possibility to use a computer based approach.

As described hereinabove, the method of the invention refers to a predetermined cutoff value/s. It should be noted that a "cutoff value", sometimes referred to simply as "cutoff" herein, is a value that meets the requirements for both high diagnostic sensitivity (true positive rate) and high diagnostic specificity (true negative rate).

It should be appreciated that "Standard" or a "predetermined standard" as interchangeably used herein, denotes either a single standard value or a plurality of standards with which the level at least one of the KAI1as-lncRNA expression from the tested sample is compared. The standards may be provided, for example, in the form of discrete numeric values or is calorimetric in the form of a chart with different colors or shadings for different levels of expression; or they may be provided in the form of a comparative curve prepared on the basis of such standards (standard curve).

In certain embodiments, the detection step further involves detecting a signal from the detecting molecules that correlate with the expression level of at least one of the KAI1as-lncRNA and in the sample from the subject, by a suitable means. According to some embodiments, the signal detected from the sample by any one of the experimental methods detailed herein below reflects the expression level of at least one of the KAI1 as-lncRNA. It should be noted that such signal-to-expression level data may be calculated and derived from a calibration curve.

Thus, in certain embodiments, the method of the invention may optionally further involve the use of a calibration curve created by detecting a signal for each one of increasing pre-determined concentrations of at least one of the KAI1 as-lncRNAs. Obtaining such a calibration curve may be indicative to evaluate the range at which the expression levels correlate linearly with the concentrations of at least one of the KAI1 as-lncRNAs. It should be noted in this connection that at times when no change in expression level of at least one of the KAI1 as-lncRNA is observed, the calibration curve should be evaluated in order to rule out the possibility that the measured expression level is not exhibiting a saturation type curve, namely a range at which increasing concentrations exhibit the same signal.

It must be appreciated that in certain embodiments such calibration curve as described above may be also part or component in any of the kits provided by the invention as described herein after.

In some embodiments, determining the level of expression of the at least one at KAI1 as-lncRNA in step (a) of the method of the invention is performed by the step of contacting at least one detecting molecule or any combination or mixture of plurality of detecting molecules with a biological sample of said subject, or with any nucleic acid product obtained therefrom. It should be noted that each of the detecting molecules is specific for one of said at least one KAI1as-lncRNA.

In more specific embodiments, detecting molecules applicable in the diagnostic methods of the invention may be a nucleic acid detecting molecule comprising isolated oligonucleotide/s, each oligonucleotide specifically hybridizes to a nucleic acid sequence of said at least one KAI1as-lncRNA.

In more specific embodiments, the detecting molecule/s used by the diagnostic method of the invention may be at least one of a pair of primers, at least one primer, nucleotide probes or any combinations thereof.

As noted above, in the first step of the method of the invention, the sample or any protein or nucleic acid obtained therefrom, is contacted with the detecting molecules of the invention.

As used herein, "nucleic acid molecules", "nucleic acid sequence", "nucleic acids", "sequence" are interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. It should be further noted that "base pair/s" or as abbreviated herein "bp" relates to pairs of nucleotides connecting the complementary strands of a molecule of DNA or RNA and consisting of a purine linked to a pyrimidine by hydrogen bonds. The base pairs are adenine-thymine and guanine-cytosine in DNA, and adenine-uracil and guanine-cytosine in RNA or in hybrid DNA-RNA pairing. However, it should be appreciated that in certain and specific embodiments the term "bp" or "base pair" as used herein may also encompass a single nucleotide of a single strand nucleic acid sequence. Still further, as used herein, the term "nucleic acid(s)" also includes DNAs or RNAs as described above that contain one or more modified bases. Thus, DNAs or RNAs with bases or backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations.

As used herein, the term "oligonucleotide" is defined as a molecule comprised of two or more deoxyribonucleotides and/or ribonucleotides, and preferably more than three. Its exact size will depend upon many factors which in turn, depend upon the ultimate function and use of the oligonucleotide. The oligonucleotides may be from about 3 to about 1,000 nucleotides long. Although oligonucleotides of 5 to 100 nucleotides are useful in the invention, preferred oligonucleotides range from about 5 to about 15 bases in length, from about 5 to about 20 bases in length, from about 5 to about 25 bases in length, from about 5 to about 30 bases in length, from about 5 to about 40 bases in length or from about 5 to about 50 bases in length. More specifically, the detecting oligonucleotides molecule used by the composition of the invention may comprise any one of 5, 6, 7, 8, 9, 10, 11, 12, 13, 14, 15, 16, 17, 18, 19, 20, 21, 22, 23, 24, 25, 26, 27, 28, 29, 30, 35, 40, 45, 50 bases in length. It should be further noted that the term "oligonucleotide" refers to a single stranded or double stranded oligomer or polymer of ribonucleic acid (RNA) or deoxyribonucleic acid (DNA) or mimetics thereof. This term includes oligonucleotides composed of naturally-occurring bases, sugars and covalent internucleoside linkages (e.g., backbone) as well as oligonucleotides having non-naturally-occurring portions which function similarly.

In some specific embodiments, where the detecting molecules of the invention are nucleic acid based molecules, optional detecting molecule/s may be at least one nucleic acid aptamer specific for the at least one of said KAI1 as-lncRNA. As used herein the term "aptamer" or "specific aptamers" denotes single-stranded nucleic acid (DNA or RNA) molecules which specifically recognizes and binds to a target molecule. The aptamers according to the invention may fold into a defined tertiary structure and can bind a specific target molecule with high specificities and affinities.

Thus, it should be further appreciated that the methods, as well as the compositions and kits of the invention may comprise, as an oligonucleotide-based detection molecule, both primers and probes.

The term "primer" as used herein refers to an oligonucleotide, whether occurring naturally as in a purified restriction digest, or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be single-stranded or double-stranded and must be sufficiently long to prime the synthesis of the desired extension product in the presence of the inducing agent. The exact length of the primer will depend upon many factors, including temperature, source of primer and the method used. For example, for diagnostic applications, depending on the complexity of the target sequence, the oligonucleotide primer typically contains 10-30 or more nucleotides, although it may contain fewer nucleotides. More specifically, the primer used by the methods, as well as the compositions and kits of the invention may comprise 10, 11, 12, 13, 14, 15, 16, 17, 18, 19, 20, 21, 22, 23, 24, 25, 26, 27, 28, 29 or 30 nucleotides or more. In certain embodiments, such primers may comprise 30, 40, 50, 60, 70, 80, 90, 100 nucleotides or more. In specific embodiments, the primers used by the method of the invention may have a stem and loop structure. The factors involved in determining the appropriate length of primer are known to one of ordinary skill in the art and information regarding them is readily available.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe may be 5, 6, 7, 8, 9, 10, 11, 12, 13, 14, 15, 16, 17, 18, 19, 20, 21, 22, 23, 24, 25, 26, 27, 28, 29 and up to 30 nucleotides in length as long as it is less than the full length of the target RNA or any gene encoding said RNA. Probes can include oligonucleotides modified so as to have a tag which is detectable by fluorescence, chemiluminescence and the like. The probe can also be modified so as to have both a detectable tag and a quencher molecule, for example TaqMan® and Molecular Beacon® probes.

The oligonucleotides and analogs thereof may be RNA or DNA, or analogs of RNA or DNA, commonly referred to as antisense oligomers or antisense oligonucleotides. Such RNA or DNA analogs comprise, but are not limited to, 2'-0-alkyl sugar modifications, methylphosphonate, phosphorothiate, phosphorodithioate, formacetal, 3-thioformacetal, sulfone, sulfamate, and nitroxide backbone modifications, and analogs, for example, LNA analogs, wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs. Probes may also be mixtures of any of the oligonucleotide analog types together or in combination with native DNA or RNA. At the same time, the oligonucleotides and analogs thereof may be used alone or in combination with one or more additional oligonucleotides or analogs thereof.

According to this option, the expression level may be determined using amplification assay. The term "amplification assay", with respect to nucleic acid sequences, refers to methods that increase the representation of a population of nucleic acid sequences in a sample. Nucleic acid amplification methods, such as PCR, isothermal methods, rolling circle methods, etc., are well known to the skilled artisan. More specifically, as used herein, the term "amplified", when applied to a nucleic acid sequence, refers to a process whereby one or more copies of a particular nucleic acid sequence is generated from a template nucleic acid, preferably by the method of polymerase chain reaction.

"Polymerase chain reaction" or "PCR" refers to an in vitro method for amplifying a specific nucleic acid template sequence. The PCR reaction involves a repetitive series of temperature cycles and is typically performed in a volume of 50-100 microliter. The reaction mix comprises dNTPs (each of the four deoxynucleotides dATP, dCTP, dGTP, and dTTP), primers, buffers, DNA polymerase, and nucleic acid template. The PCR reaction comprises providing a set of polynucleotide primers wherein a first primer contains a sequence complementary to a region in one strand of the nucleic acid template sequence and primes the synthesis of a complementary DNA strand, and a second primer contains a sequence complementary to a region in a second strand of the target nucleic acid sequence and primes the synthesis of a complementary DNA strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers", "a set of PCR primers" or "pair of primers" can comprise two, three, four or more primers.

Real time nucleic acid amplification and detection methods are efficient for sequence identification and quantification of a target since no pre-hybridization amplification is required. Amplification and hybridization are combined in a single step and can be performed in a fully automated, large-scale, closed-tube format.

Methods that use hybridization-triggered fluorescent probes for real time PCR are based either on a quench-release fluorescence of a probe digested by DNA Polymerase (e.g., methods using TaqMan®, MGB-TaqMan®), or on a hybridization-triggered fluorescence of intact probes (e.g., molecular beacons, and linear probes). In general, the probes are designed to hybridize to an internal region of a PCR product during annealing stage (also referred to as amplicon). For those methods utilizing TaqMan® and MGB-TaqMan® the 5'-exonuclease activity of the approaching DNA Polymerase cleaves a probe between a fluorophore and a quencher, releasing fluorescence.

Thus, a "real time PCR" or "qRT-PCR" assay provides dynamic fluorescence detection of amplified KAI1 as-lncRNA of the invention or any control reference gene produced in a PCR amplification reaction. During PCR, the amplified products created using suitable primers hybridize to probe nucleic acids (TaqMan® probe, for example), which may be labeled according to some embodiments with both a reporter dye and a quencher dye. When these two dyes are in close proximity, i.e. both are present in an intact probe oligonucleotide, the fluorescence of the reporter dye is suppressed. However, a polymerase, such as AmpliTaq Gold™, having 5'-3' nuclease activity can be provided in the PCR reaction. This enzyme cleaves the fluorogenic probe if it is bound specifically to the target nucleic acid sequences between the priming sites. The reporter dye and quencher dye are separated upon cleavage, permitting fluorescent detection of the reporter dye. Upon excitation by a laser provided, e.g., by a sequencing apparatus, the fluorescent signal produced by the reporter dye is detected and/or quantified. The increase in fluorescence is a direct consequence of amplification of target nucleic acids during PCR.

More particularly, qRT-PCR or "qPCR" (Quantitative RT-PCR), which is quantitative in nature, can also be performed to provide a quantitative measure of gene expression levels. In qRT-PCR reverse transcription and PCR can be performed in two steps, or reverse transcription combined with PCR can be performed. One of these techniques, for which there are commercially available kits such as TaqMan® (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe attached to the 5' end of the oligonucleotide. Different fluorescent markers are attached to different reporters, allowing for measurement of at least two products in one reaction.

When Taq DNA polymerase is activated, it cleaves off the fluorescent reporters of the probe bound to the template by virtue of its 5-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in any solid support, for example, slides, microplates, 96 well plates, 384 well plates and the like so that samples derived from many individuals are processed and measured simultaneously. The TaqMan® system has the additional advantage of not requiring gel electrophoresis and allows for quantification when used with a standard curve.

A second technique useful for detecting PCR products quantitatively without is to use an intercalating dye such as the commercially available QuantiTect SYBR Green PCR (Qiagen, Valencia Calif.). qRT-PCR is performed using SYBR green as a fluorescent label which is incorporated into the PCR product during the PCR stage and produces fluorescence proportional to the amount of PCR product.

Both TaqMan® and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other known systems to quantitatively measure RNA expression products include Molecular Beacons® which uses a probe having a fluorescent molecule and a quencher molecule, the probe capable of forming a hairpin structure such that when in the hairpin form, the fluorescence molecule is quenched, and when hybridized, the fluorescence increases giving a quantitative measurement of gene expression.

According to some embodiments, the method of the invention may use as a sample any one of a biological sample of organ/s, cell/s or tissue/s body fluid or a blood sample. In further specific embodiments a sample may be a tumor sample. In more particular embodiments, the methods of the invention may use a metastatic breast tumor sample.

As used herein, the term "sample" refers to organ, sub-cellular compartments thereof, tissue or cells. The tissue may be a whole tissue, or selected parts of a tissue. Tissue parts can be isolated by micro-dissection of a tissue, or by biopsy, or by enrichment of sub-cellular compartments. The term "sample" further refers to healthy as well as diseased or pathologically changed cells or tissues. Hence, the term further refers to a cell or a tissue associated with a disease, such a tumor, in particular carcinoma, breast cancer, and more specifically invasive breast cancer. A sample can also be cells that are placed in or adapted to tissue culture. In some embodiments, a sample may also be a blood, body fluid such as plasma, lymph, urine, saliva, serum, cerebrospinal fluid, seminal plasma, pancreatic juice, breast milk, or lung lavage. A sample can additionally be a cell or tissue from any species, including prokaryotic and eukaryotic species, specifically, humans. A tissue sample can be further a fractionated or preselected sample, if desired, preselected or fractionated to contain or be enriched for particular cell types. The sample can be fractionated or preselected by a number of known fractionation or pre selection techniques. A sample can also be any extract of the above. The term also encompasses protein fractions or alternatively, nucleic acid from cells or tissue. Thus, in some specific embodiments, the sample may be any one of a biological sample of organ/s, tissue/s, cells, body fluids and a blood sample. In yet some other embodiments, the sample may be a metastatic tumor sample.

In certain embodiments, the diagnostic method of the invention may further comprise the step of (c) administering to a subject displaying a positive expression value of KAI1 as-lncRNA as determined in step (b), a therapeutically effective amount of at least one modulator of at least one KAI1 as-lncRNA, or any vehicle, matrix, nano- or micro-particle, or a composition comprising the same. It should be noted that the KAI1 as-lncRNA modulated by the modulator used by the method of the invention has a length of about 700 to about 1000 nucleotides and is encoded upstream of the KAI1 gene TSS, specifically, the major TSS.

In further specific embodiments, the method may use any of the modulators of the invention as described herein before.

In yet a further aspect, the invention provides a kit comprising:

(a) at least one detecting molecule specific for determining the level of expression of at least one KAI1 as-lncRNA in a biological sample. In some specific embodiments, the kit of the invention may optionally further comprise at least one of: (b) pre-determined calibration curve/s or predetermined standard/s providing standard expression values of said at least one KAI1 as-lncRNA; and (c) at least one control sample.

According to one specific embodiment, the kit of the invention comprises detecting molecules, specific for detecting and determining the level of expression of KAI1 as-lncRNA. in some embodiments, such detecting molecules may be isolated oligonucleotides, each oligonucleotide specifically hybridize to a nucleic acid sequence of within said KAI1 as-lncRNA. More specifically, such detecting molecules may be at least one of pair of primer/s at least one primer, and/or nucleotide probes.

According to specific embodiments, the kit of the invention may further comprise at least one reagent for conducting a nucleic acid amplification based assay that may be at least one of a Real-Time PCR, PCR, and in situ Hybridization.

Still further, such detecting molecule may be at least one of a pair of primers or nucleotide probes.

In some embodiments, the inventors consider the kit of the invention in compartmental form. It should be therefore noted that the detecting molecules used for detecting the expression levels of the KAI1 as-lncRNA of the invention may be provided in a kit attached to an array. As defined herein, a "detecting molecule array" or "nucleic acids array", refer to a plurality of detection molecules that may be nucleic acids based or protein based detecting molecules (specifically, probes, primers and antibodies), optionally attached to a support where each of the detecting molecules is attached to a support in a unique pre-selected and defined region (e.g., an array). For example, an array may be a plurality of vessels (test tubes), plates, micro-wells in a micro-plate, each containing different detecting molecules, specifically, probes, primers and the like. An array may also be any solid support holding in distinct regions (dots, lines, columns) different and known, predetermined detecting molecules.

In some embodiments, the polynucleotide-based detection molecules of the invention may be in the form of nucleic acid probes which can be spotted onto an array to measure RNA from the sample of a subject to be diagnosed.

As defined herein, a "nucleic acid array" refers to a plurality of nucleic acids (or "nucleic acid members"), optionally attached to a support where each of the nucleic acid members is attached to a support in a unique pre-selected and defined region. These nucleic acid sequences are used herein as detecting nucleic acid molecules. In one embodiment, the nucleic acid member attached to the surface of the support is DNA. In a preferred embodiment, the nucleic acid member attached to the surface of the support is either cDNA or oligonucleotides. In another embodiment, the nucleic acid member attached to the surface of the support is cDNA synthesized by polymerase chain reaction (PCR). In another embodiment, a "nucleic acid array" refers to a plurality of unique nucleic acid detecting molecules attached to nitrocellulose or other appropriate membranes. For oligonucleotide-based arrays, the selection of oligo-nucleotides corresponding to the gene of interest which are useful as probes is well understood in the art.

As indicated above, assay based on micro array or RT-PCR may involve attaching or spotting of the probes in a solid support. As used herein, the terms "attaching" and "spotting" refer to a process of depositing a nucleic acid onto a substrate to form a nucleic acid array such that the nucleic acid is stably bound to the substrate via covalent bonds, hydrogen bonds or ionic interactions.

As used herein, "stably associated" or "stably bound" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" or "solid support", when referring to an array, provided by the kits of the invention, refer to a material having a rigid or semi-rigid surface. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly) vinylidendi-finoride, polystyrene, polycarbonate, a charged membrane, such as nylon or nitrocellulose, or combinations thereof. Preferably, at least one surface of the substrate will be substantially flat. The support may optionally contain reactive groups, including, but not limited to, carboxyl, amino, hydroxyl, thiol, and the like. In one embodiment, the support may be optically transparent. As noted above, the solid support may include polymers, such as polystyrene, agarose, sepharose, cellulose, glass, glass beads and magnetizable particles of cellulose or other polymers. The solid-support can be in the form of large or small beads, chips or particles, tubes, plates, or other forms.

It should be further appreciated that any of the reagents, substances or ingredients included in any of the methods and kits of the invention may be provided as reagents embedded, linked, connected, attached, placed or fused to any of the solid support materials described above.

Still further aspects provided by the invention relate to a method of screening for an anti-metastatic compound that inhibits, reduces or eliminates cell invasion and metastasis, the method comprising: (a) obtaining a candidate compound that reduces or inhibits the expression level of KAI1 as-lncRNA; (b) determining the effect of the compound selected in step (a), on at least one of cell migration, cell motility, and cell proliferation and cell adhesion. It should be noted that inhibition of cell migration and/or cell motility and enhancement of cell adhesion is indicative of the anti-metastatic activity of said compound. It should be further noted that inhibition of cell proliferation refers primarily to tumor cells.

Still further, the invention provides a therapeutic effective amount of the modulator of the invention as described herein before, or any vehicle, matrix, nano- or micro-particle, or a composition comprising the same, for use in a method of treating, preventing, inhibiting, reducing, eliminating, protecting or delaying the onset of a malignant disorder in a subject in need thereof.

In yet some further aspects, the invention provides the use of a therapeutic effective amount of the modulator of the invention or any vehicle, matrix, nano- or micro-particle thereof in the preparation of a composition for treating, preventing, inhibiting, reducing, eliminating, protecting or delaying the onset of a malignant disorder in a subject in need thereof.

Still further, the invention provides in some alternative embodiments thereof a modulator as described herein that increases the levels and/or the activity of KAI1 as-lncRNA, thereby reducing the expression of the KAI1/CD82 gene.

More specifically, the terms "increase", "augmentation" and "enhancement" as used herein in connection with the level and/or activity of KAI1 as-lncRNA relate to the act of becoming progressively greater in size, amount, number, or intensity. Particularly, an increase of 10%, 15%, 20%, 25%, 30%, 35%, 40%, 45%, 50%, 55%, 60%, 65%, 70%, 75%, 80%, 85%, 90%, 95%, 100%, 200%, 300%, 400%, 500%, 600%, 70%, 800%, 900%, 1000% or more of levels and/or the activity of KAI1 as-lncRNA as compared to a suitable control.

In certain embodiments, such modulator may be particularly used in a method for wound healing in a subject in need thereof.

The invention further provides at least one KAI1 as-lncRNA for use in a method for wound or injury healing in a subject in need thereof. More specifically, wherein said KAI1 as-lncRNA has a length of about 700 to about 1000 nucleotides and is encoded upstream of the KAI1/CD82 gene TSS, specifically, the major TSS.

It should be appreciated that wound or injury healing (or cicatrisation) as referred herein relates to an intricate process in which the skin or another organ-tissue repairs itself after injury. In normal skin, the epidermis (outermost layer) and dermis (inner or deeper layer) exist in steady-state equilibrium, forming a protective barrier against the external environment. Once the protective barrier is broken, the normal (physiologic) process of wound healing is immediately set in motion. The classic model of wound healing is divided into three or four sequential, yet overlapping, phases: (1) hemostasis, (2) inflammatory, (3) proliferative and (4) remodeling. Upon injury to the skin, a set of complex biochemical events takes place in a closely orchestrated cascade to repair the damage. Within minutes post-injury, platelets (thrombocytes) aggregate at the injury site to form a fibrin clot. This clot acts to control active bleeding (hemostasis). In the inflammatory phase, bacteria and debris are phagocytosed and removed, and factors are released that cause the migration and division of cells involved in the proliferative phase. The proliferative phase is characterized by angiogenesis, collagen deposition, granulation tissue formation, epithelialization, and wound contraction. In angiogenesis, new blood vessels are formed by vascular endothelial cells. In fibroplasia and granulation tissue formation, fibroblasts grow and form a new, provisional extracellular matrix (ECM) by excreting collagen and fibronectin. Concurrently, re-epithelialization of the epidermis occurs, in which epithelial cells proliferate and 'crawl' atop the wound bed, providing cover for the new tissue.

In contraction, the wound is made smaller by the action of myofibroblasts, which establish a grip on the wound edges and contract themselves using a mechanism similar to that in smooth muscle cells. When the cells' roles are close to complete, unneeded cells undergo apoptosis.

In the maturation and remodeling phase, collagen is remodeled and realigned along tension lines and cells that are no longer needed are removed by apoptosis.

The modulators of the invention may therefore enhance any of the indicated phases of wound healing as discussed above. In yet some further embodiments, the 5' terminus of said KAI1 as-lncRNA is located in an antisense orientation at position −386 of the KAI1 gene transcription start site (TSS).

In yet more specific embodiments, the KAI1 as-lncRNA may be 792 nucleotides long.

Still further, the invention provides at least one KAI1 as-lncRNA for use wherein the KAI1 as-lncRNA is the human KAI1 as-lncRNA.

In more specific embodiments, the human KAI1 as-lncRNA comprises a nucleic acid sequence as denoted by SEQ ID NO: 46, or any fragments, homologs or variants thereof.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated herein above and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and Claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures
Cell Culture

The cell lines MDA-MB-231, MCF-7 and HEK293T were received from Prof. L. Vardimon, R. Pinkas, and Y. Shiloh, respectively (Tel Aviv University). Hs578T was obtained directly from ATCC, while MDA-MB-435 was received from Prof. J. Price (MD Anderson, Houston), and SUM149PT from Prof. J. Hoheisel (DKFZ, Heidelberg). Cell line authentication was performed by determination of their short tandem repeat (STR) profile (Promega PowerPlex 16 HS kit). The cells were also routinely checked for *mycoplasma* with EZ-PCR Test Kit (Biological Industries, Israel). The cell lines were cultured at 37° C. in 5% CO2 in full Dulbecco's modified Eagle medium (DMEM) supplemented with 10% fetal bovine serum (FBS) (Sigma-Aldrich), 4 mM L-glutamine, sodium bicarbonate (Biological Industries), 10 units/ml of penicillin and 50 µg/ml streptomycin. HEK293T human embryonic kidney cells were kept under G418 antibiotic selection pressure to maintain the SV40 large T-Antigen for increased production of replicons harboring SV40 origin. Culture medium for lentiviral transduced cells was supplemented with puromycin as a selective drug.

Transient Transfection of HEK293T Cells

For transfection, HEK293T cells were seeded a day ahead in 100 mm culture dishes at a density of ~3×10$^6$/plate in DMEM containing 10% FBS. The next day the 80% confluent cells were detached with trypsin-EDTA from the culture dish. Transient transfection was carried out using jetPEI transfection reagent (Polyplus Transfection). Briefly, jetPEI (40µ) in 150 mM NaCl solution was dropped on 4 µg plasmid DNA in 150 mM NaCl solution, mixed vigorously and let stand for 15 min to form complexes. After 15 min of incubation, the detached HEK293T cells were added to the transfection DNA-jetPEI complex and immediately seeded in a 60 mm culture dish and placed in a $CO_2$ incubator, overnight. The next day the medium (DMEM+10% FBS) was refreshed. If induction or selection of the transfected DNA for stable transfectants was desired, 2.5 µg/µl doxycycline and/or 0.1-1 µg/ml puromycin were added 24 hours post transfection, respectively. For transient functional assays cells were harvested 48-72 hours post transfection.

Transient Transfection with Lipofectamin 2000 of MDA-MB-231 and MCF-7 Cells

Cells were seeded one day prior to transfection in 6-well plates. The next day the ~90% confluent cells were transfected with 2.5 ug DNA/well mixed with Lipofectamin 2000 (Thermo Fisher Scientific) according to the manufacturer instructions.

Luciferase Reporter Assay

The pGL3-basic Vector (Promega) was digested with SmaI and blunt-end ligated with the PCR amplified (Q5 polymerase) 1198 bp KAI1 promoter-enhancer region in sense and antisense orientations (having nucleic acid sequences denoted by SEQ ID NO: 20 and SEQ ID NO: 21, respectively). The pGL3-basic, pGL3-basic-promoter sense and pGL3-basic-promoter antisense were co-transfected with TK-*Renilla* (Promega) in a 1:20 ratio, respectively. Post transfection (48 hours) cells were harvested and lysed in 1× passive lysis buffer. Firefly luciferase- and *Renilla* luciferase activity were measured by a 1250 Luminometer using the Dual-Luciferase Reporter Assay System (Promega), according to manufacturer's instructions. The nucleic acid sequences denoted by SEQ ID NO: 20 and SEQ ID NO: 21 are indicated in the appended sequence listing.

PlasmidspGEM®-T Easy Cloning

PCR products amplified with Taq-polymerase, which leaves a thymine, adenine (TA)-overhang, were ligated with T4 DNA Ligase into pre-digested 50 ng pGEM®-T Easy vector (Promega), according to manufacturer's instructions. Afterwards the ligation mixture was either transformed into $CaCl_2$-competent *E. coli* or electroporated into electrocompetent *E. coli* cells.

TRIPZ-Plamids

The inducible Lentiviral Vector TRIPZ (Open Biosystem Inc.) served as expression vector for the following shRNAs: shRNA non-silencing (having the nucleic acid sequence denoted by SEQ ID NO: 3, namely ATCTCGCTTGGGCGAGAGTAAG representing the 22 bases no target-like sequence present in the shRNA non-silencing) and the shRNA termed herein shRNA-1 (having the nucleic acid sequence shown below and denoted by SEQ ID NO: 4 and directed against KAI1 as-lncRNA). TRIPZ-Plasmid expressing shRNA-1 is termed herein "TRIPZ-shRNA-1".

The shRNA-1 was designed against the KAI1 as-lncRNA. Briefly, shRNA-1 directed against the KAI1 lncRNA was designed using an algorithm that predicts a secondary structure for a given sequence, based on which exposed regions of sequence are predicted as potential targets for shRNA mediated hybridization-cleavage.

The 97 bases shRNA-1 sequence denoted by SEQ ID NO: 4 (synthesized by SIGMA) having the nucleic acid sequence:

5'-GCTGTTGACAGTGAGCGCACAACT-CATGGGTACTCTCGTTAGTGAAGCCA CAGATGTAACGAGAGTACCCATGAGTTGTGTGCC-TACTGCCTCGGA-3' contained the 21 bases target-like sequence (the actual sequence is present in the 792 bp long KAI1 as-lncRNA) ACAACTCATGGGTACTCTCGT (denoted by SEQ ID NO: 5) and its inverted repeat (guide) sequence ACGAGAGTACCCATGAGTTGT (denoted by SEQ ID NO: 6), which are separated by a 19 nucleotide hairpin loop TAGTGAAGCCACAGATGTA (denoted by SEQ ID NO: 7) and flanked by mir-30 sequences TGCTGTTGACAGTGAGCGC and GTGCC-TACTGCCTCGGA (denoted by SEQ ID NO: 8 and SEQ ID NO: 9) at both ends (as indicated in SEQ ID NO: 4 DNA sequence above).

The 97 bp sequence was amplified by PCR using pfu Polymerase (Fermentas) with the following primers, containing XhoI or EcoRI restriction sites in their overhang, respectively:

```
TRIPZ-XhoI:
                          (denoted by SEQ ID NO: 10)
CAGAAGGCTCGAGAAGGTATATTGCTGTTGACAGTGAGCG
and TRIPZ-EcoRI:
                          (denoted by SEQ ID NO: 11)
CTAAAGTAGCCCCTTGAATTCCGAGGCAGTAGGCA.
```

The amplified product and the lentiviral vector TRIPZ were both digested with XhoI and EcoRI and ligated using T4-DNA ligase. TRIPZ-shRNA-1 plasmid was then transformed into $CaCl_2$-competent *E. coli* cells. After Plasmid preparation, the insert was sequenced for confirmation.

TRIPZ as Expression Vector

The TRIPZ expression vector also served as an expression system for the following fragments: the KAI1 Open Reading Frame (ORF) in sense orientation (having a nucleic acid sequence denoted by SEQ ID NO: 1) and the KAI1 Open Reading Frame (ORF) in antisense orientation (having a nucleic acid sequence denoted by SEQ ID NO: 2) prepared as described below. The nucleic acid sequences denoted by SEQ ID NO: 1 and SEQ ID NO: 2 are indicated in the appended sequence listing. The KAI1 ORF sequence was prepared as follows: MDA-MB-231 total RNA was reverse transcribed with Oligo dT primer and amplified by Q5 Polymerase (NEB) with KAI1 cDNA specific primers: KAI1 ORF Forw. having the sequence ATGGGCTCAGCCTGTATCAAAG denoted by SEQ ID NO: 12 and KAI1 ORF Rev. having the sequence TCAGTACTTGGGGACCTTGCTG denoted by SEQ ID NO: 13.

The PCR product was purified using NucleoSpin Gel Extraction Kit (Macherey-Nagel) according to the supplier's instructions.

In order to clone the 804 bp sequence (full length cDNA of KAI1 ORF) into pTRIPZ, the selection marker turboRFP and the shRNA-non-silencing had to be excised out to facilitate the virus packaging. Therefore, the TRIPZ-shRNA non-silencing vector was digested with EcoRI and AgeI and ligated with an adapter containing the restriction site snaBI, flanked by AgeI and EcoEI protruding ends as denoted by SEQ ID NOs. 14 and 15, respectively. The adapter consisted of oligonucleotides having the sequences 5'-CCGGTGTACGTACG-3' (upper strand denoted by SEQ ID NO: 14) and 5'-AATTCGTACGTACA-3' (lower strand denoted by SEQ ID NO: 15). TRIPZ-snaBI ligation reaction (2 µl) was electroporated into 40 µl electrocompetent E. coli cells. Electroporation was performed with BioRad Gene Pulser set to the following parameters: 2500V, 200 Ohm and 25 pFa. Immediately after electroporation, 1 ml of LB medium was added to the treated bacteria, incubated for 1hour at 37° C. and plated on LB agarose plates, supplemented with X-Gal and IPTG for Blue/White Screening.

Next, the TRIPZ-snaBI plasmid was digested with snaBI, ligated with the 804 bp PCR product and electroporated into competent E. coli cells. Positive clones were detected by Blue/White screening. The orientation of the insert (sense or antisense) was determined by sequencing with sequencing primer located on TRIPZ nt 2920-2939: CGTATGTCGAGGTAGGCGTG (denoted by SEQ ID NO: 16).

SHC203-Plasmids

SHC203 (Sigma-Aldrich) is a lentiviral vector derived from the pLKO.5 vector with a puromycin resistance gene and a turboGFP reporter. The shRNA inserted as described below was expressed from a U6 promoter in this plasmid. Two shRNAs were inserted into the SHC203 vector: the shRNA non-silencing (denoted by SEQ ID NO: 3) and a modified "shRNA-1" which is based on the target-like sequence and its respective inverted repeat having the sequences denoted by SEQ ID NO: 5 and SEQ ID NO: 6, respectively (directed against the KAI1 as-lncRNA), separated by a loop having the 6 bases sequence CTCGAG. The modified shRNA-1 sequence was ordered as the two following oligomers from Sigma:

```
KAT1-shRNA-1 upper (for insertion into SHC203)
                          (denoted by SEQ ID NO: 18)
CCCGGACAACTCATGGGTACTCTCGTCTCGAGACGAGAGTACCCATGAGTT

GTTTTTTGT

KAI1-shRNA-1 lower (for insertion into SHC203)
                          (denoted by SEQ ID NO: 19)
AACAAAAAACAACTCATGGGTACTCTCGTCTCGAGACGAGAGTACCCATGA

GTTGTCCGG.
```

The flanking sequences (CCCGG, TTTTTGT, AACAAAAA and CCGG, respectively) are shown at both 5' and 3' ends of the upper and lower nucleic acid, respectively. SHC203-Plasmid expressing the modified shRNA-1 is termed herein "SHC203-shRNA-1" or "SHC-shRNA-1" interchangeably.

The two inverted repeats-containing oligonucleotides with an HpnI and KpnI digested overhangs were annealed and ligated into the HpnI and KpnI digested SHC203 vector. The ligation reaction was transformed into $CaCl_2$ competent E. coli cells. Plasmid prep was performed as described above. To verify the sequence of the insert, the SHC203-shRNA-1 plasmid was sent to sequencing with the following primers:

```
Forward primer
                          (SEQ ID NO: 22)
TTTCTTGGGTAGTTTGCAGTTTT Reverse primer
                          (SEQ ID NO: 23)
ACCGTAAGTTATGTAACGCGGA
```

Plasmid DNA Preparation

Frozen DH10B E. coli strain previously transformed with respective Plasmid DNA were plated on LB agar plates containing 100 µg/ml Ampicillin and incubated in 37° C. On the next day, 4 ml SB starter medium containing 100 µg/ml Ampicillin and 25 µg/ml Zeomycin (if needed) was inoculated with a single colony and incubated at 37° C. overnight. The starter culture was inoculated into 250 ml SB medium (with the respective antibiotics) and incubated at 37° C. while shaking until reaching an $OD_{600}$ of 0.6-0.8. Bacterial cells were collected by centrifugation at 5,000 rpm for 15 min at 4 C°. Plasmid DNA was prepared with NucleoBond® Midiprep/Maxiprep (Macherey-Nagel) according to the supplier's instructions.

Agarose Gel Electrophoresis of DNA and RNA

In order to analyze PCR products, Plasmid quality or RNA intactness, samples were loaded on a 0.75%-3.5% agarose gel, depending on the expected molecular weight. The running buffer contained 40 mM Tris-Acetate pH 7.5 and 2 mM EDTA. Typically, the electrophoresis was carried out at constant voltage of 100-120V for 30-60 min.

SHC203 and TRIPZ Lentiviral shRNA/shRNAmir Formation and Production

The SHC203 lentiviral vector (Sigma Aldrich) and the TRIPZ inducible lentiviral vector (Open Biosystem Inc.) infect both dividing and non-dividing cells. The Tet-On System in the TRIPZ lentiviral vector allows induction of shRNAmir (short hairpin flanked by micro RNA (mir) sequences in the presence of doxycycline. The SHC203 lentiviral vector expresses the shRNA constitutively. Both vectors are replication-defective lentiviruses of the second generation and were produced in HEK293T cells. Each vector (shRNA containing transfer vector) needed to be co-transfected with two second generation packaging plasmids, psPAX2 and pMD2.G, that encode for the viral helper proteins.

Virus producing HEK293T cells were seeded one day prior to transient transfection in a 100 mm tissue culture dishes until reaching ~90% confluency on the next day.

One hour prior to transfection, 60 mm dishes were coated with Poly-L-Lysine, incubated for 30 min and washed twice with Tissue Culture Water and DMEM containing 10% FBS. Meanwhile the following transfection mixes were prepared (Table 1 below):

TABLE 1

Transfection procedures using TRIPZ and SHC203 lentiviruses

| | Tube 1 | Tube 2 |
|---|---|---|
| TRIPZ lentivirus | 3 µg transfer TRIPZ Plasmid<br>2 µg psPAX2 Plasmid<br>1 µg pMD2.G Plasmid<br>up to 250 µl 150 mM NaCl$_2$ | 40 µl PEI<br>210 µl<br>150 mM NaCl$_2$ |
| SHC203 lentivirus | 4 µg transfer SHC203 Plasmid<br>2 µg psPAX2 Plasmid<br>1 µg pMD2.G Plasmid<br>up to 250 µl 150 mM NaCl$_2$ | 40 µl PEI<br>210 µl<br>150 mM NaCl$_2$ |

Tube 2 was added drop wise into tube 1 and mixed vigorously. The DNA Mix was incubated for 15-20 min at room temperature for complex formation.

HEK293T cells were detached with 5 ml DMEM from the 100 mm culture dish, added to the DNA complex, poured into the 60 mm culture dish and incubated for 24 hours at 37° C. with 5% CO$_2$. On the next day the medium was changed to 6 ml fresh DMEM with 10% FBS and incubated for 24 hours at 37° C. with 5% CO$_2$. Subsequently, the medium was supplemented with 25 mM of chilled HEPES (pH 7.18), harvested and passed through a 45 µm filter to remove cell debris.

Virus Infection

MDA-MB-231 or MDA-MB-435 cells were seeded in a 6-well plate one day prior to infection until reaching a ~40-50% confluency. Shortly before infection, fresh DMEM Medium supplemented with 10% FBS and 16 µg/ml Polybrene was added to the receiver cells. Each virus supernatant, specifically, TRIPZ and SHC203 was added drop wise to the well and diluted the polybrene concentration to 8 µg/ml. Cells were spin infected at 2250 rpm for 90 min at 32° C. and subsequently incubated at 36° C. and 5% C02. After six hours the infection medium was exchanged by fresh 10% FBS DMEM (supplemented with 2 µg/ml doxycycline when infected with TRIPZ). TRIPZ shRNAmir formation was maintained by daily doxycycline induction. Forty eight hours post infection, the selection with 0.1-1 µg/ml puromycin was introduced. Two to five days of selection were required before measuring gene expression.

RNA Extraction from Cell Culture

Cells were detached with Trypsin-EDTA from their culture dish, centrifuged for 1 min at 2000 rpm in a table biofuge (Heraeus). To extract total RNA, EZ-RNA Kit (Biological Industries, Israel) was used according to the manufacturer instructions. After RNase free DNase treatment (RQ1 DNase, Promega) total RNA was subjected to sodium periodate treatment.

Nuclear RNA was isolated by perforating the cells with 0.1% digitonin in Hank's Balanced Salt Solution (HBSS) and 1 mM PMSF. Following, cell ghosts were collected by a low speed spin. The pellet was further subjected to RNA extraction, with the EZ-RNA kit (Biological Industries, Israel).

Periodate Treatment

Total DNase-free RNA was subjected to 30 mM sodium periodate in 300 mM sodium acetate and incubated for 1 hour at room temperature. The beta elimination reaction of the RNA 3'-OH was stopped by adding 100 mM Dextrose for a 10 min incubation period. Afterwards RNA was precipitated in ethanol.

Reverse Transcription

Reverse Transcription was carried out using 200 U RevertAid™ Premium (Thermo Fisher) which is an RNase H minus M-MLM derived enzyme, at 50-60° C. (when using gene specific primer), or at 42° C. when using random hexamer or Oligo dT$_{(15)}$ primer. RT with 30 U AMV derived enzyme were carried out at 37° C. Usually, 1 µg of RNA was subjected to reverse transcription reaction in 20 µl. The RT reaction was then diluted to 100 µl with DEPC treated water. RT reaction (5 µl) were subjected to PCR amplification using Maxima Hotstart Taq-polymerase (Thermo Fisher). PCR conditions were as follows: 95° C. for 4 min for initial denaturation and activation of the hotstart enzyme, 25-40 cycles of 95° C. for 30 seconds, Tm −5° C. for 30 seconds for annealing and 72° C. for 30 sec/kb for elongation. A final extension step at 72° C. for 4 min was applied for most amplifications.

Actinomycin D Treatment

Actinomycin D was added to the reverse transcription reaction at a concentration of 50 ng/µl. For following PCR amplification Actinomycin D had to be diluted to 1.25 ng/µl in order to not inhibit the Taq-Polymerase activity.

RNA Pull Down with Magnetic Dynabeads®

Total RNA (2-60 µg) with 1-5 pmol Biotinylated-Oligo (dT)$_{25}$ were heated for 1 minute at 70° C. to open up secondary structures and snap chilled on ice. NaCl (1M) and EDTA (10 mM) were added to a final concentration of 200 mM and 0.2 mM, respectively. Annealing was allowed at room temperature under steady rotation for 30 minutes. Meanwhile, 2-3× molar excess of supermagnetic beads, which are covalently coupled to a monolayer of recombinant streptavidin, were prepared for RNA manipulations by washing with 0.1M NaOH and 0.05M NaCl. The RNA-biotinylated-oligomer complex was added to the magnetic beads and rotated at room temperature for 30-60 min. The very high binding affinity of the biotin-streptavidin interaction ($K_d=10^{-15}$) permits the specific isolation of the annealed polyA plus RNA by placing the tube on a magnet, while saving the polyA minus RNA containing supernatant. The magnetic beads bound polyA plus RNA was eluted in 1 mM Tris (pH 8) and 0.1 mM EDTA (pH 8) and used for downstream applications. Table 2 recites sequences of various primers used as described herein.

TABLE 2

Primer/Oligomer Sequences

| SEQ ID No. | Oligo Name | Sequence |
|---|---|---|
| 24 | KAI1 RealTime Forward | CGGCAACAGGACCCAGAGTG |
| 25 | KAI1 RealTime Reverse | CGGCACAAGCAGATGGACAGG |
| 26 | KAI1 qRT-PCR pair a Forward | CAGGATGCCTGGGACTACGT |

TABLE 2 -continued

Primer/Oligomer Sequences

| SEQ ID No. | Oligo Name | Sequence |
|---|---|---|
| 27 | KAI1 qRT-PCR pair a Reverse | GACCTCAGGGCGATTCATGA |
| 28 | KAI1 qRT-PCR pair b Forward | TCTGTGAGGAAGGGCTTCTG |
| 29 | KAI1 qRT-PCR pair b Reverse | GTACTTGGGGACCTTGCTGT |
| 30 | KAI1 qRT-PCR pair c Forward | GGAGAACCTGGGCATCATCC |
| 31 | KAI1 qRT-PCR pair c Reverse | TTGGGGACCTTGCTGTAGTC |
| 32 | KAI1 RT 2 | TCAGCGCTTGGCATAGAG |
| 33 | KAI1 RT 3 | GCACTGGTTGTTCTGGGCTA |
| 34 | KAI1 RT 5 | CAACGGTGTGTTGTGAGAGG |
| 35 | KAI1 Promoter 3 Forward | CCTGATAGAGGCCCCGACT |
| 36 | KAI1 Promoter 3 Reverse | ATTCCAGGGCGGGTGTAT |
| 37 | KAI1 RT2 Reverse compl. | CTCTATGCCAAGCGCTGA |
| 38 | KAI1 RT3 Reverse compl. | TAGCCCAGAACAACCAGTGC |
| 39 | KAI1 60 mer nc | CTCTGAGCCTTAAACTGCGCATTAG TAAAATAGGCGCAACGAGAGTACCC ATGAGTTGTG |
| 41 | HPRT-1 qRT-PCR Forward | GCCCTGGCGTCGTGATTA |
| 42 | HPRT-1 qRT-PCR Reverse | CCCTTTCCAAATCCTCAGCAT |
| 43 | TBP Forward | CACAGGAGCCAAGAGTGAAGAA |
| 44 | TBP Reverse | AAGAACTTAGCTGGAAAACCCAAC |
| 45 | GFPtpz qRT-PCR Forward | GTTCAGCGTGTCCGCGAGG |

Quantitative Real-Time PCR

All reactions were performed in 20 µl mixtures consisting of 2× Quanta perfect SYBR Green fast mix (Quanta Bioscience), 10 pmol of respective primers and 25-150 ng of cDNA. HPRT-1 or TBP mRNAs served as internal references for linear transcripts, while Amplification conditions were as follows (if not stated differently): Initial incubation at 50° C. for 2 min and 95° C. for 3 min, followed by 40 cycles of 95° C. for 10 seconds, 50-68° C. for 30 seconds and a final dissociation (2 cycles of 95° C. 15 sec and 60° C. 1 min) stage. Calibration curves were performed for every product and primer efficiency was determined, tolerating a range of 95%-105%. Ct values were monitored and analyzed by the 7300 fast Sequence Detection System Software (Applied Biosystems). All reactions were performed in triplicates.

DNA Extraction from Cell Culture

DNA from cell cultures (100 mm dish) was extracted using the Zymo DNA Extraction kit according to manufacturer instructions.

5'-RACE

To determine the transcription start of the poly-A minus lncRNA, 60 µg RNA was annealed to a 3'-biotinylated −60 mer and bound to streptavidin coupled magnetic beads. Following, the RNA was reverse transcribed with a transcript specific primer, RNase A treated and poly A tailed by Terminal transferase (Thermo Scientific) according to the suppliers' instructions. The polyA tailed cDNA was Ethanol precipitated and cleaned up through a NucleoSpin® Column (Macherey-Nagel). Second strand synthesis with RevertAid Premium (Thermo Scientific) was performed using an adapter with a poly-T tail to prime the generated poly-A tail of the cDNA. PCR was performed with the adapter (without the poly-T tail) and transcript specific primer that served as RT-primer. "Nested"-PCR was performed with the adapter and a transcript specific oligomer priming closer to the 5'-end of the cDNA transcript. PCR products were cloned into pGEM®-T Easy Vector and sent to sequencing.

SDS-PAGE and Western Blot

Samples Preparation

Cells were washed in Tris Saline (TS), detached from tissue dish on ice and harvested by quick spin down in tabletop centrifuge at 13,000 rpm. Then 200 µl 0.1% digitonin was added to suspend the cell pellet. After quick spin down, supernatant was transferred to a new tube. Cells were disrupted mechanically with a homogenizer and 200 µl of 0.1% digitonin was added to the cell ghosts. After a quick spin down, the supernatant was transferred to a new tube and the cell ghosts were lysed in 2% CHAPS. Samples were centrifuged at 11,000 rpm for 10 minutes. Protein concentration of the supernatant and the digitonin fraction were determined by Bradford assay. Denaturation of samples was obtained with SDS-loading buffer (40% Glycerol, 10% SDS, 10 mM EDTA, 5 mM EGTA, 100 mM Tris pH 6.8, 0.5M DTT). To eliminate genomic DNA, the samples were exposed to sonication with Microson™ cell disrupter (Misonix). Following, samples were heated to 95° C. for 5-10 minutes.

SDS-PAGE and Protein Transfer to Nitrocellulose Membrane 20-50 µg protein from each sample was loaded on a 10% SDS-Gel. The gel initially runs for 10 minutes at 100V, followed by 40-60 minutes at 120V. The proteins in the SDS-gel were then transferred to a nitrocellulose membrane in a semi-dry blot container. Blotting paper and nitrocellulose membrane were therefore placed in Transfer Buffer (with 20% Methanol), and together with the SDS-Gel assembled to a blotting sandwich. Transfer was carried out at room temperature under constant current of 100 mA for 60 minutes. Blotting efficiency was checked with Ponceau staining.

Imaging

The Nitrocellulose membrane was blocked for 60 minutes with Odyssey® Blocking Buffer PBS (Li-cor) at room temperature under constant shaking. After blocking, an overnight incubation with the primary antibody at 4° C. followed. The primary polyclonal antibody C-16 (Santa Cruz) raised in rabbits against human CD82 (KAI1) was diluted 1:200 in Odyssey® Blocking Buffer. On the next day, the membrane was washed three times with PBS-Tween before incubation with the DyLight 800 (KPL) secondary antibody (goat anti rabbit) for 60 minutes at room temperature, diluted 1:10,000 in Odyssey® Blocking Buffer. After three washes with PBS-tween, the membrane was exposed to infrared detection with the Odyssey® Infrared Imager (Li-cor).

Similarly, immuno-staining with endogenous control antibody FL-335 (rabbit anti human GAPDH; 1:1,000, Santa Cruz) was for two hours at room temperature followed by secondary antibody DyLight680 (KPL), washing and exposure as outlined above.

Cell Counting with Hemocytometer

Cells were detached from culture dish in Trypsin-EDTA. A clean coverslip is placed on an H-shaped hemocytometer and a sample of 10 ul of the cell suspension is loaded onto the V-shaped wells and gets soaked under the area of the coverslip by capillary action. The counting grid contains nine large squares, each of which is 1 mm$^2$ and a depth of 0.1 mm. To estimate the cell number of the cell suspension, at least 5 squares have to be counted. Cells touching the top and right ruling are counted "in", while cells touching the bottom or left ruling are counted "out". Once the total cell count has been obtained, the cell concentration can be calculated with following formula:

$$\text{Total cells/ml} = \text{Total cells counted} \times \frac{\text{dilution factor}}{\text{\# of Squares}} \times 10{,}000 \text{ cells/ml}$$

Cell Viability Assay

Resazurin (Alamar Blue) can replace oxygen as an electron acceptor in the oxidative phosphorylation via cytochrome oxidase. As a result, Resazurin gets reduced and exhibits a color change, as well as a shift in fluorescence, which can be colorimetrically and fluorimetrically quantified. 20 µg/ml of Resazurin dissolved in PBS is given onto cells. The incubation at 37° C. takes 60 min until the fluorescence intensity can be determined at λ excitation 544 nm/λ emission 590 nm. Fluorescence values of two or more time points have to be checked in order to validate linearity. Relative cell viability of sample can be calculated by comparison to control untreated cells. Sample cell number can be estimated by setting up a cell number calibration curve.

Cell Growth Assay

Cells were seeded at various concentrations in a 96-well plate in four respective triplicates. On day 0 the cells of the first triplicate series were exposed to Resazurin Cell Viability Assay. Cell Viability was determined 24, 48 and 72 hours later with the respective next series. Doubling time was calculated by comparing cell viability at day 1 to day 0, day 2 to day 1, etc.

Fibronectin Adhesion Assay

Cells grown in 10% FBS containing DMEM are deprived from serum 24 hours prior to the adhesion assay. Forty eight well plates are coated with 10 µg/cm$^2$ Fibronectin diluted in HANK's Balanced Salt Solution and incubated overnight at 4° C. On the next day fibronectin coated 48-well plate is washed three times with PBS and blocked with 10 mg/ml heated BSA in PBS for 30 min. Cells are then collected, washed twice in PBS and resuspended in RPMI 1640 medium. Then 50,000, 100,000 or 200,000 cells are seeded in fibronectin coated and uncoated wells, respectively, and incubated for 30 minutes at 37° C. After 30 minutes, unattached cells were washed away. On the next day, cell viability of cells is determined by Resazurin Cell Viability Assay and percent of adherent cells is calculated relative to control wells.

Wound Healing Assay

Monolayer cells were grown to 100% confluency and deprived from serum 24 hours prior to the assay. With a plastic pipette tip a scratch was inflicted to the monolayer. Cells were carefully washed with Tris saline (TS) and serum free RPMI 1640 medium was added. Random fields of the scratch wound were marked and photographed with a light microscope camera at time 0 and after 24 hours incubation at 37° C. with 5% $CO_2$.

Migration Assay

To study cell migration, ThinCert™ (Greiner Bio-One) cell culture inserts were placed in a multi well cell culture plate. The insert contains a polyethylene terephthalate (PET) membrane at the bottom with a pore size of 8 µm that separates the upper from the lower compartment. Then 100,000 serum-starved cells are seeded at the top of the insert in 200 µl serum free media, while the lower compartment contains 10% FBS DMEM media as a chemo-attractant that may induce active migration of the seeded cells through the PET membrane. Adherent cells that migrate through the pores remain attached to the under-side of the PET-membrane. After 24 hours, the medium in the inserts and lower compartment is removed, the inserts washed with TS and incubated with Trypsin-EDTA for 10 minutes at 37° C. to detach the migrated cells from the under-side of the insert. The migrated cells are seeded in 48-well plate. To estimate the percentage of migrated cells, a Resazurin Cell Viability Assay is performed and compared to the mock control cells.

Invasion Assay

The ability of cells to invade through extracellular matrix can be studied in an invasion assay. Therefore, the same method of the ThinCert™ Migration assay was applied with the only difference being that the ThinCert™ inserts had to be coated with basement membrane matrix (Matrigel, Sigma). For coating, Matrigel had to be thawed on ice and diluted in serum free media to 1 µg/µl and pipetted to the center of the PET-membrane. The coated membrane was incubated at 37° C. for 4 hours and air dried under sterile conditions.

Example 1

Screening for Promoter-Spanning lncRNA of Metastasis/Tumor Suppressor Genes in Triple-Negative Breast Cancer The human genome transcribes thousands of lncRNA genes producing more than 27000 transcripts. The great majority of these lncRNAs are still unexplored and might be of major significance to many diseases and to human biology in general.

In order to try identifying new lncRNA/(s) which regulate metastasis and or tumor suppressor genes in breast cancer, the inventors screened for promoter-spanning lncRNAs in metastasis and/or tumor suppressor genes in which reduced transcription rather than mutation is the basis for the loss of their gene expression. To this end, the extent of mRNA expression in ten metastasis-/tumor-suppressor genes (devoid of known mutations in breast carcinoma) was analyzed by semi-quantitative RT-PCR in three different Basal B TNBC cell lines, namely MDA-MB 231, Hs-578T and SUM-149PT. This was performed in order to detect a potential down regulation of the mRNA transcript.

Upon analysis of the above Basal B TNBC cell lines as indicated above, gene expression of the genes FKBP4, KIF1A and OGDHL seemed to be high in all three cell lines and therefore these genes were excluded from screening for promoter spanning lncRNA. The high transcript levels is likely to indicate a lack of negative transcription regulation in TNBC cell lines and hence, these three genes do not seem to have a promoter spanning transcript that impedes their gene expression. Contrary, the expression of Cst6, MAL, VGF, RARbeta, Maspin, SYK and KAI1 varied, depending on the cell line examined. These differences in gene expression might indicate a cell line specific transcriptional regulation.

In order to identify lncRNA one should purify total cellular RNA/nuclear RNA, and subject it to site-specific RT-PCR. To prevent PCR amplification of genomic DNA, the breast cancer cell line extracted RNA was exhaustively treated with DNase. Also, in order to prevent the endogenous RNAs from serving as primers in the RT reaction, the RNA samples were treated with sodium periodate which blocked free 3' RNA ends from serving as endogenous primers in the RT reaction, as described above. Then, the directionality of these RT products has been determined by exogenously added primers (in the case of the KAI1 as-lncRNA primers having sequences denoted by SEQ ID NO: 36 and 38) in antisense or sense orientation, respectively. The reverse transcription was performed at elevated temperatures (50-60° C.) to prevent false priming. Moreover, the RT reactions were done in the presence of Actinomycin D to prevent the synthesis of the second DNA strand, which may falsely indicate the presence of antisense RNA. Since Actinomycin D is also a DNA-Polymerase inhibitor, its concentration was diluted to an insignificant amount prior to the PCR reaction step. Noteworthy, out of all seven tested genes only one, KAI1, had an antisense lncRNA spanning its promoter in both MDA-MB-231 and HEK293T as observed in FIG. 1.

In order to rule out the possibility that for the KAI1 as-lncRNA a reverse transcriptase template switching ("RT jump") has occurred thereby generating a false positive transcript, total RNA was reverse transcribed with two different reverse transcriptase (RTase) enzymes: a recombinant M-MLV RTase with a reduced RNase H activity (which has been used as outlined above) and an AMV RTase (with RNase H activity).

As shown in FIGS. 2A, 2B, 2C, the putative KAI1 as-lncRNA could be detected in RNA reverse transcribed with both RT-enzymes, M-MLV and AMV. Since both RT-enzymes reverse transcribed the putative KAI1 as-lncRNA, the level of certainty that the product is not based on a template switching event (DNA to RNA or RNA to RNA) increased.

Example 2

Structural Characterization of the KAI1 as-lncRNA

As the KAI1 promoter spanning as-lncRNA proved itself as a bona fide long noncoding RNA, a further study concentrated on its physical and functional characterization. In order to determine the 3' end of this lncRNA transcript, RT-PCR "walks" on the KAI1 as-lncRNA transcript towards its 3' end were performed, as graphically presented in FIG. 3.

The primer RT 5 (having the nucleic acid sequence shown in Table 2 above and denoted by SEQ ID NO: 34 anneals −1180 bp upstream of the KAI1 mRNA transcription start site (TSS), specifically, the major TSS, and is the furthest RT primer 5' of the TSS with which an antisense transcript was detected. The amplified 705 bp product of the RT-PCR (with the primer pair RT5 and Promoter-3-R, denoted by SEQ ID NO: 34 and SEQ ID NO: 36, respectively) is shown in FIG. 4.

The 5' end of the KAI1 as-lncRNA was then determined by performing a 5'-RACE reaction. Here, a specific oligomer SEQ ID NO: 32 primed the reverse transcription of the KAI1 as-lncRNA. Afterwards, the generated cDNA was tailed with polyT by a terminal transferase, which enabled the PCR primer with a poly-A leader sequence to anneal thereby allowing the transcript to be amplified.

Next, the products of a Nested-PCR have been cloned and sequenced. The sequencing revealed that the 5'-end of the transcript is located at position −386 of the KAI1 mRNA TSS, and in antisense polarity. Interestingly, the detected 5' end, as well as its flanking sequence are identical to the 5' end of a 792 bp long RNA transcript (UCSC Accession wgEncodeEH000148) denoted herein by SEQ ID NO: 46), found by sequencing of the GM12878 whole cell PolyA minus RNA fraction (contig_343318). A product downstream of the 3'-end of the submitted 792 bp transcript was not detected by RT-PCR, or by priming the transcript with oligo dT (FIG. 4), thus suggesting absence of a polyA tail.

Without wishing to be bound by theory, the RNA transcript UCSC Accession wgEncodeEH000148 and the KAI1 as-lncRNA transcript which was identified herein are the same.

It has been reported that only 17.8% of the human lncRNAs are polyadenylated. In order to test whether the antisense transcript of the KAI1 (spanning the promoter and enhancer regions identified herein) is polyadenylated or not, the following experiment was done. Polyadenylated MDA-MB-231 RNA was pulled down with Oligo d(T)$_{25}$-biotinylated Dynabeads® and RT-PCR was performed on the PolyA plus as well as on the flow through (PolyA minus) fraction. The KAI1 as-lncRNA transcript could only be detected in the PolyA minus flow through fraction. This implies that the transcript is not polyadenylated (FIG. 5A).

Example 3

Subcellular Localization of KAI1 as-lncRNA

Many reports of the subcellular localization of lncRNAs can be found. For example, some lncRNAs are almost exclusively located in the nucleus while in many other studied lncRNAs are found predominantly in the cytoplasm. In order to estimate the subcellular distribution of the KAI1 as-lncRNA, a semi-quantitative analysis of the RT-PCR product has been performed. Accordingly, 2 µg of nuclear RNA and 2 µg of total RNA have been reverse transcribed and amplified by PCR. The signal in the total RNA sample was much weaker than in the nuclear sample, suggesting an enriched KAI1 as-lncRNA fraction in the nucleus, as shown in FIG. 5B.

Example 4

Human KAI1 as-lncRNA: Transcript Sequence Homology with Other Species

An extensive search of homolog transcripts in other species turned out to be fruitful. In the transcriptome shotgun sequencing database, three mammalian transcripts from *Equus asinus, Equus przewalskii* and *Bubalus bubalis* have shown high homology to the KAI1 as-lncRNA transcript (initially detected in human TNBC cell lines), as described in FIG. 6. When superimposing these top 3 homologous transcripts with the KAI1 as-lncRNA, a 78 bp long sequence (having the consensus sequence denoted by SEQ ID NO: 17, the 3' to 5' sequence thereof as shown in the figure is denoted by SEQ ID NO. 49, is shown in the figure), which is mutual to all four transcripts, can be identified. Its complementary sense sequence has been reported to be a regulatory region (enhancer) of the KAI1 gene, and contains binding motifs for three transcription proteins, AP1, AP2 and p53 (Marreiros et al., 2003).

Example 5

The KAI1 Bi-Directional Promoter

As outlined above, the 5' end of the KAI1 as-lncRNA has been identified by 5' RACE and is located in proximity to the canonical KAI1 mRNA TSS. Since the transcript also spans the enhancer region of the KAI1 gene, and might be involved in transcription regulation of the KAI1 mRNA, it was examined whether a coordinately expressed gene pair transcripts, composed of the KAI1 mRNA and KAI1 as-lncRNA are present. In other words, it was examined whether this TATA-less promoter initiates transcription in both directions and directs transcription of the KAI1 gene in the sense orientation, and KAI1 as-lncRNA in the opposite antisense orientation.

Accordingly, the 1198 bp promoter and enhancer region of the KAI1 gene were cloned in sense and antisense orientation (having nucleic acid sequences denoted by SEQ ID NO: 20 and SEQ ID NO: 21, respectively) into a promoter-less pGL3-luciferase vector, as schematically shown in FIG. 7A and in FIG. 7B and as described above. The model cells HEK293T were used because they are excellent DNA recipients for co-transfection by pGL3-luc-1198 bp promoter-sense or -antisense orientation and pTK-*Renilla* DNA as an internal normalizing control. Importantly, as demonstrated in FIG. 7C the promoter in the antisense orientation initiated luciferase transcription, albeit at a ~4.7 fold weaker level than the promoter in the sense orientation (i.e. orientation of the KAI1 mRNA). Nevertheless, these results indicated that the KAI1 promoter is active in both orientations, manifesting a bidirectional regulation of the KAI1 mRNA and KAI1 as-lncRNA. The luciferase assay was also performed in MDA-MB-231 and MCF-7 cells, which showed a poorer transfection rate, but still indicated a bidirectional activity of the KAI1 promoter, as demonstrated in FIG. 7D and in FIG. 7E. In MDA-MB-231 and MCF-7 cells the promoter activity in sense orientation is only about twice as high as in the antisense orientation.

Example 6

The KAI1 as-lncRNA Expression in Breast Cancer and Melanoma Cell Lines

It has been reported that lncRNAs play functional roles in transcriptional regulation. In addition, dis-regulated expression of lncRNA can also serve as marker in disease progression of cancer patients. In view of the above, the expression level of the KAI1 as-lncRNA was tested as described above in two basal B TNBC cell lines (MDA-MB-231 and SUM159PT), in the luminal breast cancer cell line MCF-7 and in the melanoma MDA-MB-435 cell line. The relative KAI1 as-lncRNA expression vs. KAI1 mRNA expression was compared in order to evaluate a possible correlation to the putative bi-directional promoter expression. As demonstrated in FIG. 7, while the KAI1 as-lncRNA expression in MCF-7 and SUM159PT is barely detectable via qRT-PCR, the transcript was more abundant in MDA-MB-231 and MDA-MB-435 cells. Next, the KAI1 mRNA Expression level was determined in the above four cell lines, while HPRT-1 mRNA served as an endogenous control. As shown in FIG. 8, a relatively high KAI1 mRNA Expression level was detected in MCF-7 and SUM159PT cells, whereas in MDA-MB-231 cells the KAI1 mRNA expression was found to be very low, and in MDA-MB-435 the expression was barely detectable.

An inverse correlation between KAI1 expression and the metastatic potential of breast cancer cells was previously described, suggesting that KAI1 is a metastasis suppressor gene (Yang et al., 2000). The capability of a cell to be metastatic can be measured based on its invasiveness. Therefore, the invasiveness of the four indicated cell lines was studied using a classical invasion assay, as detailed above.

As demonstrated in FIG. 10, MDA-MB-435 appears to take the lead in the invasiveness, followed by MDA-MB-231 and SUM149PT. MCF-7 cells were not invasive enough to be observed and fell under the detection barrier. In these four cell lines, a coordinated expression of the KAI1 as-lncRNA and the KAI1 mRNA might dictate the invasiveness of these cells. Hence, without wishing to be bound by theory, it is suggested that a high KAI1 as-lncRNA expression interrelates with a low KAI1 mRNA level, leading to high invasiveness.

Example 7

Knockdown of KAI1 as-lncRNA

Realizing the inverse relationship between the KAI1 as-lncRNA expression and the KAI1 mRNA level as demonstrated above, we tested whether manipulation of the KAI1 as-lncRNA level would affect the KAI1 mRNA expression.

In order to test if the KAI1 as-lncRNA regulates the transcription or stability of its associated KAI1 mRNA, a fragment encoding shRNA directed against the KAI1 as-lncRNA was cloned into the lentiviral plasmid SHC203 (Sigma), as detailed above. Cell transduction with the SHC203-shRNA-1 construct was performed by virus infection as described above. A scrambled shRNA served as a "non-silencing" negative control, while an shRNA-less plasmid has been an empty-vector negative control.

Importantly, while designing to knockdown the primarily nuclear KAI1 as-lncRNA via RNA interference, the inventors considered that RNAi occurs not only in the cytoplasm, but also in the nucleus, based on previous results in collaboration with another search group (Avivi S. et al., 2017). First, in order to ensure that the shRNA directed against the KAI1 as-lncRNA indeed leads to knockdown of the latter transcript, MDA-MB-231, MDA-MB-435 and MCF-7 cells were infected with the lentiviral virus encoding the shRNA directed against the KAI1 as-lncRNA transcript, as described above. This was followed by total RNA extraction and qRT-PCR of the KAI1 as-lncRNA. Since the primer pairs which amplifies the KAI1 as-lncRNA could also amplify genomic DNA, an exhaustive DNA digestion of the RNA preparations had to precede the qRT-PCR. Briefly, by adding a "minus RT" control, contaminations of genomic DNA could be detected. The "minus RT" control for all the samples did not lead to any products, which assured the total digestion-elimination of genomic cellular DNA (data not shown).

As shown in FIG. 11A, in MDA-MB-231 cells a ~55% knockdown of the KAI1 as-lncRNA was achieved with the SHC-shRNA-1 directed to the KAI1 as-lncRNA, while infection with the control non-silencing vector did not result in KAI1 as-lncRNA knockdown. The empty vector control value was normalized to 100%. In addition, in MDA-MB-435 cells the KAI1 as-lncRNA expression was reduced by ~53% (FIG. 11B), and in MCF-7 cells by even ~63% (FIG. 11C).

After this partial knockdown of KAI1 as-lncRNA in MDA-MB-231, MDA-MB-435 and MCF-7 cells was established, the effect of knockdown of KAI1 as-lncRNA on the expression level of KAI1 mRNA was examined, as shown in FIG. 12.

Consequently, the KAI1 mRNA expression was quantified in MDA-MB-231 (FIG. 11A), MDA-MB-435 (FIG. 12C) and MCF-7 (FIG. 12B) cells after infection with the lentivirus encoding the shRNA-1 (SHC-shRNA-1) directed against the KAI1 as-lncRNA or the shRNA-non-silencing control.

As clearly shown in FIG. 12, after knockdown of the KAI1 as-lncRNA, the KAI1 mRNA level increased up to ~4 fold in MDA-MB-231 and MDA-MB-435 cells, while only 1.5 fold in MCF-7 cells. HPRT-1 served as endogenous control, which was not affected by the RNAi mediated knockdown of the as-lncRNA.

The non-silencing shRNA (ns-shRNA) controls did not have any influence on either the KAI1 as-lncRNA or its mRNA expression level. Yet, in order to be sure that knockdown of the KAI1 as-lncRNA was not due to an artifact of the lentiviral virus SHC203, a similar test using another lentiviral virus was performed. To this end, the pTRIPZ dox-induced lentiviral vector (Open Biosystems Inc.) was used for cloning of the shRNA directed against the KAI1 as-lncRNA, as described above, as well as for cloning the shRNA-scrambled "non-silencing". It should be pointed out (as described above) that whereas TRIPZ had a 19-nucleotide hairpin loop, the SHC203 vector harbored only 6 bases hairpin loop; yet, the processed active siRNA was obviously the same.

As demonstrated in FIG. 13, while in MDA-MB-435 cells up to ~3.7 fold increase (FIG. 13A) was observed, in MDA-MB-231 cells the KAI1 as-lncRNA knockdown led to only ~2.5 fold increase of the KAI1 mRNA (FIG. 13B). Importantly, in both cell lines the KAI1 mRNA expression level increased following KAI1 as-lncRNA knockdown. In addition, two other KAI1 as-lncRNA targeted shRNA constructs were cloned into the TRIPZ lentiviral vector and infected the MDA-MB-435 cells (referred to in FIG. 13A as "shBroad-1" and "shBroad-2" and having nucleic acid sequences denoted by SEQ ID NO:47 and SEQ ID NO:48, respectively). This led to only 1.5-1.75 fold elevation in KAI1 mRNA (FIG. 13A). Consequently, further experiments were performed only with shRNA-1 comprised in the TRIPZ or the SHC203 vectors.

Example 8

The Effect of KAI1 as-lncRNA Knockdown on KAI1 Transcript Variants

KAI1 is affiliated with 14 transcripts (also termed "splice variants") in the genome databases. The principle transcript consists of 10 Exons and is translated into a 267 amino acid long protein, which is known to be the functional transmembrane protein KAI1 (having for example the amino acid sequence denoted by SEQ ID NO:40). The primers pair initiating the amplification of the KAI1 cDNA had been designed to amplify the major (principle) transcript. However, little is known about the 13 other splice variants, which may have no metastatic suppressive or even oncogenic attributes. Consequently, it was checked if knockdown of the KAI1 as-lncRNA also leads to an increase of all transcripts or only the major transcript which is translatable into the metastasis suppressing protein KAI1.

The KAI1 mRNA level was thus evaluated by three different primer pairs, enabling the combined amplification of various isoforms. Primer pair "a" designed on exon 7 and 8 of the canonical KAI1 mRNA and amplifies transcripts 01, 02, 07, 12 and 14. The nucleic acid sequence of the forward and reverse primers of primer pair "a" is denoted by SEQ ID NO: 26 and SEQ ID NO: 27 respectively. Primers pair "b" (having nucleic acid sequences denoted by SEQ ID NO: 28 and SEQ ID NO: 29 for forward and reverse, respectively) amplifies transcripts number 01, 07 and 14, whereas primers pair "c" (having nucleic acid sequences denoted by SEQ ID NO: 30 and SEQ ID NO: 31 for forward and reverse, respectively) amplifies only the principle transcript 01.

FIG. 14 shows an increase of expression in all combinations of KAI1 transcripts calculated by qRT-PCR after KAI1 as-lncRNA knockdown in MDA-MB-231 cells. However, the strongest change with up to ~6 fold higher KAI1 mRNA expression could be detected with primers pair "c".

This indicates a specifically higher expression of the major KAI1 mRNA transcript after KAI1 as-lncRNA knockdown.

An additional fifteenth splice variant, lacking exon 9 of the canonical transcript which is expressed in metastatic tissue of gastric cancer patients with poor prognosis has been reported (Lee et al., 2003). Exon 9 encodes for amino acids which are part of the second extracellular loop of the transmembrane protein. Apparently, this splice variant leads to altered cell motility, adhesion and tumor growth compared to the major transcript. It is important to mention that Lee et al., consider this exon to be exon number 7, however, according to the officially recognized nomenclature, the missing exon is termed herein "exon 9".

In an effort to demonstrate the existence of this splice variant "exon 9", KAI1 cDNA was amplified with primers located on Exon 8 and 10, which leads to either the full length major product or the 84 base pair shorter splice variant. By exhaustive PCR amplification the spliced variant was detected in MDA-MB-231 cells that were infected with shRNA encoding SHC203 lentivirus (data not shown). Apparently, no significant change of the spliced "Exon 9" transcript expression due to KAI1 as-lncRNA knock down was ascertainable (data not shown).

Example 9

The Influence of KAI1 as-lncRNA Knockdown on the KAI1 Protein

Next, it was examined whether the increased KAI1 mRNA expression in MDA-MB-231 cells following knockdown of the KAI1 as-lncRNA also results in an elevated protein level. As demonstrated in FIG. 15A, indeed knockdown of the KAI1 as-lncRNA led on the average to 2.3 fold higher KAI1 protein level compared to the control wild type MDA-MB-231 cells, or those infected with non-silencing shRNA expressing SHC virus. Quantitation of these results is shown in FIG. 15B.

Example 10

The Effect of Ectopic Expression of KAI1/CD82 Gene on MDA-MB-231 Cell Proliferation In order to study the Effect of Ectopic Expression of KAI1/CD82 gene on MDA-MB-231 cell proliferation it was first checked whether MDA-MB-231 cells cultured in the Inventor's laboratory behave in the same way as those described in the literature with respect to cell proliferation.

To this end the KAI1 open reading frame cDNA was amplified and cloned into the doxycycline-inducible lentiviral expression vector TRIPZ in sense or antisense orientation, as outlined above. By qRT-PCR the inducible expression of both KAI1 transcripts, in sense (KAI1$^{OE}$) and antisense (KAI1$^{OE-AS}$) orientation was shown, as demonstrated in FIG. 16A and FIG. 16B. The reverse transcription was primed with an oligo dT primer and the amplifying PCR primers were mutual (the same) for exogenous sense, antisense and endogenous KAI1 mRNA transcripts. The minus RT control (FIG. 16C) confirmed the amplification of RNA transcripts, only. Both exogenous transcripts were expressed in MDA-MB-231 cells, the sense orientated KAI1 ORF RNA about 3.9 fold, the antisense orientated ORF RNA even 6.8 fold more than the endogenous wild type KAI1 mRNA, leading to either-2.2 fold more KAI1 protein or the decrease of the endogenously synthesized KAI1 protein, respectively (FIG. 16D and FIG. 16E).

It is known that a high proliferation rate due to limitless replicative potential is one of the six hallmark of cancer cells. However, Malik et al., observed no difference in cell growth kinetics when comparing KAI1 knockdown, overexpression and wild type MDA-MB-231 cells (Malik et al., 2009). Therefore TRIPZ (comprising the sense or antisense ORF encoding fragment infected MDA-MB-231 cells were seeded in 48 wells and their doubling time was measured every 24 hours, for 4 days. The average doubling time of the four samples was about 20-26 hours. In accordance with Malik et al. results, a significant difference in the doubling time of KAI1 overexpressing cells (ORF S) compared to the overexpression of the antisense orientated ORF control (ORF AS) was not detected, when calculating the average growth rate (see FIG. 17).

Example 11

The Phenotype of KAI1 as-lncRNA Knockdown Cells: Wound Healing

As indicated above, KAI1 has been reported to play a crucial role in suppressing invasiveness and metastasis (Feng et al., 2015). This phenotype was further studied, in order to test whether knockdown of KAI1 as-lncRNA and consequently the higher KAI1 mRNA and protein expression, would rescue the metastasis suppressive character of KAI1.

The mechanism of tumor dissemination by both metastasis and invasion is based on the cell motility machinery. It has been mentioned above that elevating KAI1 expression leads to retardation of cell mobility of cancer cells in vitro. Therefore, a wound healing assay was performed on MDA-MB-231 cells after being infected with SHC203 based viruses expressing shRNA-1 targeting the KAI1 as-lncRNA (SHC-shRNA-1). The wound healing in the presence thereof was compared to wound healing in the presence of an empty vector- or an shRNA-non-silencing control cells. As demonstrated in FIG. 18, after 24 hours the wounds of sh-empty and shRNA-non-silencing expressing cells healed, while the wound healing of shRNA-1 expressing cells was noticeably retarded.

The healing process was also compared to untreated cells which assisted in exclusion of a scenario involving migration-retardation inflicted by lentiviral infection per se. While the wound is almost completely healed within 24 h in untreated MDA-MB-231 cells, the scratch in KAI1 as-lncRNA knockdown cells is still apparent.

Example 12

The Phenotype of KAI1 as-lncRNA Knockdown Cells: Cell Migration

According to the scratch wound healing assay performed as described above, knockdown of the KAI1 as-lncRNA has led to a retarded migration, at least in the tested MDA-MB-231 cells. Similar results were obtained, when performing a trans-well migration assay. For that purpose, 50,000 cells were seeded in each 8 µm porous trans-well (Boyden chamber), which have not been coated previously. After 24 hours the cells that migrated towards the chemo-attractant (10% FBS) were exposed to a resazurin-based cell viability assay, to determine their migration rate. In line with the scratch wound healing assay, less KAI1 as-lncRNA knockdown cells SHC-shRNA-1 migrated (~9.5%) compared to the control cells infected with either an empty vector (sh-empty) or a scrambled shRNA (sh-non-silencing) of which 28% and 25% of the cells migrated through the trans-well, respectively, as demonstrated in FIG. 19.

Both the wound healing assay and the migration assay through a trans-well showed that increased KAI1 mRNA and thereby increased protein expression, due to KAI1 as-lncRNA knockdown, resulted in migration-retardation of MDA-MB-231 cells in vitro.

The migration results were supported by control experiments in which increased KAI1 mRNA expression by transducing MDA-MB-231 cells with the KAI1 ORF overexpression virus TRIPZ-KAI1$^{OE}$ led to ~60% less migrating cells when compared to the non-induced KAI1 mRNA overexpression (FIG. 20). When inducing the overexpression of the KAI1 mRNA in antisense direction, the migration rate is significantly higher than in non-induced cells. Without wishing to be bound by theory, this may be due to inhibiting expression of the endogenous KAI1 mRNA.

Example 13

The Phenotype of KAI1 as-lncRNA Knockdown Cells: Cell Adhesion

It is known that carcinoma cells that become metastatic have to disconnect from the original cell mass. Thus, loss of cell-cell adhesion can be the initial step of cell dissemination. It has been reported that KAI1 mediates cell-cell adhesion by altering the stability and density of alpha-integrins (Feng et al., 2015). In order to test the adhesion of MDA-MB-231 cells after KAI1 as-lncRNA knockdown, a fibronectin adhesion assay was performed.

Figure 21:
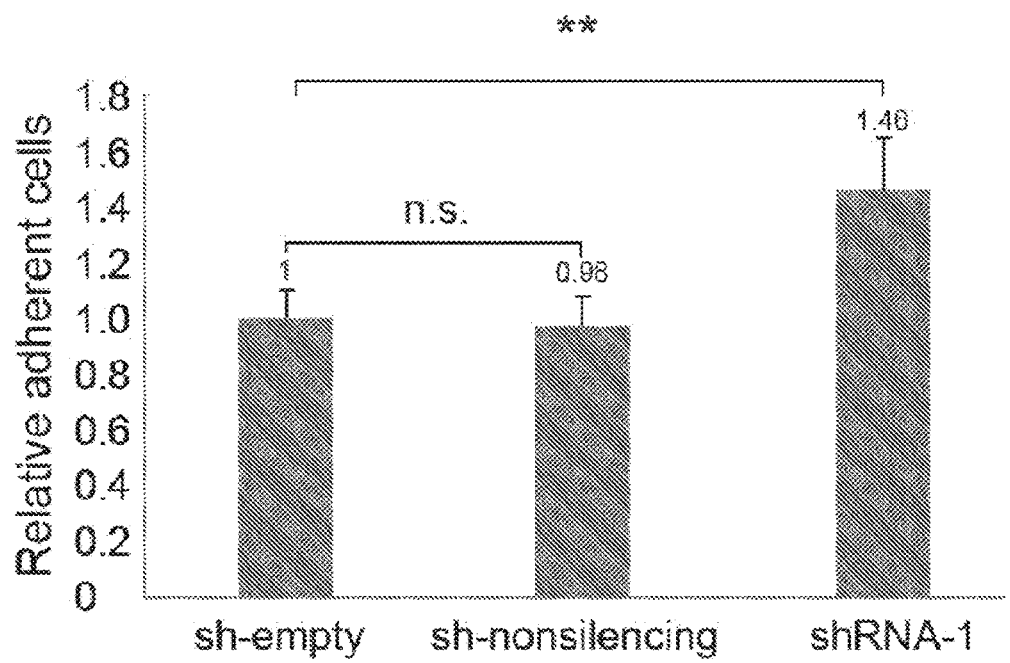

Briefly, ~50,000 cells were seeded on fibronectin coated 48-wells and incubated for 30 min at 37° C. The unattached cells were removed, and the relative amount of attached cells was detected by a resazurin cell viability assay and compared to the mock cell calibration. The results, which are illustrated in FIG. 21, indicate an around 46% stronger adhesion to fibronectin coated culture dishes by cells infected with shRNA targeting the KAI1 as-lncRNA (SHC-shRNA-1) as compared to the control infections (the sh-empty control is set to 100%).

When comparing the doxycycline induced KAI1$^{OE}$ cells to non-induced KAI1$^{OE}$ cells, induced KAI1$^{OE}$ cells show a ~62% stronger fibronectin adhesion (FIG. 22). The KAI1$^{OE-AS}$ induced control cells however, are ~45% less adherent to fibronectin coated culture dishes than the non-induced equivalent.

Example 14

The Phenotype of KAI1 as-lncRNA Knockdown Cells: Cell Invasion

It has been reported that KAI1 acts as a metastatic suppressor that decreases invasion. Breast cancer cells that disconnect from the primary tumor cell mass have to be able to degrade extracellular matrix components in order to invade normal surrounding tissue. To test the invasiveness of MDA-MB-231 after KAI1 as-lncRNA knockdown, 50,000 cells each were seeded in a 8 μm porous trans-well (Boyden chamber), which has previously been coated with Matrigel (Sigma). The Matrigel coating material is derived from the Engelbreth-Holm-Swarm murine tumor, being rich in laminin-111, type IV collagen, enactin and proteoglycan. After 24 hours the cells that invaded through the Matrigel towards the chemo-attractant (10% FBS) were exposed to a resazurin-based cell viability assay to determine their invasiveness.

As shown in FIG. 23, knockdown of the KAI1 as-lncRNA led to >50% less invading cells compared to the empty vector and non-silencing controls. The observed effect of KAI1 as-lncRNA knockdown on the invasiveness of MDA-MB-231 cells was confirmed by subjecting $KAI^{OE}$- or $KAI1^{OE-AS}$-expressing cells to the same invasion assay (FIG. 24).

Induction of the KAI1 mRNA expressing vector in MDA-MB-231 led to a ~62% reduced invasion rate in comparison to the non-induced cells. In contrast, induced KAI1 mRNA expression in antisense direction created a highly invasive phenotype (as outlined above for the migration assay), which is likely to reflect consequences of KAI1 mRNA degradation/inhibition.

Example 15

Correlating the Expression Level of KAI1 as-lncRNA to KAI1 mRNA Expression in Samples Obtained from Breast Cancer Patients Having Local Vs. Metastatic Disease As outlined above the inventors have found in breast cancer cell lines an inverse correlation between the expression level of KAI1 as-lncRNA to that of KAI1 mRNA, and consequently the degree of metastasis suppression. Furthermore, decrease of KAI1 as-lncRNA level was associated in vitro in cultured cells with increased cell adhesion, decreased cell migration, and reduced cell invasion. Currently, the inventors test whether such relationships also hold in vivo in tissues obtained from breast cancer patients. Snap-frozen primary breast tumor specimens, snap-frozen metastatic breast carcinoma samples, and Formalin-Fixed, Paraffin-Embedded (FFPE) tissue samples (as well as control normal breast tissues from reduction mammoplasties) were made available to the inventors by several hospitals in Israel. Similarly, to what has been described in Experimental Procedures and Example 6, following RNA extraction qRT-PCR is being used to determine the relative levels of KAI1 mRNA and KAI1 as-lncRNA in samples derived from normal breast organoid, primary breast carcinoma and metastatic breast carcinoma. The obtained data are correlated with the degree of disease invasiveness.

Example 16

Liposome Encapsulated siRNA Mediated KAI1 as-lncRNA Knockdown: Analysis of Cells Phenotype As outlined above in order to reduce the cellular amount of KAI1 as-lncRNA the inventors resorted to prolonged RNA silencing via shRNA expressing lentiviruses. Although the level of KAI1 as-lncRNA was reduced only by 50-60% (FIG. 12), this resulted in elevated KAI1 mRNA leading to reduced cell migration, and cell invasion, as well as increased cell adhesion (FIGS. 19, 23, and 21, respectively). Currently, the inventors seek to examine with respect to KAI1 as-lncRNA two additional modes of RNA silencing: a transient siRNA encapsulated lipid-based nanoparticles, and a prolonged one, employing the rAAV-shRNA-1 replication defective episomal virus (see below). With regard to the former a 21 bp long double stranded siRNA based upon SEQ ID NOs. 5 and 6, is employed in a way that the guide strand terminates with a 3' protruding UU end; occupying 19 of the 21 nucleotides long SEQ ID NO. 6. The synthetic siRNA is encapsulated into an ionized lipid nanoparticles grafted with the hyaluronan (HA), as outlined in Cohen Z. R. et al., 2015. The naturally occurring glycosaminoglycan HA binds specifically to the CD44 receptor which is highly expressed in triple negative breast cancer cell lines, thus enabling 100% infection in cultured cells, without the use of a dominant selection (such as puromycin-resistance in the case of lentiviruses). Similarly, the non-silencing siRNA negative control is prepared and following trapping into the said nanoparticles, is transfected to MDA-MB-231 cells alongside the KAI1 as-lncRNA targeting siRNA-lipid mixture.

In analogy with the former experiment, the levels of KAI1 mRNA and KAI1 as-lncRNA are determined by qRT-PCR at zero time and 72 hours thereafter in the control and targeted samples. The cells phenotype as demonstrated in FIGS. 19, 21 and 23 is determined in cases a significant gene specific reduction in KAI1 as-lncRNA, accompanied by parallel gene specific increase of KAI1 mRNA is observed.

Example 17 rAAV-shRNA Mediated Knockdown of KAI1 as-lncRNA: Analysis of Cells Phenotype In Vitro In this experiment the inventors are seeking through the usage of an episomal viral vector to effectively silence over a prolonged time frame, the expression of KAI1 as-lncRNA in cancer cells, and thereby suppress metastasis, and in several human cancers perhaps also the primary tumors. For this purpose a recombinant, replication defective Adeno Associated Virus (AAV) is used. This replicon encodes a GFP reporter and expresses shRNAs (Empty, NS, and KAI1 shRNA-1) from its polII H1 promoter. In order to generate a virus it is co-transfected into HEK293T cells, with pRep/Cap plasmid (supporting the rAAV replication and encapsidation). The packaged viruses are collected and gradient purified/concentrated, followed by infection of the breast cancer cell lines.

The drop in the endogenous KAI1 as-lncRNA, and the desired increase in KAI1 mRNA are tested. The cell phenotype is tested through assaying for cell-proliferation, -migration, -adhesion and cell invasion in cells showing the desired increase in KAI1 mRNA.

Example 18

Modulation of KAI1 as-lncRNA in Mouse Breast Tumor Xenografts

As there is no mouse or rat homologue to the SKAI1BC lncRNA, generating Genetically Engineered Mouse Model (GEMM) using for example constitutive/inducible SKAI1BC lncRNA, is irrelevant. Instead, in order to test the selected KAI as-lncRNA modulators in a pre-clinical setting, MDA-MB-231 cells are injected to the mouse mammary gland/fat pad, so that human cells initiated metastasis can occur (Holen et al., 2017). Subsequently, increasing levels of the selected KAI as-lncRNA modulators are injected to these mouse xenografts. A positive control is made by infecting the metastatic MDA-MB-231 cell line with TRIPZ lentivirus expressing the dox inducible KAI shRNA-1, so that reduction of breast metastasis is obtained, consequent of KAI mRNA stimulation.

A successful accomplishment of this first phase justifies the switch to testing the KAI as-lncRNA selected modulators in Patients Derived Xenografts (PDXs) generated by xenografting cancer tissue fragments obtained from patients to immune deficient mice (Holen et al. 2017). Generally, in contrast to conventional xenograft using cancer cell lines, PDXs are biologically more stable and recapitulate the individual tumor morphology, gene expression, and drug susceptibility of each patient. PDX models are thought to be more translationally relevant, especially as a drug development tool, because PDXs can capture the genetic character and heterogeneity that exists within a single patient's tumor and across a population of patients' tumors.

The invention claimed is:

1. A modulator of at least one antisense long non-coding RNA of the metastasis suppressor gene KAI1/cluster of differentiation 82 (CD82) (KAI1 as-lncRNA), wherein said KAI1 as-lncRNA has a length of about 700 to about 1000 nucleotides and is encoded upstream of the KAI1/CD82 gene transcription start site (TSS) in an antisense orientation, wherein said modulator comprises at least one nucleic acid molecule comprising at least one of: a single stranded DNA (ssDNA), a single stranded RNA (ssRNA), a double stranded DNA (dsDNA), a double stranded RNA (dsRNA), nucleic acid molecule having at least one modified nucleotide/s and any combinations thereof, and wherein said modulator reduces at least one of the level and activity of the KAI1 as-lncRNA transcript, thereby increasing the expression of the KAI1/CD82 gene.

2. The modulator according to claim 1, wherein the 5' terminus of said KAI1 as-lncRNA is located in an antisense orientation at position −386 of the KAI1 gene transcription start site (TSS), and wherein, optionally, said KAI1 as-lncRNA is at least one of:
 (a) is 792 nucleotides long
 (b) is the human KAI1 as-lncRNA (designated suppressor of KAI1 in breast cancer (SKAIBC)); and
 (c) comprises a nucleic acid sequence as denoted by SEQ ID NO: 46, or any fragments, homologs or variants thereof.

3. The modulator according to claim 1, wherein said nucleic acid molecule comprises at least one of a short hairpin RNA (shRNA), a small interfering RNA (siRNA), microRNA (miRNA), antisense oligonucleotide (ASO), Peptide-Nucleic Acid (PNA), and locked nucleic acid (LNA).

4. The modulator according to claim 3, wherein said nucleic acid modulator comprises at least one shRNA molecule, said shRNA comprising a nucleic acid sequence complementary at least in part to KAI1 as-lncRNA or to any fragment/s or variant/s thereof.

5. The modulator according to claim 4, wherein said nucleic acid modulator comprises at least one shRNA molecule, said shRNA comprising a nucleic acid sequence complementary at least in part to KAI1 as-lncRNA or to any fragment/s or variant/s thereof, and wherein said shRNA comprises a nucleic acid sequence comprising at least one of the nucleic acid sequence as denoted by SEQ ID NO: 6 and SEQ ID NO: 5.

6. The modulator according to claim 5, wherein said shRNA comprises nucleic acid sequences as denoted by SEQ ID NO: 5 and SEQ ID NO: 6, both separated by a loop region having a length of about 5 to about 40 nucleotides.

7. The modulator according to claim 6, wherein said modulator is an shRNA molecule comprising the nucleic acid sequence as denoted by at least one of SEQ ID NO. 4, SEQ ID NO. 18 and SEQ ID NO. 19, or any fragments, variants or derivatives thereof.

8. A delivery vehicle comprising at least one modulator according to claim 1, wherein, optionally, said delivery vehicle is a viral vector.

9. A composition comprising an effective amount of at least one modulator according to claim 1, and wherein said composition optionally further comprises at least one of pharmaceutically acceptable carrier/s, excipient/s, auxiliaries, and/or diluent/s.

10. A method for modulating the expression of the KAI1 gene in a cell, said method comprising the step of contacting said cell with a modulatory effective amount of at least one modulator of at least one antisense long non-coding RNA of the metastasis suppressor gene KAI1/cluster of differentiation 82 (CD82) (KAI1 as-lncRNA), or of any vehicle, matrix, nano-or micro-particle, or a composition comprising the same, wherein said KAI1 as-lncRNA has a length of about 700 to about 1000 nucleotides and is encoded upstream of the KAI1 gene TSS in an antisense orientation, wherein said modulator comprises at least one nucleic acid molecule comprising at least one of: a single stranded DNA (ssDNA), a single stranded RNA (ssRNA), a double stranded DNA (dsDNA), a double stranded RNA (dsRNA), nucleic acid molecule having at least one modified nucleotide/s and any combinations thereof, and wherein said modulator reduces at least one of the level and activity of the KAI1 as-lncRNA transcript, thereby increasing the expression of the KAI1/CD82 gene.

11. The method according to claim 10, wherein said method reduces at least one of the level and activity of KAI1 as-lncRNA, thereby increasing the expression of the KAI1/CD82 gene, and wherein optionally, said method results in at least one of reduction of cell migration, retardation of cell motility, increased cell adhesion, and/or inhibition of cell invasion.

12. The method according to claim 10, wherein said cell is of a subject suffering from a malignant disorder, wherein said malignant disorder is at least one of carcinoma, melanoma, sarcoma, lymphoma, and myeloma, optionally, said carcinoma being any one of breast carcinoma, prostate carcinoma, pancreatic carcinoma, non-small cell lung carcinoma, ovarian carcinoma, colorectal carcinoma, bladder carcinoma, cervical carcinoma, hepatocellular carcinoma, gastric carcinoma, laryngeal carcinoma, and thyroid cancer.

13. The method according to claim 10, for treating a malignant disorder in a subject in need thereof, said method comprising the step of administering to said subject a therapeutically effective amount of at least one of said modulator of at least one KAI1as-lncRNA, or of any vehicle, matrix, nano- or micro-particle, or a composition comprising the same, wherein said KAI1 as-lncRNA has a length of about 700 to about 1000 nucleotides and is encoded upstream of the KAI1 gene TSS, wherein said malignant disorder is at least one of carcinoma, melanoma, sarcoma, lymphoma, and myeloma, optionally, said carcinoma being any one of breast carcinoma, prostate carcinoma, pancreatic carcinoma, non-small cell lung carcinoma, ovarian carcinoma, colorectal carcinoma, bladder carcinoma, cervical carcinoma, hepatocellular carcinoma, gastric carcinoma, laryngeal carcinoma, and thyroid cancer.

14. The method according to claim 10, wherein said nucleic acid molecule comprises at least one of a short hairpin RNA (shRNA), a small interfering RNA (siRNA), microRNA (miRNA), antisense oligonucleotide (ASO), Peptide-Nucleic Acid (PNA), and locked nucleic acid (LNA).

15. The method according to claim 14, wherein said nucleic acid modulator comprises at least one shRNA molecule, said shRNA comprising a nucleic acid sequence complementary at least in part to KAI1 as-lncRNA.

16. The method according to claim 14, wherein said nucleic acid modulator comprises at least one shRNA molecule, said shRNA comprising a nucleic acid sequence complementary at least in part to KAI1 as-lncRNA, and wherein said shRNA comprises a nucleic acid sequence comprising at least one of the nucleic acid sequence as denoted by SEQ ID NO: 6 and SEQ ID NO: 5.

17. The method according to claim 16, wherein said shRNA comprises nucleic acid sequences as denoted by SEQ ID NO: 5 and SEQ ID NO: 6, both separated by a loop region having a length of about 5 to about 40 nucleotides.

18. The method according to claim 17, wherein said modulator is an shRNA molecule comprising the nucleic acid sequence as denoted by at least one of SEQ ID NO. 4, SEQ ID NO. 18 and SEQ ID NO. 19.

19. The method according to claim 13, wherein the malignant disorder is breast cancer or melanoma.

20. A method for inhibiting cancer cell motility, cell migration, cell invasiveness and/or metastasis in a subject having a malignant disorder selected from the group consisting of carcinoma, melanoma, sarcoma, lymphoma, and myeloma, optionally, said carcinoma being any one of breast carcinoma, prostate carcinoma, pancreatic carcinoma, non-small cell lung carcinoma, ovarian carcinoma, colorectal carcinoma, bladder carcinoma, cervical carcinoma, hepatocellular carcinoma, gastric carcinoma, laryngeal carcinoma, and thyroid cancer, the method comprising the step of administering to said subject a therapeutically effective amount of at least one modulator in accordance with claim 1, or any vehicle, matrix, nano- or micro-particle, or a composition comprising the same.

* * * * *